(12) United States Patent
Kakinuma et al.

(10) Patent No.: US 7,439,232 B2
(45) Date of Patent: Oct. 21, 2008

(54) HETEROARYL 5-THIO-β-D-GLUCOPYRANOSIDE DERIVATIVES AND THERAPEUTIC AGENTS FOR DIABETES CONTAINING THE SAME

(75) Inventors: Hiroyuki Kakinuma, Tokyo (JP); Masakazu Sato, Tokyo (JP); Hideaki Amada, Tokyo (JP); Hajime Asanuma, Tokyo (JP); Yuko Tsuchiya, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 343 days.

(21) Appl. No.: 10/551,115

(22) PCT Filed: Feb. 6, 2004

(86) PCT No.: PCT/JP2004/001272

§ 371 (c)(1),
(2), (4) Date: Sep. 28, 2005

(87) PCT Pub. No.: WO2004/089967

PCT Pub. Date: Oct. 21, 2004

(65) Prior Publication Data

US 2006/0194809 A1     Aug. 31, 2006

(30) Foreign Application Priority Data

Apr. 1, 2003 (JP) ............................. 2003-097838
Dec. 3, 2003 (JP) ............................. 2003-404959

(51) Int. Cl.
*A01N 43/04* (2006.01)
*A61K 31/70* (2006.01)
*C07H 15/00* (2006.01)
*C07H 17/00* (2006.01)
*C07G 3/00* (2006.01)
*C07G 11/00* (2006.01)

(52) U.S. Cl. ......................................... 514/24; 536/4.1
(58) Field of Classification Search ........................ None
See application file for complete search history.

(56) References Cited

U.S. PATENT DOCUMENTS

2004/0006025 A1    1/2004   Ohsumi et al.

2004/0138143 A1    7/2004   Glombik et al.
2005/0049203 A1    3/2005   Nishimura et al.

FOREIGN PATENT DOCUMENTS

| EP | 1 213 296 A1 | 6/2002 |
|---|---|---|
| EP | 1 364 958 A1 | 11/2003 |
| WO | WO 01/16147 A1 | 3/2001 |
| WO | WO 01/74834 A1 * | 10/2001 |
| WO | WO 02/36602 A1 | 5/2002 |
| WO | WO 02/068440 A1 | 9/2002 |
| WO | WO 03/000712 A1 | 1/2003 |
| WO | WO 2004/007517 A1 | 1/2004 |

OTHER PUBLICATIONS

Sakaguchi, et al., "Potential Radiosensitizing Agents. 4.2-Nitroimidazole Nucleosides," *J. Med. Chem.*, vol. 25, No. 11, pp. 1339-1342 (1982).

* cited by examiner

*Primary Examiner*—Patrick T Lewis
(74) *Attorney, Agent, or Firm*—Sughrue Mion, PLLC

(57) ABSTRACT

There is provided a heteroaryl 5-thio-β-D-glucopyranoside compound of the following formula, which has an inhibitory effect on SGLT2 activity, or a pharmaceutically acceptable salt thereof or a hydrate thereof. There is also provided a pharmaceutical preparation, particularly a prophylactic or therapeutic agent for diabetes, diabetes-related diseases or diabetic complications, which comprises such a compound as an active ingredient.

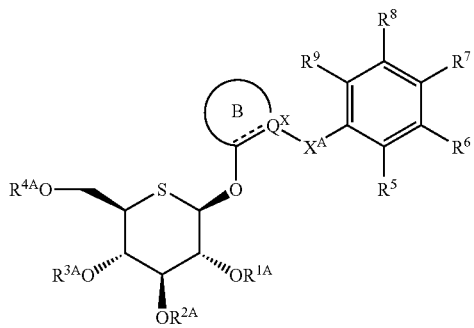

16 Claims, No Drawings

HETEROARYL 5-THIO-β-D-GLUCOPYRANOSIDE DERIVATIVES AND THERAPEUTIC AGENTS FOR DIABETES CONTAINING THE SAME

This is a U.S. national stage entry of Application No. PCT/JP2004/001272 filed Feb. 6, 2004.

TECHNICAL FIELD

The present invention relates to heteroaryl 5-thio-β-D-glucopyranoside compounds capable of inhibiting the activity of sodium-dependent glucose transporter 2 (SGLT2), which is specifically present in the kidney and is involved in glucose reabsorption. The present invention also relates to pharmaceutical preparations, particularly therapeutic agents for diabetes, which comprise such a compound as an active ingredient.

BACKGROUND ART

Chronic hyperglycemia is believed to reduce both insulin secretion and insulin sensitivity, which in turn will cause elevation of blood glucose levels and lead to exacerbation of diabetes. Drugs conventionally used as therapeutic agents for diabetes include biguanides, sulfonylureas, glycosidase inhibitors and insulin-resistance improving agents. However, adverse side effects of these drugs have been reported; for example, lactic acidosis for biguanides, hypoglycemia for sulfonylureas, as well as diarrhea and serious hepatic dysfunction for glycosidase inhibitors. It is therefore desirable to develop therapeutic agents for diabetes that depend on a new mechanism of action which is different from those conventionally proposed.

Phloridzin, a glucose derivative isolated from nature, has been identified as having a hypoglycemic effect by inhibiting excessive glucose reabsorption in the kidney to accelerate the glucose excretion (J. Clin. Invest., vol. 80, p. 1037, 1987; J. Clin. Invest., vol. 87, p. 1510, 1987). There have been indications that this glucose reabsorption event is mediated by sodium-dependent glucose transporter 2 (SGLT2) present at the S1 site of renal proximal tubules (J. Clin. Invest., vol. 93, p. 397, 1994).

Under these backgrounds, an increasing number of studies have been conducted to develop therapeutic agents for diabetes that depend on SGLT2 inhibition, and a large number of phloridzin derivatives have been reported (see European Patent Publication No. EP0850948, International Patent Publication Nos. WO0168660, WO0116147, WO0174834, WO0174835, WO0253573, WO0268439, WO0268440, WO0236602 and WO0288157).

When administered orally, phloridzin derivatives are hydrolyzed at glycosidic linkages by the action of glycosidase present in the small intestine, thus resulting in low absorption efficiency of unchanged form and a weak hypoglycemic effect. For this reason, various attempts have been made, for example, to increase absorption efficiency by administering phloridzin derivatives in the form of prodrugs and/or to prevent digestion by synthesizing compounds replaced by carbon-carbon linkages instead of glycosidic linkages (see United States Patent No. US20010041674, International Patent Publication Nos. WO0127128 and WO0283066).

However, since no chemical synthesis technique has been developed for β-selective glycosylation of 5-thioglucose derivatives in which the ring oxygen atom of glucose is replaced by a sulfur atom, there is no report on heteroaryl 5-thio-β-D-glucopyranoside derivatives. Thus, there is also no report on the SGLT2-inhibiting effect of heteroaryl 5-thio-β-D-glucopyranoside derivatives.

DISCLOSURE OF THE INVENTION

The object of the present invention is to provide novel compounds which have a hypoglycemic effect by inhibiting the activity of SGLT2 involved in glucose reabsorption in the kidney to accelerate excretion of urinary sugar.

As a result of extensive and intensive efforts made to overcome the problems stated above, the inventors of the present invention have found a method of enabling selective synthesis of 5-thio-β-D-glucopyranosides. Using this method, the inventors have also synthesized heteroaryl 5-thio-β-D-glucopyranoside derivatives or pharmaceutically acceptable salts thereof (hereinafter referred to as "the compound of the present invention") and have found that these compounds have an SGLT2-inhibiting effect. These findings led to the completion of the present invention.

Namely, the present invention is directed to a heteroaryl 5-thio-β-D-glucopyranoside compound of the following formula or a pharmaceutically acceptable salt thereof or a hydrate thereof:

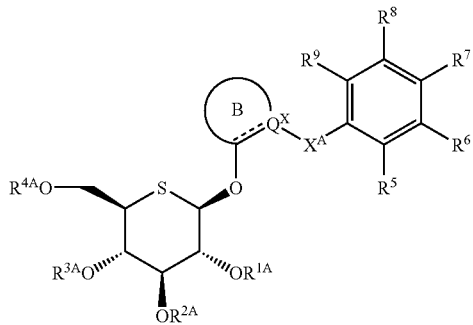

[wherein

B represents a heteroaryl group which may be substituted with any substituent, $R^{1A}$, $R^{2A}$, $R^{3A}$ and $R^{4A}$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group, $Q^X$ represents N or C, $X^A$ represents —(CH$_2$)n-, —CO(CH$_2$)n-, —C(OH)(CH$_2$)n-, —O—(CH$_2$)n-, —CONH(CH$_2$)n-, —NHCO(CH$_2$)n- (wherein n is an integer of 0 to 3), —COCH═CH—, —S— or —NH—, provided that when $Q^X$ is N, $X^A$ represents —(CH$_2$)n-, —CO(CH$_2$)n-, —C(OH)(CH$_2$)n-, —CONH (CH$_2$)n- (wherein n is an integer of 0 to 3) or —COCH═CH—, and $R^5$, $R^6$, $R^7$, $R^8$ and $R^9$, which may be the same or different, each represent:

a hydrogen atom;

a halogen atom;

a hydroxyl group;

a $C_{1-6}$ alkyl group which may be substituted with one or more (e.g., 1 to 6, preferably 1 to 4) substituents selected from the group consisting of a halogen atom and a hydroxyl group;

a group represented by the formula:

—(CH$_2$)m'-Q'

{wherein m' represents an integer of 0 to 4, and Q' represents a formyl group, an amino group, a nitro group, a cyano group, a carboxyl group, a sulfonic acid group, an optionally halogen-substituted $C_{1-6}$ alkoxy group, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group].

BEST MODE FOR CARRYING OUT THE INVENTION

According to another embodiment of the present invention, there is provided a compound of the above formula wherein $X^A$ is —(CH$_2$)n- or —CO(CH$_2$)n- (wherein n is an integer of 0 to 3), or a pharmaceutically acceptable salt thereof or a hydrate thereof.

According to another embodiment of the present invention, there is provided a compound of the above formula wherein $X^A$ is —CH$_2$— or —CO—, or a pharmaceutically acceptable salt thereof or a hydrate thereof.

According to another embodiment of the present invention, there is provided a compound of the above formula wherein $X^A$ is —CH$_2$—, or a pharmaceutically acceptable salt thereof or a hydrate thereof.

According to another embodiment of the present invention, there is provided a compound of the above formula wherein the moiety represented by the formula:

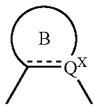

is a group represented by the formula:

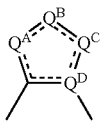

[wherein at least one of $Q^A$ to $Q^D$ represents a nitrogen atom and the other each independently represent —C-$Z^Y$, provided that when $Q^D$ is C, any one of the ring nitrogen atoms may be substituted with $Z^X$ (wherein $Z^X$ represents an optionally halogen-substituted $C_{1-6}$ alkyl group; an optionally halogen-substituted $C_{3-7}$ cycloalkyl group; a $C_{2-10}$ acyl group; a $C_{2-6}$ alkoxycarbonyl group; a phenyl or $C_{7-10}$ aralkyl group which may be substituted with one or more (preferably 1 to 4) substituents selected from the group consisting of a halogen atom, a $C_{1-6}$ alkyl group, a $C_{1-6}$ alkoxy group, an amino group, a nitro group, a cyano group, a carboxyl group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylamino group, an N,N-di($C_{1-6}$ alkyl)amino group, an N—($C_{1-6}$ alkyl)aminocarbonyl group and an N,N-di($C_{1-6}$ alkyl)aminocarbonyl group; a pyridyl group; a thienyl group; a furanyl group; or a pyrimidinyl group ($Z^X$ preferably represents an optionally halogen-substituted $C_{1-6}$ alkyl group; an optionally halogen-substituted $C_{3-7}$ cycloalkyl group; a $C_{2-10}$ acyl group; a $C_{2-6}$ alkoxycarbonyl group; or a phenyl or $C_{7-10}$ aralkyl group which may be substituted with one or more (preferably 1 to 4) substituents selected from the group consisting of a halogen atom, a $C_{1-6}$ alkyl group and a $C_{1-6}$ alkoxy group), and $Z^Y$ independently represents a hydrogen atom; a halogen atom; a $C_{1-6}$ alkyl group which may be substituted with one or more substituents selected from the group consisting of a halogen atom, a hydroxyl group and a $C_{1-6}$ alkoxy group; an optionally halogen-substituted $C_{3-7}$ cycloalkyl group; a carboxyl group; or a $C_{2-6}$ alkoxycarbonyl group)], or a pharmaceutically acceptable salt thereof or a hydrate thereof.

According to another embodiment of the present invention, there is provided a compound of the above formula wherein the moiety represented by the formula:

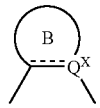

is a pyrazole group represented by the formula:

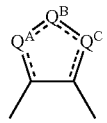

[wherein when $Q^A$ is N and $Q^B$ is —N-$Z^1$ or when $Q^A$ is —N-$Z^2$ and $Q^B$ is N, $Q^C$ represents —C-$Z^3$, or alternatively, when $Q^B$ is N and $Q^C$ is —N-$Z^4$ or when $Q^B$ is —N-$Z^5$ and $Q^C$ is N, $Q^A$ represents —C-$Z^6$ (wherein $Z^1$, $Z^2$, $Z^4$ and $Z^5$ each independently represent a hydrogen atom; an optionally halogen-substituted $C_{1-6}$ alkyl group; an optionally halogen-substituted $C_{3-7}$ cycloalkyl group; a $C_{2-10}$ acyl group; a $C_{2-6}$ alkoxycarbonyl group; a phenyl or $C_{7-10}$ aralkyl group which may be substituted with one or more (preferably 1 to 4) substituents selected from the group consisting of a halogen atom, a $C_{1-6}$ alkyl group, a $C_{1-6}$ alkoxy group, an amino group, a nitro group, a cyano group, a carboxyl group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylamino group, an N,N-di($C_{1-6}$ alkyl)amino group, an N—($C_{1-6}$ alkyl)aminocarbonyl group and an N,N-di($C_{1-6}$ alkyl)aminocarbonyl group; a pyridyl group; a thienyl group; a furanyl group; or a pyrimidinyl group ($Z^1$, $Z^2$, $Z^4$ and $Z^5$ preferably each independently represent a hydrogen atom; an optionally halogen-substituted $C_{1-6}$ alkyl group; an optionally halogen-substituted $C_{3-7}$ cycloalkyl group; a $C_{2-10}$ acyl group; a $C_{2-6}$ alkoxycarbonyl group; or a phenyl or $C_{7-10}$ aralkyl group which may be substituted with one or more (preferably 1 to 4) substituents selected from the group consisting of a halogen atom, a $C_{1-6}$ alkyl group and a $C_{1-6}$ alkoxy group), and $Z^3$ and $Z^6$ each independently represent a hydrogen atom; a halogen atom; a $C_{1-6}$ alkyl group which may be substituted with one or more (preferably 1 to 4) substituents selected from the group consisting of a halogen atom, a hydroxyl group and a $C_{1-6}$ alkoxy group; an optionally halogen-substituted $C_{3-7}$ cycloalkyl group; a carboxyl group; or a $C_{2-6}$ alkoxycarbonyl group)], or a pharmaceutically acceptable salt thereof or a hydrate thereof.

According to another embodiment of the present invention, there is provided a compound of the above formula wherein the moiety represented by the formula:

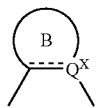

is a pyridyl group represented by the formula:

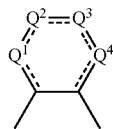

[wherein any one of $Q^1$ to $Q^4$ represents N and the other each independently represent —C-$Z^7$ (wherein $Z^7$ represents a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group)], or a pharmaceutically acceptable salt thereof or a hydrate thereof.

According to another embodiment of the present invention, there is provided a compound of the above formula wherein the moiety represented by the formula:

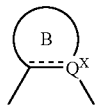

is a pyrimidyl group represented by the formula:

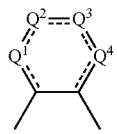

[wherein when $Q^1$ and $Q^3$ are each N, $Q^2$ and $Q^4$ each independently represent —C-$Z^8$, or alternatively, when $Q^2$ and $Q^4$ are each N, $Q^1$ and $Q^3$ each independently represent —C-$Z^9$ (wherein $Z^8$ and $Z^9$ each independently represent a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group)], or a pharmaceutically acceptable salt thereof or a hydrate thereof.

According to another embodiment of the present invention, there is provided a compound of the above formula wherein the moiety represented by the formula:

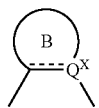

is a pyridazinyl group represented by the formula:

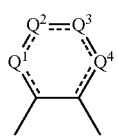

[wherein $Q^1$ and $Q^2$, $Q^2$ and $Q^3$, or $Q^3$ and $Q^4$ each represent N, and the other each represent —C-$Z^{10}$ (wherein $Z^{10}$ independently represents a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group)], or a pharmaceutically acceptable salt thereof or a hydrate thereof.

According to another embodiment of the present invention, there is provided a compound of the above formula wherein the moiety represented by the formula:

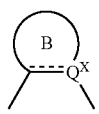

is a pyrazinyl group represented by the formula:

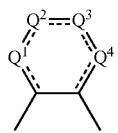

[wherein $Q^1$ and $Q^4$ each represent N and the other each represent —C-$Z^{11}$ (wherein $Z^{11}$ independently represents a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group)], or a pharmaceutically acceptable salt thereof or a hydrate thereof.

According to another embodiment of the present invention, there is provided a 5-thio-β-D-glucopyranoside compound of the following formula or a pharmaceutically acceptable salt thereof:

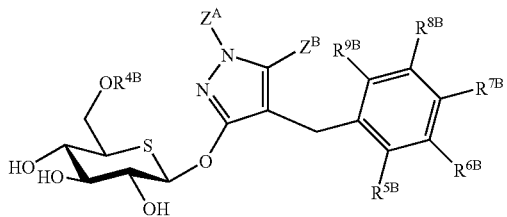

(wherein $Z^A$ represents a hydrogen atom, a $C_{1-6}$ alkyl group, a halogen-substituted $C_{1-6}$ alkyl group, a $C_{3-6}$ cycloalkyl group, a benzyl group, a $C_{2-10}$ acyl group or a $C_{2-6}$ alkoxycarbonyl group, $Z^B$ represents a $C_{1-6}$ alkyl group or a halogen-substituted $C_{1-6}$ alkyl group, $R^{5B}$ to $R^{9B}$, which may be the same or different, each represent a hydrogen atom, a halogen atom, a $C_{1-6}$ alkyl group, a halogen-substituted $C_{1-6}$ alkyl group, a $C_{3-6}$ cycloalkyl group, a $C_{1-6}$ alkoxy group, a halogen-substituted $C_{1-6}$ alkoxy group or a $C_{1-6}$ alkylthio group, and $R^{4B}$ represents a hydrogen atom, a $C_{2-10}$ acyl group or a $C_{2-6}$ alkoxycarbonyl group).

According to another embodiment of the present invention, there is provided a pharmaceutical preparation, which comprises any one of the above 5-thio-β-D-glucopyranoside compounds or a pharmaceutically acceptable salt thereof or a hydrate thereof as an active ingredient.

According to another embodiment of the present invention, there is provided such a pharmaceutical preparation which is an inhibitor of sodium-dependent glucose transporter 2 activity.

According to another embodiment of the present invention, there is provided such a pharmaceutical preparation which is a prophylactic or therapeutic agent for diabetes, diabetes-related diseases or diabetic complications.

According to another embodiment of the present invention, there is provided a pharmaceutical preparation, which comprises any one of the above 5-thio-β-D-glucopyranoside compounds or a pharmaceutically acceptable salt thereof or a hydrate thereof, in combination with at least one drug selected from the group consisting of an insulin sensitizer (which is selected from the group consisting of a PPARγ agonist, a PPARα/γ agonist, a PPARδ agonist and a PPARα/γ/δ agonist), a glycosidase inhibitor, a biguanide, an insulin secretagogue, an insulin formulation and a dipeptidyl peptidase IV inhibitor.

According to another embodiment of the present invention, there is provided a pharmaceutical preparation, which comprises any one of the above 5-thio-β-D-glucopyranoside compounds or a pharmaceutically acceptable salt thereof or a hydrate thereof, in combination with at least one drug selected from the group consisting of a hydroxymethylglutaryl coenzyme A reductase inhibitor, a fibrate, a squalene synthase inhibitor, an acyl-coenzyme A:cholesterol acyltransferase inhibitor, a low-density lipoprotein receptor promoter, a microsomal triglyceride transfer protein inhibitor and an anorectic.

The terms used herein are defined as follows (in the definitions, the designation "$C_{x-y}$" is intended to mean a group containing x to y carbon atoms).

The term "heteroaryl group" refers to an aromatic heterocyclic group containing one or more heteroatoms selected from O, S and N and preferably having 5 to 10 atoms in its ring. Examples include a pyrazolyl group, a thiazolyl group, an isothiazolyl group, a thiadiazolyl group, an imidazolyl group, a furyl group, a thienyl group, an oxazolyl group, an isoxazolyl group, a pyrrolyl group, (1,2,3)- and (1,2,4)-triazolyl groups, a tetrazolyl group, a pyridyl group, a pyrimidinyl group, a pyrazinyl group, a pyridazinyl group, a triazinyl group, a pyranyl group, an oxadiazolyl group, a furazanyl group, a quinolyl group, an isoquinolyl group, a benzofuranyl group, an isobenzofuranyl group, an indolyl group, an isoindolyl group, an indazolyl group, a benzimidazolyl group, a benztriazolyl group, a benzoxazolyl group, a benzothiazolyl group, a benzo[b]thiophenyl group, a benzothiadiazolyl group, a phthalazinyl group, a naphthylizinyl group, a quinoxalinyl group, a quinazolinyl group and a cinnolinyl group.

The term "heteroaryl group" also encompasses condensed rings having a monocyclic ring, in which an aromatic heterocyclic group is partially saturated. Examples include a 2,3-dihydro-1H-indolyl group, a 2,3-dihydro-1H-indazolyl group, a 2,3-dihydro-1H-benzotriazolyl group, a 2,3-dihydro-1H-benzoxazolyl group, a 2,3-dihydro-1H-benzothiazolyl group, a benzo[1,3]oxathiolyl group, a benzo[1,3]dioxolyl group and a 2H-chromenyl group.

Such a partially saturated condensed heterocyclic ring may be substituted with =O. Examples of such a ring include a 2-oxo-1,3-dihydro-1H-indolyl group, a 3-oxo-1,2-dihydro-1H-indazolyl group, a 2-oxo-3H-benzoxazolyl group, a 2-oxo-3H-benzothiazolyl group, a 2-oxo-benzo[1,3]oxathiolyl group, a 2-oxo-benzo[1,3]dioxolyl group and a 2-oxo-chromenyl group.

With respect to the term "any substituent" which may be substituted on the moiety B, examples include =O; a halogen atom; a hydroxyl group; $—^+NH_3$; $—^+N(CH_3)_3$; $—BH_3^-$; $—O^-$; a $C_{1-6}$ alkyl group which may be substituted with one or more (e.g., 1 to 6, preferably 1 to 4) substituents selected from the group consisting of a halogen atom and a hydroxyl group; a group represented by the formula:

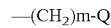

{wherein m represents an integer of 0 to 4 (preferably m is 0), Q represents a formyl group, an amino group, a nitro group, a cyano group, a carboxyl group, a sulfonic acid group, an optionally halogen-substituted $C_{1-6}$ alkoxy group, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group}; and a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group, a $C_{1-6}$ alkoxy group, an amino group, a nitro group, a cyano group, a carboxyl group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylamino group, an N,N-di($C_{1-6}$ alkyl)amino group, an N—($C_{1-6}$ alkyl)aminocarbonyl group and an N,N-di($C_{1-6}$ alkyl)aminocarbonyl group (preferably selected from the group consisting of a halogen atom, a hydroxyl group, a $C_{1-6}$ alkyl group and a $C_{1-6}$ alkoxy group).

The term "$C_{1-6}$ alkoxy-$C_{2-10}$ acyl group" is intended to mean a structure composed of a linear or branched $C_{1-6}$ alkoxy group and a $C_{2-10}$ acyl group. Preferred are a $C_{1-6}$ alkoxy-$C_{2-6}$ alkanoyl group and the like.

The term "$C_{1-6}$ alkoxy-$C_{2-6}$ alkoxycarbonyl group" is intended to mean a structure composed of a linear or branched $C_{1-6}$ alkoxy group and a $C_{2-6}$ alkoxycarbonyl group.

The term "$C_{2-10}$ acyl group" is intended to mean a linear or branched aliphatic acyl group (preferably a $C_{2-6}$ alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, with an acetyl group being preferred.

The term "$C_{7-10}$ aralkyl group" refers to an aryl alkyl group containing 7 to 10 carbon atoms. Examples include a benzyl group and a phenylethyl group.

The term "$C_{1-6}$ alkoxy group" is intended to mean a linear or branched alkoxy group containing 1 to 6 carbon atoms. Preferred are $C_{1-4}$ alkoxy groups including a methoxy group, an ethoxy group, a propoxy group, an isopropoxy group, a n-butoxy group, an isobutoxy group and a tert-butoxy group.

The term "$C_{2-6}$ alkoxycarbonyl group" is intended to mean a structure composed of a linear or branched $C_{1-5}$ alkoxy group and a carbonyl group. Preferred are $C_{2-5}$ alkoxycarbonyl groups including a methoxycarbonyl group, an ethoxycarbonyl group, a propoxycarbonyl group, an isopropoxycarbonyl group and a butoxycarbonyl group. Among them, a methoxycarbonyl group is preferred.

The term "$C_{1-6}$ alkyl group" is intended to mean a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group, a tert-amyl group, a 3-methylbutyl group and a neopentyl group.

The term "halogen atom" encompasses a fluorine atom, a chlorine atom, a bromine atom, an iodine atom and the like.

The term "halogen-substituted $C_{1-6}$ alkyl group" refers to a $C_{1-6}$ alkyl group whose hydrogen atoms are replaced by one or more (e.g., 1 to 6, preferably 1 to 4) halogen atoms (preferably fluorine atoms). Examples include a trifluoromethyl group, a 1,1,1-trifluoroethyl group, a 1,1,1-trifluoropropyl group, a 1,1,1-trifluorobutyl group and a 1,3-difluoroprop-2-yl group, with a trifluoromethyl group and a 1,1,1-trifluoroethyl group being preferred.

The term "hydroxy-substituted $C_{1-6}$ alkyl group" refers to an alkyl group whose hydrogen atoms are replaced by one or more (e.g., 1 to 6, preferably 1 to 4) hydroxyl groups. Preferred is a hydroxy-$C_{1-6}$ alkyl group (i.e., a $C_{1-6}$ alkyl group substituted with one hydroxyl group), and more preferred is a hydroxy-$C_{1-4}$ alkyl group. Examples include a hydroxymethyl group, a hydroxyethyl group (e.g., a 1-hydroxyethyl group, a 2-hydroxyethyl group, a 1-hydroxy-1-methyl-ethyl group), a hydroxypropyl group and a hydroxybutyl group.

The term "halogen-substituted $C_{1-6}$ alkoxy group" refers to an alkoxy group whose hydrogen atoms are replaced by one or more (e.g., 1 to 6, preferably 1 to 4) halogen atoms. Examples include a trifluoromethoxy group, a 1,1,1-trifluoroethoxy group, a 1,1,1-trifluoropropoxy group and a 1,1,1-trifluorobutoxy group, with a trifluoromethoxy group and a 1,1,1-trifluoroethoxy group being preferred.

The term "$C_{1-6}$ alkoxy-$C_{1-6}$ alkoxy group" is intended to mean, for example, a methoxymethoxy group.

The term "$C_{2-10}$ acyloxy group" is intended to mean a structure composed of a $C_{2-10}$ acyl group and a —O— moiety. Preferred are a $C_{2-6}$ alkanoyloxy group (e.g., an acetyloxy group) and a benzoyloxy group.

The term "$C_{1-6}$ alkylthio group" is intended to mean a structure composed of a linear or branched $C_{1-6}$ alkyl group and one thio group (—S—), preferably refers to a $C_{1-4}$ alkylthio group. Examples of a $C_{1-6}$ alkylthio group include a methylthio group, an ethylthio group and a propylthio group.

The term "$C_{1-6}$ alkylsulfinyl group" is intended to mean a structure composed of a $C_{1-6}$ alkyl group and a sulfinyl group (—SO—). Preferred are a methanesulfinyl group and an ethanesulfinyl group.

The term "$C_{1-6}$ alkylsulfonyl group" is intended to mean a structure composed of a $C_{1-6}$ alkyl group and a sulfonyl group (—SO$_2$—). Preferred are a methanesulfonyl group and an ethanesulfonyl group.

The term "$C_{2-10}$ acylamino group" is intended to mean a structure composed of a $C_{2-10}$ acyl group and an amino group. Preferred is an acetylamino group.

The term "$C_{1-6}$ alkylsulfonylamino group" is intended to mean a structure composed of a $C_{1-6}$ alkylsulfonyl group and an amino group. Examples include a methanesulfonylamino group and an ethanesulfonylamino group.

The term "$C_{1-6}$ alkylamino group" is intended to mean a structure composed of a $C_{1-6}$ alkyl group and an amino group. Examples include a methylamino group and an ethylamino group.

The term "N,N-di($C_{1-6}$ alkyl)amino group" is intended to mean a structure composed of two $C_{1-6}$ alkyl groups and an amino group. Examples include a dimethylamino group and a diethylamino group.

The term "N—($C_{1-6}$ alkyl)aminocarbonyl group" is intended to mean a structure composed of an N—($C_{1-6}$ alkyl)amino group and a carbonyl group. Preferred are N—($C_{1-4}$ alkyl)aminocarbonyl groups including an N-methylaminocarbonyl group.

The term "N,N-di($C_{1-6}$ alkyl)aminocarbonyl group" is intended to mean a structure composed of an N,N-di($C_{1-6}$ alkyl)amino group and a carbonyl group. Preferred are N,N-di($C_{1-4}$ alkyl)aminocarbonyl groups including an N,N-dimethylaminocarbonyl group.

Examples of the groups —(CH$_2$)m-Q and —(CH$_2$)m'-Q' wherein m and m' each represent an integer of 1 or more will be provided below.

In a case where Q and Q' each represent a $C_{1-6}$ alkoxy group, examples include a methoxymethyl group.

In a case where Q and Q' each represent an amino group, examples include an aminomethyl group.

In a case where Q and Q' each represent a $C_{2-10}$ acyloxy group, examples include an acetyloxymethyl group and a benzoyloxyethyl group.

In a case where Q and Q' each represent a $C_{2-10}$ acylamino group, examples include an acetylaminomethyl group.

In a case where Q and Q' each represent an N,N-di($C_{1-6}$ alkyl)amino group, examples include an N,N-dimethylaminomethyl group.

The term "$C_{3-7}$ cycloalkyl group" is intended to mean a cyclic alkyl group containing 3 to 7 carbon atoms. Examples include a cyclopropyl group, a cyclobutyl group, a cyclopentyl group and a cyclohexyl group, with a cyclopropyl group and a cyclobutyl group being preferred.

The term "halogen-substituted $C_{3-7}$ cycloalkyl group" refers to a $C_{3-7}$ cycloalkyl group whose hydrogen atoms are replaced by one or more (e.g., 1 to 6, preferably 1 to 4) halogen atoms (preferably fluorine atoms).

The term "$C_{3-7}$ cycloalkyloxy group" is intended to mean a structure composed of a $C_{3-7}$ cycloalkyl group and a —O— moiety. Examples include a cyclopropyloxy group and a cyclopentyloxy group.

The term "aryl group" encompasses a phenyl group and a naphthyl group (including a 1-naphthyl group and a 2-naphthyl group), preferably refers to a phenyl group.

The term "aryloxy group" is intended to mean a structure composed of an aryl group and a —O— moiety. Examples include a phenoxy group and a naphthoxy group.

The term "$C_{7-10}$ aralkyloxy group" is intended to mean a structure composed of a $C_{7-10}$ aralkyl group and a —O— moiety. Examples include a benzyloxy group and a phenylethyloxy group.

The term "$C_{7-10}$ aralkylamino group" is intended to mean a structure composed of a $C_{7-10}$ aralkyl group and an —NH— moiety. Examples include a benzylamino group and a phenylethylamino group.

The term "4- to 6-membered heterocycloalkyl group" refers to a 4- to 6-membered heterocycloalkyl group containing at least one heteroatom (oxygen atom, nitrogen atom or sulfur atom) in the ring. For example, such a group may be a cyclic amino group that contains one or more nitrogen atoms in the ring and may further contain one or more oxygen atoms and/or sulfur atoms. Examples include a morpholino group, a piperidinyl group, a piperazinyl group and a 1-pyrrolidinyl group.

Examples of substituted heterocycloalkyl groups include those substituted with a $C_{1-6}$ alkyl group(s).

In addition, the term "pharmaceutically acceptable salt" is intended to mean, for example, a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethylsuccinate salt, a lactobionate salt, a gluconate salt, a glucoheptate salt, a benzoate salt, a methanesulfonate salt, an ethanesulfonate salt, a 2-hydroxyethanesulfonate salt, a benzenesulfonate salt, a p-toluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer and a salt with a carboxyvinyl polymer.

Representative embodiments of the compound of the present invention will be provided below.

The moiety represented by the formula:

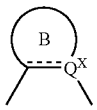

is preferably an optionally substituted 5- or 6-membered aromatic heterocyclic group, more preferably an optionally substituted aromatic heterocyclic group having nitrogen as a ring member. Examples of an "aromatic heterocyclic group having nitrogen as a ring member" include a pyrrolyl group, a pyrazolyl group, an imidazolyl group, (1,2,3)- and (1,2,4)-triazolyl groups, (1,2,3)- and (1,2,4)-triazolyl groups, a tetrazolyl group, a pyridyl group, a pyrimidinyl group, a pyrazinyl group and a pyridazinyl group.

Preferred examples of $X_A$ are —(CH$_2$)n- and —CO(CH$_2$)n-(wherein n is an integer of 0 to 3), more preferably —CH$_2$— and —CO—, and even more preferably —CH$_2$—.

$R^5$, $R^6$, $R^7$, $R^8$ and $R^9$ may be the same or different and each preferably represent:

a hydrogen atom;

a halogen atom;

a hydroxyl group;

a $C_{1-6}$ alkyl group which may be substituted with one or more (e.g., 1 to 6, preferably 1 to 4) substituents selected from the group consisting of a halogen atom and a hydroxyl group;

a group represented by the formula:

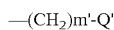

{wherein m' represents an integer of 0 to 4 (more preferably m' is 0), and Q' represents a carboxyl group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, or a $C_{1-6}$ alkylsulfonyl group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, or a heteroaryl group, provided that each of these groups may be substituted with 1 to 4 substituents selected from the group consisting of a halogen atom, a hydroxyl group, a $C_{1-6}$ alkyl group and a $C_{1-6}$ alkoxy group.

More preferably, $R^5$, $R^6$, $R^7$, $R^8$ and $R^9$ each represent:

a hydrogen atom;

a halogen atom;

a $C_{1-6}$ alkyl group which may be substituted with one or more (e.g., 1 to 6, preferably 1 to 4) substituents selected from the group consisting of a halogen atom and a hydroxyl group;

a group represented by the formula:

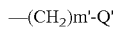

{wherein m' represents an integer of 0 to 4 (more preferably m' is 0), and Q' represents a carboxyl group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, or a $C_{1-6}$ alkylsulfonyl group}; or a $C_{3-7}$ cycloalkyl group, a $C_{7-10}$ aralkyloxy group, or a heteroaryl group, provided that each of these groups may be substituted with 1 to 4 substituents selected from the group consisting of a halogen atom, a hydroxyl group, a $C_{1-6}$ alkyl group and a $C_{1-6}$ alkoxy group.

Even more preferably, only $R^7$ is a substituent selected from the preferred examples or the more preferred examples mentioned above, and the other $R^5$, $R^6$, $R^8$ and $R^9$ each represent a hydrogen atom, a halogen atom, or a $C_{1-6}$ alkyl or $C_{1-6}$ alkoxy group which may be substituted with one or more (e.g., 1 to 6, preferably 1 to 4) halogen atoms.

Preferred compounds are any of those specifically listed below:

4'-(4'-ethylbenzyl)-1'-isopropyl-5'-methyl-1'H-pyrazol-3'-yl 5-thio-β-D-glucopyranoside (Compound 1);

4'-(4'-ethylbenzyl)-5'-methyl-1'H-pyrazol-3'-yl 5-thio-β-D-glucopyranoside (Compound 2);

4'-[(3'-fluoro-4'-methylphenyl)methyl]-5'-methyl-1'H-pyrazol-3'-yl 5-thio-β-D-glucopyranoside (Compound 3);

4'-[(3'-fluoro-4'-methoxyphenyl)methyl]-5'-methyl-1'H-pyrazol-3'-yl 5-thio-β-D-glucopyranoside (Compound 4);

4'-[(4'-methoxyphenyl)methyl]-5'-methyl-1'H-pyrazol-3'-yl 5-thio-β-D-glucopyranoside (Compound 5);

4'-[(2'-fluoro-4'-methoxyphenyl)methyl]-5'-methyl-1'H-pyrazol-3'-yl 5-thio-β-D-glucopyranoside (Compound 6);

1'-acetyl-4'-[(3'-fluoro-4'-methylphenyl)methyl]-5'-methyl-pyrazol-3'-yl 5-thio-β-D-glucopyranoside (Compound 7);

1'-ethoxycarbonyl-4'-[(4'-methoxyphenyl)methyl]-5'-methyl-pyrazol-3'-yl 6-O-ethoxycarbonyl-5-thio-β-D-glucopyranoside (Compound 8);

4'-(4'-methylthiobenzyl)-5'-methyl-1'H-pyrazol-3'-yl 5-thio-β-D-glucopyranoside (Compound 9);

4'-(4'-methanesulfonylbenzyl)-5'-methyl-1'H-pyrazol-3'-yl 5-thio-β-D-glucopyranoside (Compound 10);

1'-ethoxycarbonyl-4'-[(4'-ethylphenyl)methyl]-5'-methyl-pyrazol-3'-yl 6-O-ethoxycarbonyl-5-thio-β-D-glucopyranoside (Compound 11);

4'-(4'-cyclopropylbenzyl)-5'-methyl-1'H-pyrazol-3'-yl 5-thio-β-D-glucopyranoside (Compound 12);

4'-(4'-ethylbenzyl)-1'-isopropyl-5'-trifluoromethyl-1'H-pyrazol-3'-yl 5-thio-β-D-glucopyranoside (Compound 13);

1'-cyclobutyl-4'-(4'-ethylbenzyl)-5'-trifluoromethyl-1'H-pyrazol-3'-yl 5-thio-β-D-glucopyranoside (Compound 14);

4'-(4'-ethylbenzyl)-1'-(1',3'-difluoro-2'-propyl)-5'-trifluoromethyl-1'H-pyrazol-3'-yl 5-thio-β-D-glucopyranoside (Compound 15);

1'-benzyl-4'-(4'-ethylbenzyl)-5'-trifluoromethyl-1'H-pyrazol-3'-yl 5-thio-β-D-glucopyranoside (Compound 16);

4'-(4'-ethylbenzyl)-5'-isopropyl-1'H-pyrazol-3'-yl 5-thio-β-D-glucopyranoside (Compound 17);

4'-[(2'-benzyloxyphenyl)methyl]-5'-isopropyl-1'H-pyrazol-3'-yl 5-thio-β-D-glucopyranoside (Compound 18);

1'-(4'-methylphenyl)-4'-(4'-ethylbenzyl)-5'-methyl-1'H-pyrazol-3'-yl 5-thio-β-D-glucopyranoside (Compound 19);

4'-(4'-ethylbenzyl)pyridin-3'-yl 5-thio-β-D-glucopyranoside (Compound 20);

3'-(4'-ethylbenzyl)pyridin-2'-yl 5-thio-β-D-glucopyranoside (Compound 21);

2'-(4'-ethylbenzyl)pyridin-3'-yl 5-thio-β-D-glucopyranoside (Compound 22);

3'-(4'-ethylbenzyl)-1'H-pyrazin-2'-yl 5-thio-β-D-glucopyranoside (Compound 23);

5'-(ethylbenzyl)-2',6'-dimethyl-3'H-pyrimidin-4'-yl 5-thio-β-D-glucopyranoside (Compound 24);

3'-(4'-ethylbenzyl)-4',6'-dimethylpyridin-2'-yl 5-thio-β-D-glucopyranoside (Compound 25);

3'-(4'-ethylbenzyl)pyridin-4'-yl 5-thio-β-D-glucopyranoside (Compound 26);

4'-(4'-cyclopropylbenzyl)pyridin-3'-yl 5-thio-β-D-glucopyranoside (Compound 27);

4'-(4'-isopropylbenzyl)pyridin-3'-yl 5-thio-β-D-glucopyranoside (Compound 28);

4'-(4'-methoxybenzyl)pyridin-3'-yl 5-thio-β-D-glucopyranoside (Compound 29);

4'-[4'-(1'-hydroxy-1'-methyl-ethyl)benzyl]pyridin-3'-yl 5-thio-β-D-glucopyranoside (Compound 30);

4'-(4'-methoxycarbonylbenzyl)pyridin-3'-yl 5-thio-β-D-glucopyranoside (Compound 31);

4'-[4'-(2'-hydroxyethyl)benzyl]pyridin-3'-yl 5-thio-β-D-glucopyranoside (Compound 32);

4'-(3'-fluoro-4'-methoxybenzyl)pyridin-3'-yl 5-thio-β-D-glucopyranoside (Compound 33);

3'-(4'-methoxybenzyl)pyridin-2'-yl 5-thio-β-D-glucopyranoside (Compound 34);

4'-(2'-fluoro-4'-methoxybenzyl)pyridin-3'-yl 5-thio-β-D-glucopyranoside (Compound 35);

6'-(N-acetylamino)-3'-(4'-ethylbenzyl)pyridin-2'-yl 5-thio-β-D-glucopyranoside (Compound 36);

4'-(4'-pyrazol-1'-ylbenzyl)pyridin-3'-yl 5-thio-β-D-glucopyranoside (Compound 37); and 4'-(4'-ethylbenzyl)-pyridazin-3'-yl 5-thio-β-D-glucopyranoside (Compound 38).

How to prepare the compound of the present invention will be explained below.

In accordance with the following scheme, a 5-thio-D-glucopyranoside compound of Formula (IV) and a heteroaryl alcohol of Formula (VI) may be reacted under Mitsunobu reaction (Org. Reactions, vol. 42, p. 335) conditions using a phosphine represented by $PR^XR^YR^Z$ and an azo reagent represented by $R^{21}$—N=N—$R^{22}$ to prepare a heteroaryl 5-thio-β-D-glucopyranoside compound.

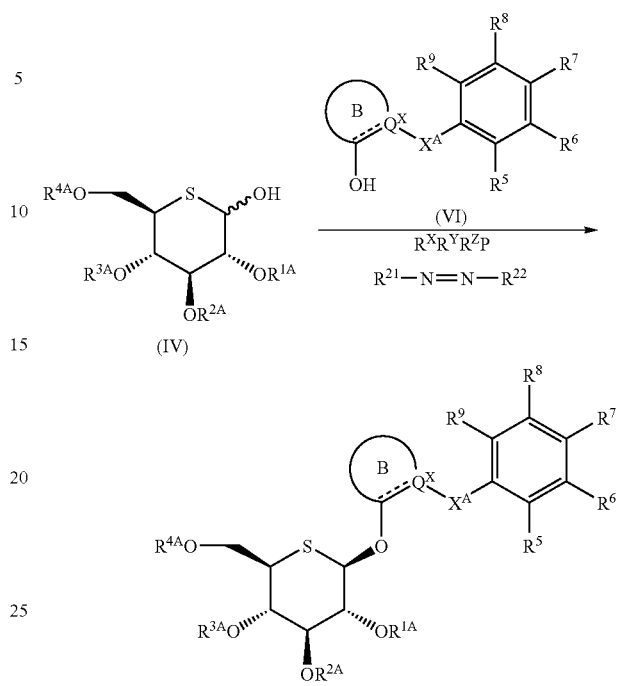

If necessary, the resulting compound may further be deprotected to remove the protecting groups on its sugar hydroxyl groups and/or optionally modified into a prodrug form, thus obtaining the compound of the present invention.

The term "heteroaryl alcohol" refers to a heteroaryl compound substituted with an OH group and also encompasses the keto form of keto-enol tautomers.

In the phrase "phosphine represented by $PR^XR^YR^Z$", $R^X$ to $R^Z$, which may be the same or different, each represent a phenyl group which may be substituted with a $C_{1-6}$ alkyl group (e.g., a phenyl group, a tolyl group), a pyridyl group, or a $C_{1-6}$ alkyl group (e.g., a methyl group, a n-butyl group, a t-butyl group). Preferred examples of such a phosphine include triphenylphosphine, tri-n-butylphosphine, tri-t-butylphosphine, tritolylphosphine and diphenyl-2-pyridylphosphine. Among them, preferred are triphenylphosphine and diphenyl-2-pyridylphosphine, and more preferred is triphenylphosphine.

In the phrase "azo reagent represented by $R^{21}$—N=N—$R^{22}$," $R^{21}$ and $R^{22}$, which may be the same or different, each represent a $C_{2-5}$ alkoxycarbonyl group, an N,N-di-$C_{1-4}$ alkylaminocarbonyl group, or a piperidinocarbonyl group. Preferred examples of such an azo reagent include diethyl azodicarboxylate, diisopropyl azodicarboxylate and di-tert-butyl azodicarboxylate, as well as 1,1'-azobis(N,N-dimethylformamide) and 1,1'-(azodicarbonyl)dipiperidine. Among them, preferred are diethyl azodicarboxylate (DEAD), diisopropyl azodicarboxylate and the like.

Solvents available for use in the reaction include tetrahydrofuran, dioxane, toluene, methylene chloride, chloroform, acetonitrile, ethyl acetate, dimethyl sulfoxide and N,N-dimethylformamide. Preferred are tetrahydrofuran and toluene, and more preferred is toluene.

The reaction temperature preferably ranges from −20° C. to room temperature.

A specific example of how to prepare the compound of the present invention will be given below.

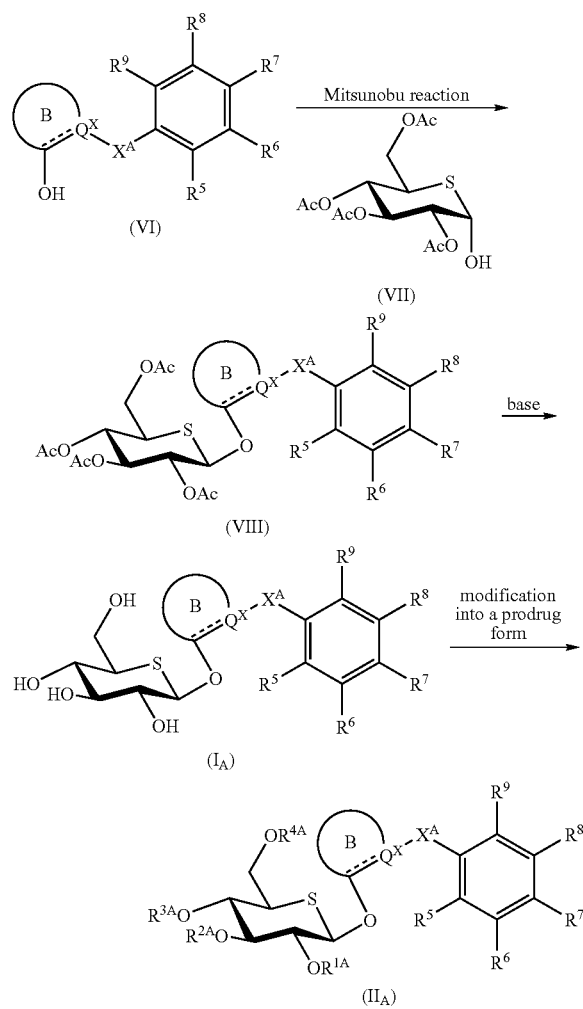

A heteroaryl alcohol of Formula (VI) may be reacted with 5-thioglucose (VII) whose sugar hydroxyl groups are protected with protecting groups (e.g., acyl groups such as acetyl groups) through the Mitsunobu reaction under the above conditions to selectively prepare a 5-thio-β-D-glucoside compound (VIII). Then, Compound (VIII) may be deprotected to remove, e.g., the protecting groups on the sugar hydroxyl groups (e.g., acyl groups such as acetyl groups) or may be treated such that substituents introduced for the purpose of increasing the reaction yield are removed or converted into other substituents, as illustrated below, thereby obtaining Compound ($I_A$). Subsequently, Compound ($I_A$) may optionally be modified into a prodrug from to give Compound ($II_A$).

In the case of protecting groups for hydroxyl groups, removal of the protecting groups may be accomplished, for example, under the following conditions. In a case where protecting groups for hydroxyl groups are acyl groups, it is possible to use a base such as sodium methoxide, sodium hydroxide, lithium hydroxide, potassium carbonate, cesium carbonate or triethylamine. Likewise, in a case where the protecting groups are acetal groups, it is possible to use hydrochloric acid, acetic acid, p-toluenesulfonic acid monohydrate or the like. Likewise, in a case where the protecting groups are silyl groups, it is possible to use n-$Bu_4NF$, hydrogen fluoride-pyridine or the like. In a case where the protecting groups are aralkyl groups, it is possible to use Pd/activated charcoal-hydrogen or the like.

Solvents suitable for removal of the above protecting groups include methanol, ethanol and aqueous methanol.

Modification into a prodrug form may be accomplished by using a reagent such as an acid anhydride or a chloroformate ester in an appropriate solvent (e.g., collidine, pyridine, N,N-dimethylformamide) to convert the glycosidic hydroxyl groups and the heteroaryl group (e.g., the 1-position nitrogen in the case of pyrazole) into prodrug forms, thus obtaining Compound ($II^4$) according to the present invention (wherein $R^{14}$ to $R^{4,4}$ each represent a group constituting a prodrug).

Examples of a "group constituting a prodrug" include protecting groups for hydroxyl groups or nitrogen atoms which can be commonly used in prodrugs, such as a $C_{2-10}$ acyl group (e.g., a $C_{2-8}$ alkanoyl group (preferably a $C_{2-6}$ alkanoyl group) or a benzoyl group), a $C_{2-6}$ alkoxycarbonyl group, a $C_{1-6}$ alkoxy-$C_{2-10}$ acyl group (preferably a $C_{1-6}$ alkoxy-$C_{2-6}$ alkanoyl group) and a $C_{1-6}$ alkoxy-$C_{2-6}$ alkoxycarbonyl group.

Alternatively, by controlling the reaction conditions, only —$R^{4,4}$ can be converted into a group constituting a prodrug. In this case, examples of $R^{4,4}$ include a $C_{2-6}$ alkanoyl group and a $C_{2-6}$ alkoxycarbonyl group.

Introduction of a substituent onto a pyrazolyl ring at an N atom may be accomplished by reacting pyrazolyl 5-thio-β-D-glucoside with $Z^1J$ (wherein $Z^1$ is as defined above excluding a hydrogen atom and J represents a halogen atom, a mesyloxy group or a tosyloxy group), so that the hydrogen in N—H which is a ring member of the pyrazole ring is replaced by $Z^1$. Solvents preferred for this reaction include tetrahydrofuran, dioxane, toluene, methylene chloride, chloroform, acetonitrile, ethyl acetate, dimethyl sulfoxide and N,N-dimethylformamide. In this case, a base preferred for use is triethylamine, N-ethyl-N,N-diisopropylamine, pyridine, potassium carbonate, calcium carbonate, cesium carbonate, sodium hydride, sodium methoxide, potassium tert-butoxide or the like. The reaction may be performed at a reaction temperature ranging from 0° C. to room temperature, preferably at room temperature, for 2 to 24 hours.

The starting materials used in this reaction may be commercially available or synthesized as follows.

5-Thio-D-glucopyranose (IV) can be prepared as follows, by way of example.

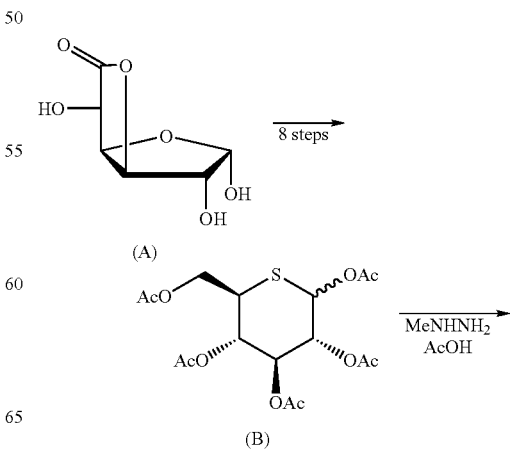

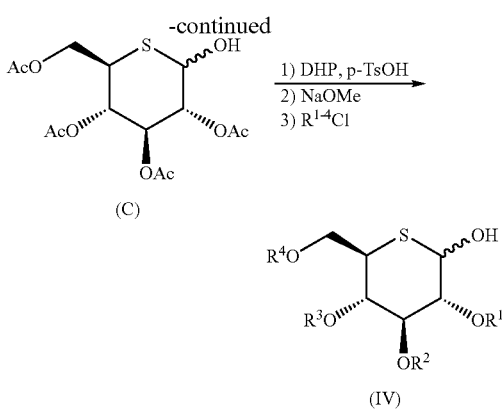

The penta-O-acetate derivative (B) (Tetrahedron Lett., vol. 22, p. 5061, 1981; J. Org. Chem., vol. 31, p. 1514, 1966) can be synthesized via 8 steps from D-glucofurano-3,6-lactone (A).

Next, Compound (B) may be treated in an appropriate solvent (e.g., DMF, THF, methanol, ethanol) using hydrazine acetate (Tetrahedron, Lett., vol. 33, p. 7675, 1992) or benzylamine, preferably a 1:1 mixture of methylhydrazine and acetic acid, to effect selective deprotection of the 1-position acetyl group, thereby preparing Compound (C).

The reaction temperature ranges from room temperature to 80° C., while the reaction time ranges from 20 minutes to 24 hours.

After the 1-position hydroxyl group of Compound (C) is protected (e.g., with a tetrahydropyranyl group), the compound may be deprotected to remove the acetyl groups and treated with, e.g., a $C_{2-6}$ alkanoyl chloride or benzoyl chloride under basic conditions, thereby giving a 5-thio-D-glucopyranose derivative (IV) (wherein $R^1$, $R^2$, $R^3$ and $R^4$, which may be the same or different, each represent a $C_{2-6}$ alkanoyl group or a benzoyl group) (Chem. Lett., p. 626, 2002).

A heteroaryl alcohol of Formula (VI) corresponding to the aglycon can be synthesized by reference to the following official gazettes: International Patent Publication Nos. WO0116147, WO0268439, WO0253573, WO0268440, WO0288157, WO0298893, WO0236602, WO0300712 and WO0320737.

When a heteroaryl alcohol to be glycosylated is substituted with an electron-withdrawing group(s) or has a high alcoholic acidity, such a compound ensures a high yield of glycosylation reaction.

This is because the alcoholic acidity of a heteroaryl alcohol would contribute to the reaction yield in the glycosylation reaction of the present invention.

Specific examples include heteroaryl groups in which the moiety

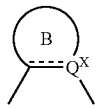

in a heteroaryl alcohol is substituted with 1 to 4 electron-withdrawing groups. To ensure a high yield of the reaction, the $pK_a$ (25° C., 1 atm) of a heteroaryl alcohol, which is used as an index of acidity, is preferably set to about 11 or below, more preferably about 9 or below.

Examples of heteroaryl alcohols having a high alcohol acidity include heterocyclic rings containing one oxygen or sulfur atom and one or more nitrogen atoms, exemplified by oxazole, thiazole, thiadiazole, benzoxazole, benzothiazole and benzothiadiazole.

As used herein, the term "electron-withdrawing group" refers to a substituent that is more likely to attract electrons from the atom where the substituent is attached when compared to a hydrogen atom, thus meaning that such a group attracts electrons as a result of the sum of substituent effects including an inductive effect and a mesomeric effect (or a resonance effect). Such an electron-withdrawing group preferably reduces the $pK_a$ of a heteroaryl alcohol to about 11 or below, more preferably about 9 or below.

Representative examples of electron-withdrawing groups include =O, a formyl group, a nitro group, a cyano group, a carboxyl group, a sulfonic acid group, —$^+NH_3$, —$^+N(CH_3)_3$, —$BH_3^-$, —$O^-$, a $C_{1-6}$ alkyl group substituted with a halogen atom (preferably a fluorine atom or a chlorine atom) (e.g., —$CF_3$, —$C(CH_2CH_2F)_2$, —$CCl_3$), a $C_{2-10}$ acyl group (e.g., —$COCH_3$, —COPh (Ph means a phenyl group)) or a $C_{2-6}$ alkoxycarbonyl group (e.g., —$CO_2CH_3$, —$CO_2C_2H_5$), a $C_{1-6}$ alkylsulfonyl group (e.g., —$SO_2CH_3$) and a halogen atom.

The preferred type and substitution position of an electron-withdrawing group may optionally be selected depending on the type of heteroaryl group to be substituted.

For example, in the case of a pyrazole group whose ring N atom is substituted with a substituent, a preferred substituent is a $C_{2-10}$ acyl group (e.g., —$COCH_3$, —COPh), a $C_{2-6}$ alkoxycarbonyl group (e.g., —$CO_2CH_3$, —$CO_2C_2H_5$) or the like. Since these groups can be readily removed by hydrolysis after glycosylation reaction, they are favorable as substituents that are to be introduced for the purpose of ensuring a high yield of compounds having an N-unsubstituted pyrazole group.

In the case of a pyridyl group, for the same reason as mentioned above, it is also favorable to introduce —$BH_3^-$, —$O^-$ or the like onto its ring N atom to form a pyridinium salt for the purpose of ensuring a high yield of compounds having a pyridyl group.

Likewise, a condensed heterocyclic ring in which a heteroaryl alcohol is partially saturated (e.g., a 2-oxo-1,3-dihydro-1H-indolyl group, a 3-oxo-1,2-dihydro-1H-indazolyl group, a 2-oxo-3H-benzoxazolyl group, a 2-oxo-3H-benzothiazolyl group, a 2-oxo-benzo[1,3]oxathiolyl group, a 2-oxo-benzo[1,3]dioxolyl group, a 2-oxo-chromenyl group) can be glycosylated in high yield when substituted with =O.

A heteroaryl group to be glycosylated may be introduced with an electron-withdrawing group(s) and then glycosylated, followed by processes such as catalytic hydrogenation, hydrolysis or decarboxylation to remove the electron-withdrawing group(s), or alternatively, followed by techniques well known to those skilled in the art (e.g., reduction) to convert each electron-withdrawing group into any other substituent, thus providing a heteroaryl 5-thio-β-D-aldohexopyranoside compound of interest in high yield.

For example, when using a starting material having an electron-withdrawing group (e.g., an acetyl group) introduced onto a pyrazole ring N atom, glycosylation reaction can be performed in high yield. Subsequently, the acetyl group or the like may be hydrolyzed to give an N-unsubstituted pyrazolyl 5-thio-β-D-glucopyranoside compound with higher efficiency.

More specifically, replacement of 1,2-dihydro-4-(4-ethyl-benzyl)-5-methyl-3H-pyrazol-3-one (13) by its N-acetyl compound (14) produced a 3-fold increase in the yield of glycosylation reaction.

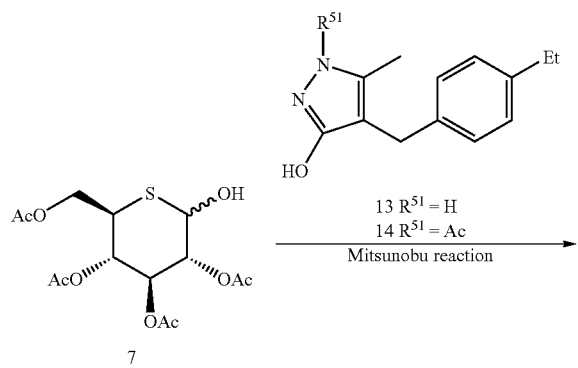

13 R⁵¹ = H
14 R⁵¹ = Ac
Mitsunobu reaction

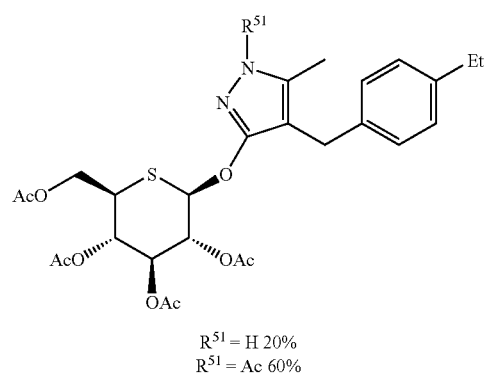

R⁵¹ = H 20%
R⁵¹ = Ac 60%

Likewise, when using a starting material having —BH₃⁻ introduced onto a pyridine ring at the N atom, side reactions can be prevented during glycosylation reaction. Subsequently, —BH₃⁻ may be hydrolyzed to give a pyridyl 5-thio-β-D-glucopyranoside compound with high efficiency.

More specifically, it has been confirmed that the use of 4-(4-ethylbenzyl)-3-hydroxypyridinium borane achieved prevention of side reactions such as acyl transfer of sugar during the Mitsunobu reaction.

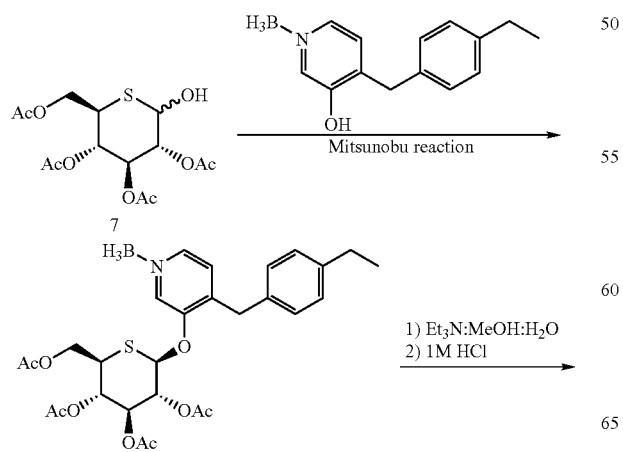

1) Et₃N:MeOH:H₂O
2) 1M HCl

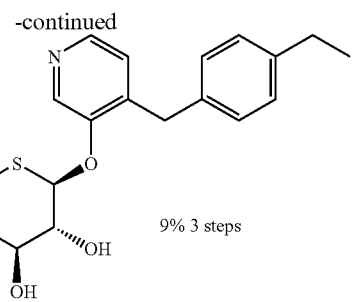

9% 3 steps

Likewise, when using a heteroaryl alcohol having a benzoyl group as a starting material, glycosylation reaction can be performed in high yield. Subsequently, the benzoyl group may be converted into a benzyl group to give a benzyl-substituted heteroaryl 5-thio-β-D-glucopyranoside compound with higher efficiency.

More specifically, a pyridine compound having a benzoyl group may be used and glycosylated, followed by reduction of the carbonyl moiety in the benzoyl group to give a benzyl-substituted pyridyl 5-thio-β-D-glucopyranoside compound in high yield.

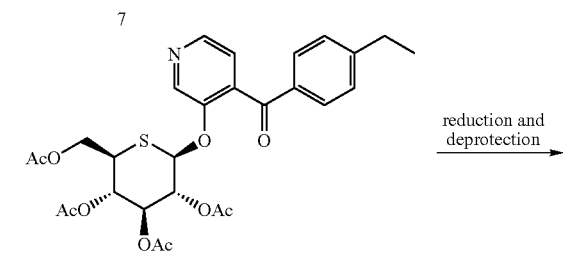

Mitsunobu reaction 68% reduction and deprotection

An example will be given below to illustrate how to prepare a starting compound of Formula (IV) used in the preparation of the compound of the present invention.

4-Benzyl-3-hydroxypyrazole compound

A compound having a substituent on a pyrazole ring at an N atom can be prepared from a compound of Formula (III$_A$) as follows:

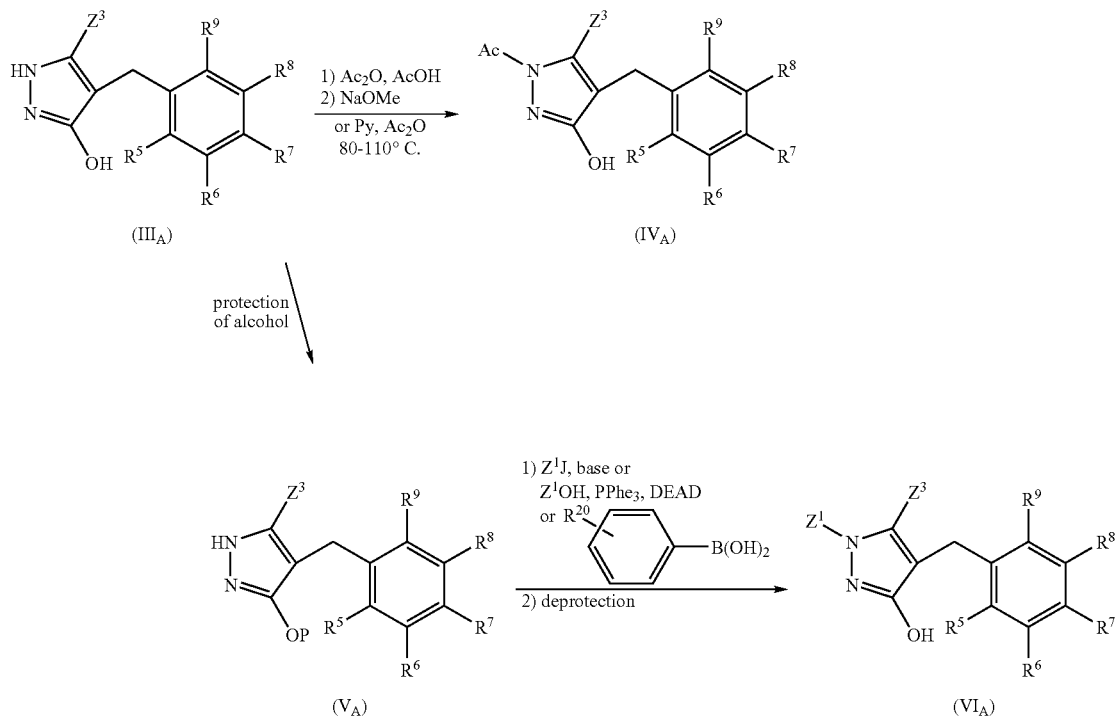

(wherein P represents a protecting group such as a benzyl group or a tert-butyldimethylsilyl group, J represents a leaving group such as a halogen atom, a mesyloxy group or a tosyloxy group, $R^{20}$ represents a hydrogen atom, a $C_{1-6}$ alkyl group, a $C_{1-6}$ alkoxy group, a halogen atom, an amino group, a nitro group, a cyano group, a carboxyl group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylamino group, an N,N-di($C_{1-6}$ alkyl)amino group, an N—($C_{1-6}$ alkyl)aminocarbonyl group or an N,N-di($C_{1-6}$ alkyl)aminocarbonyl group, $Z^1$ is as defined above excluding a hydrogen atom, and the other symbols $Z^3$ and $R^5$ to $R^9$ are as defined above).

The pyrazole compound ($III_A$) may be synthesized by reference to J. Med. Chem., vol. 39, p. 3920, 1996 or International Patent Publication Nos. WO0116147, WO0253573, WO0268439, WO0268440, WO0236602 and WO0288157.

(A) After N-, O-diacylation (diacetylation in the above scheme) of pyrazole ($III_A$) (acetic anhydride-acetic acid, pyridine-acetic anhydride), the resulting compound may be treated with, e.g., sodium methoxide or potassium carbonate in an appropriate solvent (e.g., N,N-dimethylformamide, tetrahydrofuran, methanol, ethanol) to selectively deprotect the O-acyl group (the O-acetyl group in the above scheme), thereby preparing Compound ($IV_A$). Alternatively, 1 equivalent of acetic anhydride may be used in a pyridine solvent to selectively effect N-acylation (acetylation in the above scheme) of Compound ($III_A$), thereby preparing Compound ($IV_A$). In this case, the reaction temperature preferably ranges from 80° C. to 110° C.

(B)
(1) Alternatively, the hydroxyl group of pyrazole ($III_A$) may be protected with a protecting group P (e.g., a benzyl group or a tert-butyldimethylsilyl group) to give Compound ($V_A$).
(2) Next, Compound ($V_A$) may be reacted with $Z^1J$ (wherein $Z^1$ is as defined above excluding a hydrogen atom and J represents a halogen atom, a mesyloxy group or a tosyloxy group), so that the hydrogen in N—H which is a ring member of the pyrazole ring is replaced by $Z^1$. Solvents preferred for this reaction include tetrahydrofuran, dioxane, toluene, methylene chloride, chloroform, acetonitrile, ethyl acetate, dimethyl sulfoxide and N,N-dimethylformamide. In this case, a base preferred for use is triethylamine, N,N-diisopropylethylamine, pyridine, potassium carbonate, calcium carbonate, cesium carbonate, sodium hydride, sodium methoxide, potassium tert-butoxide or the like. The reaction may be performed at a reaction temperature ranging from 0° C. to room temperature, preferably at room temperature, for 2 to 24 hours.
(2') Alternatively, various alcohols ($Z^1OH$) corresponding to Compound ($V_A$) may also be used for the Mitsunobu reaction (Org. Reactions, vol. 42, p. 335) in the presence of a phosphine and an azo reagent, so that the hydrogen in N—H which is a ring member of the pyrazole ring can be replaced by $Z^1$. Solvents available for use in the Mitsunobu reaction include tetrahydrofuran, dioxane, toluene, methylene chloride, chloroform, acetonitrile, ethyl acetate, dimethyl sulfoxide and N,N-dimethylformamide, with tetrahydrofuran and toluene being preferred. Phosphines available for use include triphenylphosphine, tri-n-butylphosphine, tri-t-butylphosphine, tritolylphosphine and diphenyl-2-pyridylphosphine, with triphenylphosphine being preferred. Azo reagents available for use include diethyl azodicarboxylate, diisopropyl azodicarboxylate and di-tert-butyl azodicarboxylate, with diethyl azodicarboxylate and diisopropyl azodicarboxylate being preferred. The reaction temperature preferably ranges from −20° C. to room temperature.

(2″) Alternatively, Compound ($V_A$) may be reacted with a phenylboronic acid derivative in an appropriate solvent (e.g., methylene chloride, chloroform, tetrahydrofuran) using, e.g., $Cu(OAc)_2$, $PdCl_2$, $Pd(OAc)_2$ or $Pd(PPh_3)_4$ as a catalyst in the presence or absence of pyridine and molecular sieves 4A, so that the hydrogen in N—H which is a ring member of the pyrazole ring can be replaced by a phenyl group.

(3) The protecting group P may then be deprotected in a routine manner to prepare Intermediate ($VI_A$).

3-Benzyl-2-hydroxypyridine or
4-benzyl-3-hydroxypyridine and
3-hydroxypyridazine compounds

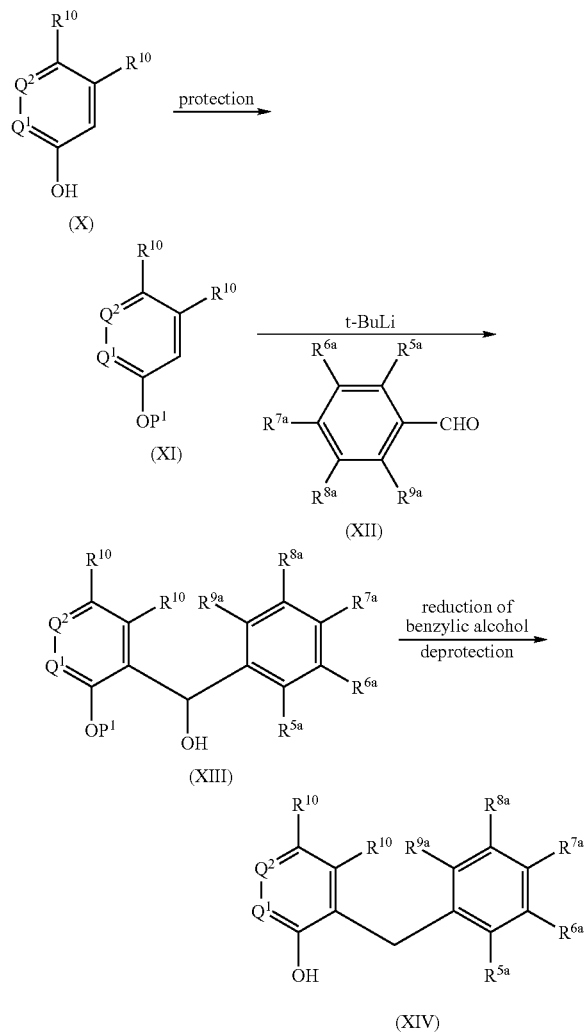

[wherein
one of $Q^1$ and $Q^2$ represents N and the other represents —C-$Z^7$, or both of $Q^1$ and $Q^2$ represent N (wherein $Z^7$ represents a hydrogen atom, a $C_{1-6}$ alkyl group or a halogen atom), $R^{10}$ preferably represents a hydrogen atom, a $C_{1-6}$ alkyl group or a halogen atom, and $R^{5a}$ to $R^{9a}$ each preferably represent:

a hydrogen atom;

a halogen atom;

a $C_{1-6}$ alkyl group which may be substituted with one or more (e.g., 1 to 6, preferably 1 to 4) substituents selected from the group consisting of a halogen atom and a hydroxyl group;

a group represented by the formula:

—(CH$_2$)m'-Q'

{wherein m' represents an integer of 0 to 4, and Q' represents an amino group, a carboxyl group, an optionally halogen-substituted $C_{1-6}$ alkoxy group, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{1-6}$ alkylsulfonylamino group, an N,N-di($C_{1-6}$ alkyl)amino group, or an N,N-di($C_{1-6}$ alkyl)aminocarbonyl group}; or a $C_{3-7}$ cycloalkyl group, a $C_{3-7}$ cycloalkyloxy group, a $C_{7-10}$ aralkyl group, a $C_{7-10}$ aralkyloxy group, an aryl group, an aryloxy group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group].

(1) The hydroxyl group of Compound (X) may be protected with a protecting group $P^1$ (e.g., a methyl group, a methoxymethyl group, a benzyl group, a tert-butyldimethylsilyl group, a 2-(triethylsilyl)ethoxymethyl group) to give Compound (XI).

(2) Next, in an appropriate solvent (e.g., diethyl ether, tetrahydrofuran), Compound (XI) may be treated with tert-butyllithium, lithium diisopropylamide (LDA), lithium-2,2,6,6-tetramethylpiperidide (LTMP) or mesityllithium (2,4,6-trimethylphenyllithium) at −78° C. to −20° C. and then condensed with Compound (XII) to give Compound (XIII). The reaction temperature for condensation ranges from −78° C. to 20° C., while the reaction time ranges from 0.5 to 6 hours.

(3) Next, catalytic hydrogenation may be performed on the alcohol at the benzyl position of Compound (XIII) using a catalyst such as palladium/activated charcoal or palladium hydroxide under a hydrogen atmosphere to prepare Compound (XIV). Solvents used in this case include, for example, methanol, ethanol, isopropanol, ethyl acetate and acetic acid. Alternatively, the alcohol at the benzyl position of Compound (XIII) may be reduced using, e.g., triethylsilane-BF$_3$OEt$_2$, triethylsilane-trifluoroacetic acid or Ph$_2$SiHCl—InCl$_3$ (J. Org. Chem., vol. 66, p. 7741, 2001). Solvents used in this case include acetonitrile, tetrahydrofuran, dioxane, toluene, methylene chloride, chloroform, 1,2-dichloroethane and N,N-dimethylformamide. Although the reaction temperature will vary depending on the types of reagent and solvent used, it ranges from −30° C. to 100° C.

(4) Next, the protecting group $P^1$ may be deprotected in a routine manner to prepare Intermediate (XIV). Depending on the combination between compound and protecting group, deprotection of $P^1$ may precede the reduction reaction of the alcohol at the benzyl position.

The above compound of Formula (XIV) may also be prepared in the manner shown in the following scheme:

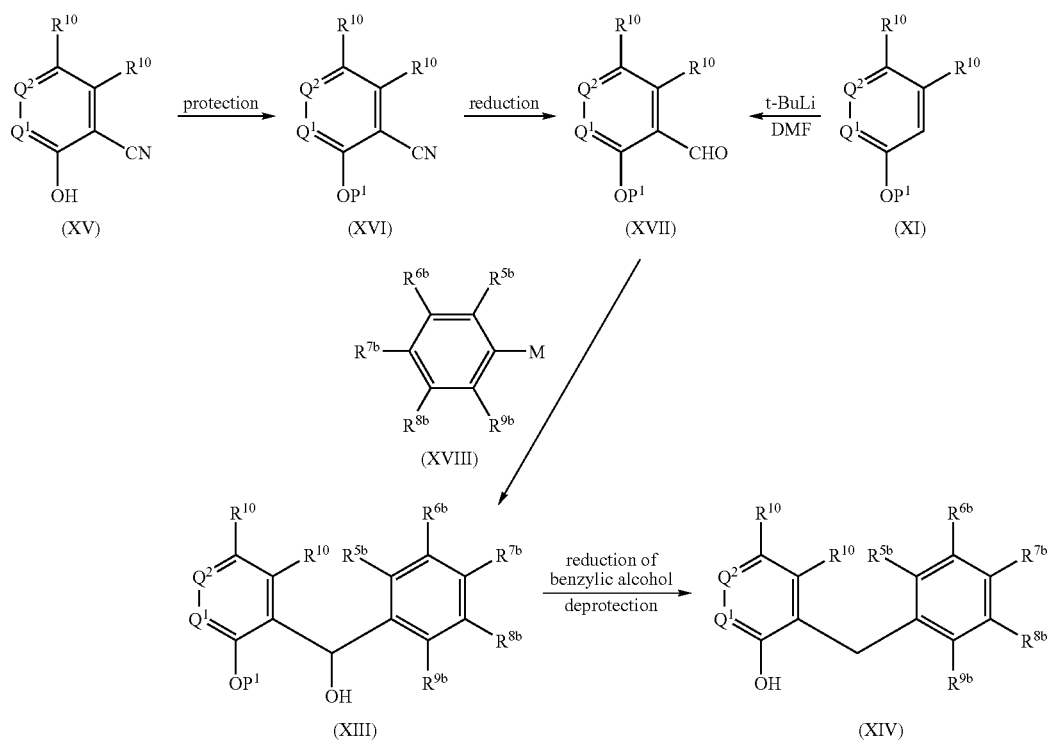

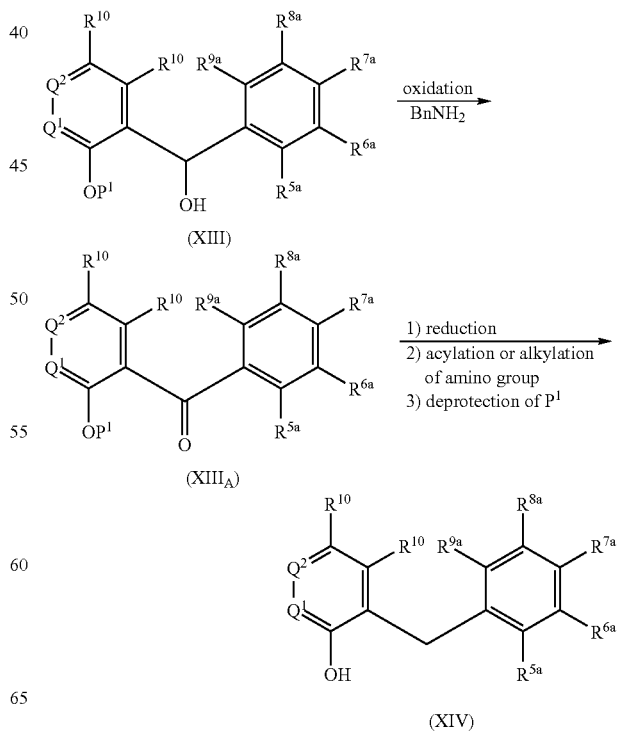

[wherein
M represents Li, MgBr, MgCl or MgI, and
$R^{5b}$ to $R^{9b}$ each preferably represent:
a hydrogen atom;
a group represented by the formula:

—$(CH_2)m'$-Q'

{wherein m' represents an integer of 0 to 4, and Q' represents a carboxyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonylamino group, an N,N-di($C_{1-6}$ alkyl)amino group, or an N,N-di($C_{1-6}$ alkyl)aminocarbonyl group}; or a $C_{3-7}$ cycloalkyl group, a $C_{3-7}$ cycloalkyloxy group, a $C_{7-10}$ aralkyl group, a $C_{7-10}$ aralkyloxy group, an aryl group, an aryloxy group, a heteroaryl group, or a 4- to 6-membered heterocycloalkyl group, provided that each of these groups may be substituted with 1 to 4 substituents selected from the group consisting of a $C_{1-6}$ alkyl group and a $C_{1-6}$ alkoxy group].

(1) The hydroxyl group of Compound (XV) may be protected with a protecting group $P^1$ (e.g., a methyl group, a methoxymethyl group, a benzyl group, a tert-butyldimethylsilyl group, a 2-(triethylsilyl)ethoxymethyl group) to give Compound (XVI). Next, in an appropriate solvent (e.g., diethyl ether, tetrahydrofuran), Compound (XVI) may be treated with a reducing agent such as diisobutylaluminum hydride at −78° C. to 20° C. to give Compound (XVII).

(1') Alternatively, in an appropriate solvent (e.g., diethyl ether, tetrahydrofuran), Compound (XI) may be treated with tert-butyllithium, LDA, LTMP or mesityllithium (2,4,6-trimethylphenyllithium) at −78° C. to −20° C., followed by addition of N,N-dimethylformamide to give Compound (XVII). In this case, the reaction temperature ranges from −78° C. to 20° C., preferably −78° C. to −30° C., while the reaction time ranges from 0.5 to 6 hours.

(2) Next, in an appropriate solvent (e.g., diethyl ether, tetrahydrofuran), Compound (XVII) may be treated with Compound (XVIII) to give Compound (XIII).

(3) In the next step, deprotection and reduction may be performed in the same manner as shown above to prepare Compound (XIV).

A compound having an amino group, an aminoalkyl group or an aminoacyl group on a pyridine ring at a C atom can be prepared from a compound of Formula (XIII) (wherein one of $Q^1$ and $Q^2$ represents N and the other represents —C-$Z^7$, and $Z^7$ represents a halogen atom) as follows:

[wherein P¹ represents a protecting group such as a methyl group or a 2-(trimethylsilyl)ethoxymethyl group, and the other symbols are as defined above].

(1) Compound (XIII) may be oxidized with, e.g., Dess-Martin periodine, o-iodoxybenzoic acid (IBX) or manganese dioxide (J. Chem. Soc., p. 1094, 1952) to give a ketone. Solvents used in this case include methylene chloride, chloroform, toluene, tetrahydrofuran and dimethyl sulfoxide, and the reaction temperature ranges from 0° C. to reflux. Next, the ketone thus obtained may be treated with benzylamine in the presence of a base such as potassium carbonate, sodium carbonate, cesium carbonate or sodium hydride to give Compound (XIII$_A$) (wherein one of Q¹ and Q² represents N and the other represents —C—NHBn). This reaction may be performed in a solvent such as N,N-dimethylformamide, diethyl ether or tetrahydrofuran or may be performed without any solvent.

(2) Next, catalytic hydrogenation may be performed using a catalyst such as palladium/activated charcoal or palladium hydroxide under a hydrogen atmosphere to reduce the benzyl position of Compound (XIII$_A$), while simultaneously removing Bn from —C—NHBn to give an amino group (—C—NH$_2$). Solvents used in this case include, for example, methanol, ethanol, isopropanol, ethyl acetate and acetic acid.

(3) Next, the amino compound thus obtained may be treated with acetic anhydride or a C$_{2-10}$ acyl chloride in the presence of a base such as pyridine, collidine, triethylamine or potassium carbonate to effect N—C$_{2-10}$ acylation.

Alternatively, the above amino compound may be treated with a C$_{1-6}$ alkyl halide in an appropriate solvent (e.g., N,N-dimethylformamide, diethyl ether, tetrahydrofuran) in the presence of a base such as potassium carbonate, sodium carbonate, cesium carbonate or sodium hydride to give a C$_{1-6}$ alkylamino derivative or an N,N-di(C$_{1-6}$ alkyl)amino derivative. Alternatively, in an appropriate solvent (e.g., N,N-dimethylformamide, diethyl ether, tetrahydrofuran), the above amino compound may be treated with paraformaldehyde and NaBH$_3$CN to give a methylamino derivative or an N,N-dimethylamino derivative.

(4) Finally, the protecting group P¹ may be removed in a routine manner to prepare Intermediate (XIV).

2-Benzyl-3-hydroxypyridine compound

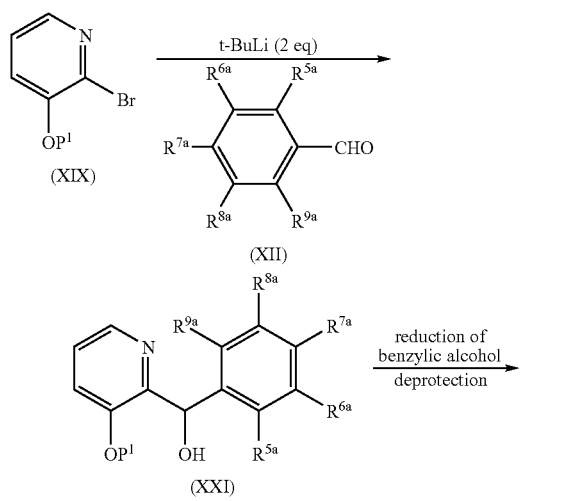

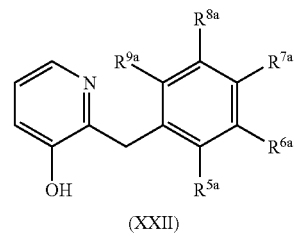

(wherein the symbols are as defined above).

In an appropriate solvent (e.g., diethyl ether, tetrahydrofuran), Compound (XIX) may be treated with 2 equivalents of t-butyllithium at −78° C. to −20° C. and then condensed with Compound (XII) to give Compound (XXI). The reaction temperature for condensation ranges from −78° C. to 20° C., while the reaction time ranges from 0.5 to 6 hours. In the next step, deprotection and reduction may be performed in the same manner as shown above to prepare Compound (XXII).

3-Benzyl-4-hydroxypyridine compound

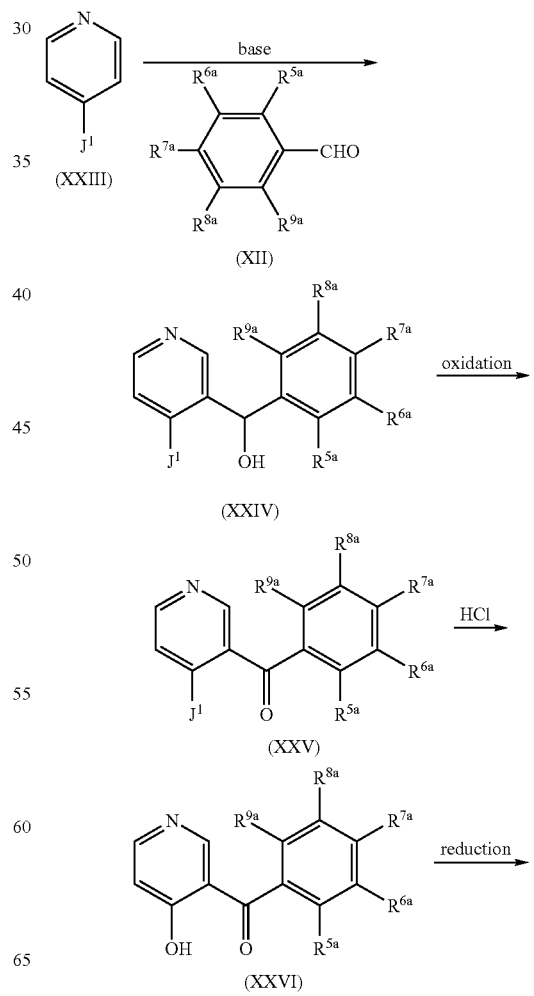

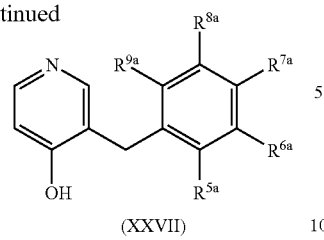

(XXVII)

(wherein J¹ represents a halogen atom and the other symbols are as defined above).

(1) In an appropriate solvent (e.g., diethyl ether, tetrahydrofuran), Compound (XXIII) may be treated at −78° C. to −20° C. by addition of a base such as LDA to effect selective lithiation at the ortho position relative to J¹ (J. Heterocyclic. Chem., vol. 25, p. 81, 1988). The resulting compound may be condensed with Compound (XII) to give Compound (XXIV). The reaction temperature for condensation ranges from −78° C. to 20° C., while the reaction time ranges from 0.5 to 1 hour.
(2) Next, Compound (XXIV) may be oxidized with, e.g., Dess-Martin periodine, IBX or manganese dioxide (J. Chem. Soc., p. 1094, 1952) to give Compound (XXV).
(3) Next, Compound (XXV) may be heated under reflux using 3N hydrochloric acid to give Compound (XXVI). The reaction time ranges from 6 to 12 hours.
(4) Next, catalytic hydrogenation may be performed on the benzoyl group using a catalyst such as palladium/activated charcoal or palladium hydroxide under a hydrogen atmosphere to give Compound (XXVII). Solvents used in this case include, for example, methanol, ethanol, isopropanol, ethyl acetate and acetic acid. Alternatively, the benzoyl group may be reduced using, e.g., triethylsilane-BF₃OEt₂, triethylsilane-trifluoroacetic acid or Ph₂SiHCl—InCl₃ (J. Org. Chem., vol. 66, p. 7741, 2001). Solvents used in this case include acetonitrile, tetrahydrofuran, dioxane, toluene, methylene chloride, 1,2-dichloroethane, chloroform and N,N-dimethylformamide. Although the reaction temperature will vary depending on the types of reagent and solvent used, it ranges from −30° C. to 100° C.

Pyrazine Compound

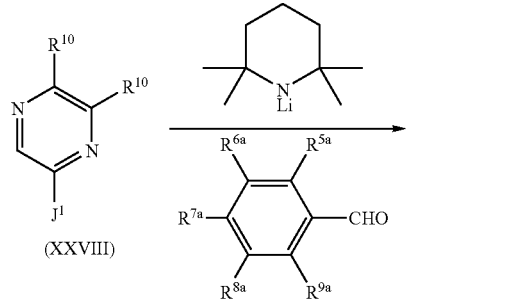

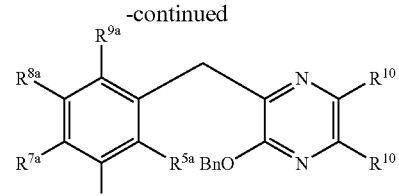

(XXX) and/or

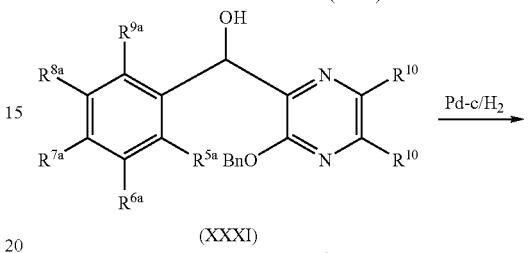

(XXXI)

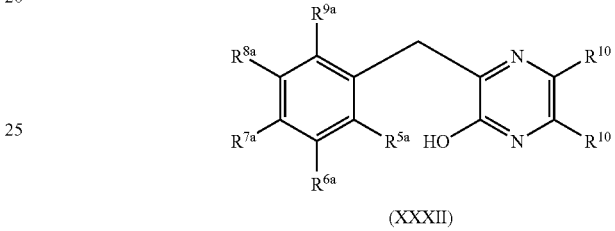

(XXXII)

(wherein the symbols are as defined above).

(1) In an appropriate solvent (e.g., diethyl ether, tetrahydrofuran), Compound (XXVIII) may be treated with LTMP at −78° C. to −20° C. and then condensed with Compound (XII) to give Compound (XXIX). The reaction temperature for condensation ranges from −78° C. to 20° C., while the reaction time ranges from 0.5 to 6 hours.
(2) Next, in an appropriate solvent (e.g., benzene, toluene), Compound (XXIX) and benzyl alcohol may be reacted in the presence of tris[2-(2-methoxyethoxy)ethyl]amine using a base (e.g., potassium hydroxide, sodium hydroxide, potassium carbonate) to give Compound (XXX) or (XXXI) or a mixture thereof. In this case, the reaction temperature ranges from room temperature to 120° C., preferably under reflux conditions.
(3) Next, catalytic hydrogenation may be performed on Compound (XXX) or (XXXI) or a mixture thereof using a catalyst such as palladium/activated charcoal or palladium hydroxide under a hydrogen atmosphere to give Compound (XXXII). Solvents used in this case include, for example, methanol, ethanol, isopropanol, ethyl acetate and acetic acid.

5-Benzyl-4-hydroxypyrimidine compound

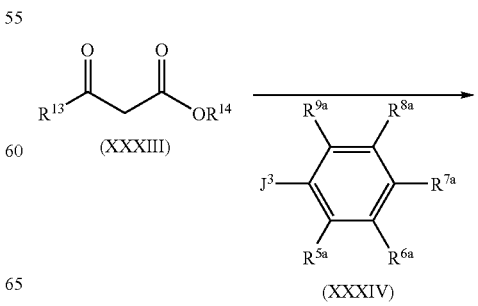

group, a tosyloxymethyl group or a formyl group, and the other symbols are as defined above).

(1) In a solvent (e.g., tetrahydrofuran, dioxane, 1,2-dimethoxyethane, N,N-dimethylformamide), Compound (XXXIII) may be condensed with Compound (XXXIV) (wherein $J^3$ is a halogen-substituted methyl group, a mesyloxymethyl group or a tosyloxymethyl group) in the presence of a base such as sodium hydride or potassium tert-butoxide to give Compound (XXXV). The reaction temperature for condensation ranges from 0° C. to 20° C. Alternatively, in a solvent (e.g., acetonitrile, tetrahydrofuran, dioxane, 1,2-dimethoxyethane, N,N-dimethylformamide), Compound (XXXIII) may also be condensed with Compound (XXXIV) (wherein $J^3$ is a formyl group) in the presence of trimethylsilyl chloride and NaI to give Compound (XXXV). The reaction temperature for condensation ranges from 0° C. to 20° C.

(2) Next, Compound (XXXV) and Compound (XXXVI) (or a hydrochloride salt thereof) may be reacted in a solvent (e.g., methanol, ethanol) in the presence or absence of NaOMe or NaOEt to give Compound (XXXVII) (see J. Chem. Soc., p. 357, 1946 or J. Prakt. Chem., vol. 342, p. 504, 2000). The reaction temperature ranges from 20° C. to reflux.

3-Hydroxypyrimidine and 4(5)-hydroxypyridazine compounds

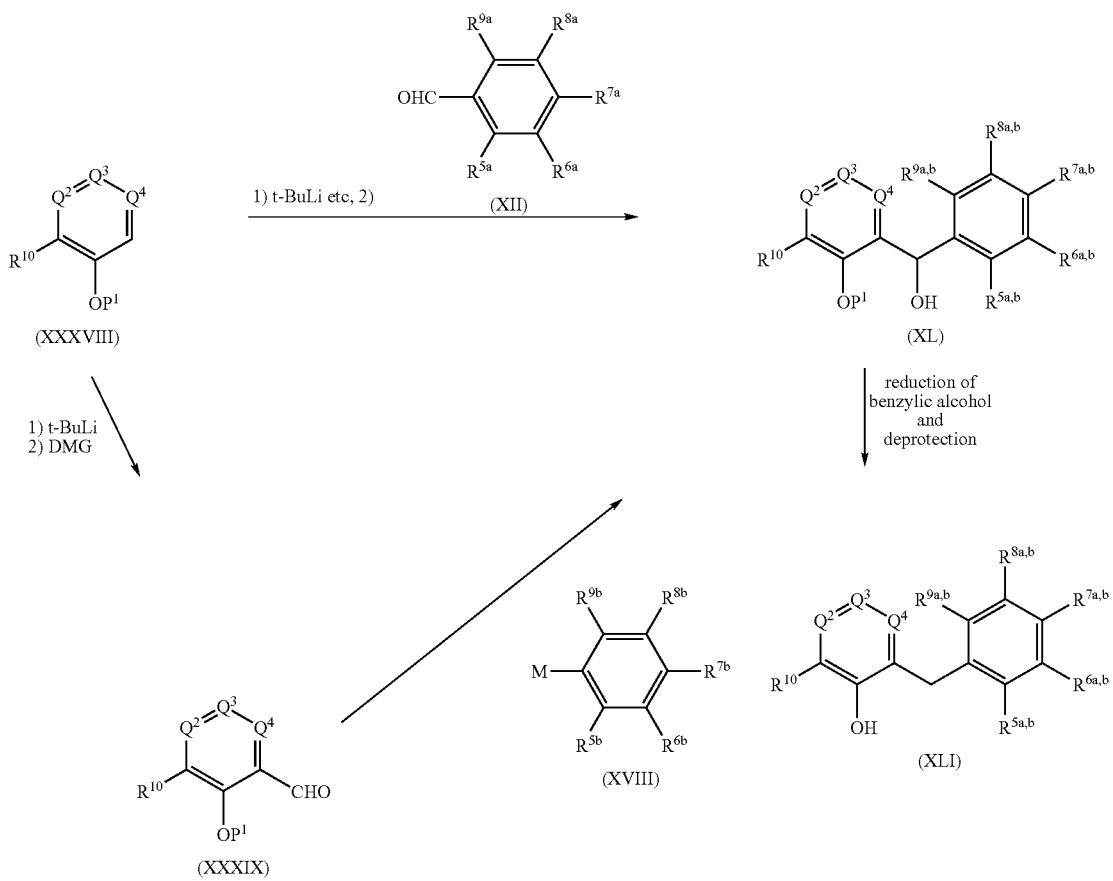

(wherein $R^{13}$ and $R^{14}$ each represent a $C_{1-6}$ alkyl group, $R^{15}$ represents a $C_{1-6}$ alkyl group, an amino group, a $C_{1-6}$ alkylamino group or an N,N-di($C_{1-6}$ alkyl)amino group, $J^3$ represents a halogen-substituted methyl group, a mesyloxymethyl

[wherein in $Q^2$ to $Q^4$, $Q^2$ and $Q^3$ or $Q^3$ and $Q^4$ each represent N and the other represents —C-$Z^{10}$, or alternatively, $Q^2$ and $Q^4$ each represent N and $Q^3$ represents —C-$Z^9$ (wherein $Z^9$ and $Z^{10}$ each represent a hydrogen atom, a $C_{1-6}$ alkyl group or a halogen atom), and the other symbols are as defined above].

(1) In an appropriate solvent (e.g., diethyl ether, tetrahydrofuran), Compound (XXXVIII) may be treated with tert-butyllithium, LDA, LTMP or mesityllithium (2,4,6-trimethylphenyllithium) at −78° C. to −20° C. and then condensed with Compound (XII) to give Compound (XL). The reaction temperature for condensation ranges from −78° C. to 20° C., while the reaction time ranges from 0.5 to 6 hours.

(1') Alternatively, in an appropriate solvent (e.g., diethyl ether, tetrahydrofuran), Compound (XXXVIII) may be treated with tert-butyllithium, LDA, LTMP or mesityllithium (2,4,6-trimethylphenyllithium) at −78° C. to −20° C., followed by addition of N,N-dimethylformamide to give Compound (XXXIX). In this case, the reaction temperature ranges from −78° C. to 20° C., preferably −78° C. to −30° C., while the reaction time ranges from 0.5 to 6 hours.

Next, in an appropriate solvent (e.g., diethyl ether, tetrahydrofuran), Compound (XXXIX) may be treated with Compound (XVIII) to give Compound (XL).

(2) In the next step, Compound (XL) may be deprotected and reduced in the same manner as shown above to prepare Compound (XLI).

The compound of the present invention allows inhibition of sodium-dependent glucose transporter 2 (SGLT2) involved in glucose reabsorption in the kidney (J. Clin. Invest., vol. 93, p. 397, 1994).

Through inhibition of SGLT2, the compound of the present invention prevents sugar reabsorption and removes excess sugar from the body to thereby treat diabetes. Thus, the compound of the present invention corrects hyperglycemia without applying any load to pancreatic β cells, and improves insulin resistance.

Thus, the present invention provides a pharmaceutical preparation for preventing or treating diseases or conditions which can be ameliorated by inhibition of SGLT2 activity, e.g., diabetes, diabetes-related diseases and diabetic complications.

As used herein, the term "diabetes" encompasses type I diabetes, type II diabetes, and other types of diabetes with specific etiology.

As used herein, the term "diabetes-related diseases" includes adiposis, hyperinsulinemia, abnormal carbohydrate metabolism, hyperlipidemia, hypercholesterolemia, hypertriglyceridemia, abnormal lipid metabolism, hypertension, congestive heart failure, edema, hyperuricemia and gout.

As used herein, the term "diabetic complications" can be classified into acute complications and chronic complications.

The term "acute complications" includes hyperglycemia (e.g., ketoacidosis), infections (e.g., skin, soft tissue, biliary system, respiratory system and urinary tract infections), etc.

The term "chronic complications" includes microangiopathy (e.g., nephropathy, retinopathy), arteriosclerosis (e.g., atherosclerosis, heart infarction, brain infarction, lower extremity arterial occlusion), neuropathy (e.g., sensory nerves, motor nerves, autonomic nerves), foot gangrene, etc.

Major complications are diabetic retinopathy, diabetic nephropathy and diabetic neuropathy.

The compound of the present invention may also be used in combination with any therapeutic agent for diabetes, diabetic complications, hyperlipidemia or hypertension, which depends on a different mechanism of action other than inhibition of SGLT2 activity. When combined with other drugs, the compound of the present invention can be expected to produce an additive effect on these diseases, which is greater than either one alone.

Examples of a "therapeutic agent for diabetes or diabetic complications" available for combination use include, for example, insulin sensitizers (e.g., PPARγ agonists, PPARα/γ agonists, PPARδ agonists, PPARα/γ/δ agonists), glycosidase inhibitors, biguanides, insulin secretagogues, insulin formulations, glucagon receptor antagonists, insulin receptor kinase stimulators, tripeptidyl peptidase II inhibitors, dipeptidyl peptidase IV inhibitors, protein tyrosine phosphatase-1B inhibitors, glycogen phosphorylase inhibitors, glucose-6-phosphatase inhibitors, gluconeogenesis inhibitors, fructose-bisphosphatase inhibitors, pyruvate dehydrogenase inhibitors, glucokinase activators, D-chiroinositol, glycogen synthase kinase-3 inhibitors, glucagon-like peptide-1, glucagon-like peptide-1 analogs, glucagon-like peptide-1 agonists, amylin, amylin analogs, amylin agonists, glucocorticoid receptor antagonists, 11β-hydroxysteroid dehydrogenase inhibitors, aldose reductase inhibitors, protein kinase C inhibitors, γ-aminobutyric acid receptor antagonists, sodium channel antagonists, transcription factor NF-κB inhibitors, IKKβ inhibitors, lipid peroxidase inhibitors, N-acetylated-α-linked-acid-dipeptidase inhibitors, insulin-like growth factor-I, platelet-derived growth factors (PDGF), platelet-derived growth factor (PDGF) analogs, epidermal growth factors (EGF), nerve growth factors, carnitine derivatives, uridine, 5-hydroxy-1-methylhydantoin, EGB-761, bimoclomol, sulodexide, Y-128 and TAK-428.

Illustrative examples of a therapeutic agent for diabetes or diabetic complications are as follows.

"Biguanides" include metformin hydrochloride and phenformin.

"Insulin secretagogues" include those of the sulfonylurea type such as glyburide (glibenclamide), glypizide, gliclazide and chlorpropamide, as well as those of the non-sulfonylurea type such as nateglinide, repaglinide and mitiglinide.

"Insulin formulations" encompass both recombinantly produced human insulin and animal-derived, insulin. Such formulations can be divided into three groups depending on the length of their duration: fast-acting formulations (e.g., human insulin, human neutral insulin); intermediate-acting formulations (e.g., insulin-human isophane insulin aqueous suspension, human neutral insulin-human isophane insulin aqueous suspension, human insulin zinc aqueous suspension, insulin zinc aqueous suspension); and long-acting formulations (e.g., human crystalline insulin zinc suspension).

"Glycosidase inhibitors" include acarbose, voglibose and miglitol.

"Insulin sensitizers" include PPARγ agonists such as troglitazone, pioglitazone and rosiglitazone, PPARα/γ dual agonists such as MK-767 (KRP-297), tesaglitazar, LM4156, LY510929, DRF-4823 and TY-51501, as well as PPARδ agonists such as GW-501516.

"Tripeptidyl peptidase II inhibitors" include UCL-139.

"Dipeptidyl peptidase IV inhibitors" include NVP-DPP728A, LAF-237, P32/98 and TSL-225.

"Aldose reductase inhibitors" include ascorbyl gamolenate, tolrestat, epalrestat, fidarestat, sorbinil, ponalrestat, risarestat and zenarestat.

"γ-Aminobutyric acid receptor antagonists" include topiramate.

"Sodium channel antagonists" include mexiletine hydrochloride.

"Transcription factor NF-κB inhibitors" include dexlipotam.

"Lipid peroxidase inhibitors" include tirilazad mesylate.

"N-Acetylated-α-linked-acid-dipeptidase inhibitors" include GPI-5693.

"Carnitine derivatives" include carnitine and levacecamine hydrochloride.

Examples of a "therapeutic agent for hyperlipidemia or hypertension" available for combination use include, for example, hydroxymethylglutaryl coenzyme A reductase inhibitors, fibrates, $β_3$-adrenergic receptor agonists, AMPK activators, acyl-coenzyme A:cholesterol acyltransferase inhibitors, probucol, thyroid hormone receptor agonists, cholesterol absorption inhibitors, lipase inhibitors, microsomal triglyceride transfer protein inhibitors, lipoxygenase inhibitors, carnitine palmitoyl transferase inhibitors, squalene synthase inhibitors, low-density lipoprotein receptor promoters, nicotinic acid derivatives, bile acid binding resins, sodium-dependent bile acid transporter inhibitors, cholesterol ester transport protein inhibitors, angiotensin-converting enzyme inhibitors, angiotensin II receptor antagonists, endothelin-converting enzyme inhibitors, endothelin receptor antagonists, diuretics, calcium antagonists, vasodilator antihypertensives, sympatholytic agents, central-acting antihypertensives, $α_2$-adrenergic receptor agonists, antiplatelet agents, uric acid production inhibitors, uric acid excretion stimulators, urine alkalizers, anorectics, AGE inhibitors, adiponectin receptor agonists, $GPR^{40}$ agonists and $GPR^{40}$ antagonists.

Illustrative examples of a therapeutic agent for hyperlipidemia or hypertension are as follows.

"Hydroxymethylglutaryl coenzyme A reductase inhibitors" include fluvastatin, lovastatin, pravastatin, cerivastatin and pitavastatin.

"Fibrates" include bezafibrate, beclobrate and binifibrate.

"Squalene synthase inhibitors" include TAK-475 and α-phosphonosulfonate derivatives (U.S. Pat. No. 5,712,396).

"Acyl-coenzyme A: cholesterol acyltransferase inhibitors" include CI-1011, NTE-122, FCE-27677, RP-73163, MCC-147 and DPU-129.

"Low-density lipoprotein receptor promoters" include MD-700 and LY-295427.

"Microsomal triglyceride transfer protein inhibitors (MTP inhibitors)" include compounds as described in, e.g., U.S. Pat. No. 5,739,135, U.S. Pat. No. 5,712,279 and U.S. Pat. No. 5,760,246.

"Anorectics" include adrenaline/noradrenaline agonists (e.g., mazindol, ephedrine), serotonin agonists (selective serotonin reuptake inhibitors such as fluvoxamine), adrenaline/serotonin agonists (e.g., sibutramine), melanocortin 4 receptor (MC4R) agonists, α-melanocyte-concentrating hormones (α-MCH), leptin, as well as cocaine- and amphetamine-regulated transcripts (CART).

"Thyroid hormone receptor agonists" include liothyronine sodium and levothyroxine sodium.

"Cholesterol absorption inhibitors" include ezetimibe.

"Lipase inhibitors" include orlistat.

"Carnitine palmitoyl transferase inhibitors" include etomoxir.

"Nicotinic acid derivatives" include nicotinic acid, nicotinamide, nicomol and nicorandil.

"Bile acid binding resins" include cholestyramine, colestilan and colesevelam hydrochloride.

"Angiotensin-converting enzyme inhibitors" include captoril, enalapril maleate, alacepril and cilazapril.

"Angiotensin II receptor antagonists" include candesartan cilexetil, losartan potassium and eprosartan mesylate.

"Endothelin-converting enzyme inhibitors" include CGS-31447 and CGS-35066.

"Endothelin receptor antagonists" include L-749805, TBC-3214 and BMS-182874.

By way of example, in treating diabetes or the like, it would be preferable to use the compound of the present invention in combination with at least one drug selected from the group consisting of an insulin sensitizer (e.g., a PPARγ agonist, a PPARα/γ agonist, a PPARδ agonist, a PPARα/γ/δ agonist), a glycosidase inhibitor, a biguanide, an insulin secretagogue, an insulin formulation and a dipeptidyl peptidase IV inhibitor.

Alternatively, it would be preferable to use the compound of the present invention in combination with at least one drug selected from the group consisting of a hydroxymethylglutaryl coenzyme A reductase inhibitor, a fibrate, a squalene synthase inhibitor, an acyl-coenzyme A:cholesterol acyltransferase inhibitor, a low-density lipoprotein receptor promoter, a microsomal triglyceride transfer protein inhibitor and an anorectic.

The pharmaceutical preparation of the present invention can be administered systemically or topically via oral route or parenteral (e.g., intrarectal, subcutaneous, intramuscular, intravenous, percutaneous) route.

For use as a pharmaceutical preparation, the compound of the present invention may be formulated into any desired dosage form selected from solid compositions, liquid compositions and other compositions, as appropriate for the intended purpose. The pharmaceutical preparation of the present invention can be prepared by blending the compound of the present invention with pharmaceutically acceptable carrier(s). More specifically, the compound of the present invention may be supplemented with commonly used excipients, extenders, binders, disintegrating agents, coating agents, sugar-coating agents, pH regulators, solubilizers, aqueous or non-aqueous solvents and so on, and then formulated using standard techniques into tablets, pills, capsules, granules, powders, solutions, emulsions, suspensions, injections, etc. Examples of excipients and extenders include, for example, lactose, magnesium stearate, starch, talc, gelatin, agar, pectin, gum arabic, olive oil, sesame oil, cacao butter, ethylene glycol and other commonly used materials.

Also, the compound of the present invention may be modified to form an inclusion compound with, e.g., α-, β- or γ-cyclodextrin or methylated cyclodextrin before being formulated.

The dose of the compound of present invention will vary depending on the disease or symptom to be treated, body weight, age, sex, the route of administration, etc. The adult dose is preferably 0.1 to 1000 mg/kg body weight/day, more preferably 0.1 to 200 mg/kg body weight/day, given as a single dose or in divided doses.

REFERENCE EXAMPLES

Preparation of intermediates required to prepare the compounds of the present invention will be illustrated below with reference to the following reference examples.

Reference Example 1

Preparation of 4-(4-ethylbenzyl)-3-hydroxy-1-isopropyl-5-methyl-1H-pyrazole

To a solution of 1,2-dihydro-4-(4-ethylbenzyl)-5-methyl-3H-pyrazol-3-one (synthesized as described in WO0116147; 1.0 g, 4.6 mmol), benzyl alcohol (600 mg, 5.5 mmol) and triphenylphosphine (1.46 g, 5.5 mmol) in tetrahydrofuran (30 mL), diethyl azodicarboxylate (40% in toluene, 5.1 mmol) was added dropwise under ice cooling. After stirring overnight at room temperature, the reaction mixture was concentrated and the resulting residue was purified by silica gel column chromatography (hexane:ethyl acetate=75:25 to 70:30) to give 3-benzyloxy-4-(4-ethylbenzyl)-5-methyl-1H-pyrazole (550 mg, 39%) as a colorless powder.

$^1$H-NMR (300 MHz, CDCl$_3$): δ 1.21 (t, J=7.6 Hz, 3H), 2.11 (s, 3H), 2.60 (q, J=7.6 Hz, 2H), 3.66 (s, 2H), 5.24 (s, 2H), 7.03-7.15 (m, 4H).

ESI m/z=307(M+H).

mp 80.0-83.0° C.

To a suspension of the thus obtained 3-benzyloxy-4-(4-ethylbenzyl)-5-methyl-1H-pyrazole (200 mg, 0.65 mmol) and cesium carbonate (1.06 g, 3.25 mmol) in N,N-dimethylformamide (4 mL), isopropyl iodide (350 mg, 2.06 mmol) was added dropwise at room temperature. After stirring at room temperature for 13 hours, additional cesium carbonate (1.06 g, 3.25 mmol) and isopropyl iodide (350 mg, 2.06 mmol) were added. After stirring at room temperature for an additional 3 hours, the reaction mixture was diluted with water and extracted with ethyl acetate. The resulting organic layer was washed with saturated aqueous sodium chloride and dried over anhydrous magnesium sulfate. After the solvent was distilled off under reduced pressure, the resulting residue was purified by silica gel column chromatography (hexane:ethyl acetate=10:1) to give 3-benzyloxy-4-(4-ethylbenzyl)-1-isopropyl-5-methyl-1H-pyrazole (179 mg, 79%) as a light-brown oil.

$^1$H-NMR (300 MHz, CDCl$_3$): δ 1.20 (t, J=7.6 Hz, 3H), 1.39 (d, J=6.5 Hz, 6H), 2.17 (s, 3H), 2.59 (q, J=7.6 Hz, 2H), 3.62 (s, 2H), 4.20-4.32 (m, 1H), 5.23 (s, 2H), 7.00-7.12 (m, 4H), 7.22-7.42 (m, 5H).

ESI m/z=371(M+Na)

To a solution of the thus obtained 3-benzyloxy-4-(4-ethylbenzyl)-1-isopropyl-5-methyl-1H-pyrazole (160 mg, 0.46 mmol) in methanol (3 mL), 20% palladium hydroxide/carbon (58 mg) was added at room temperature and stirred overnight under a hydrogen atmosphere at room temperature. After filtration to remove the insoluble materials, the solvent was distilled off under reduced pressure to give 4-(4-ethylbenzyl)-3-hydroxy-1-isopropyl-5-methyl-1H-pyrazole (109 mg, 92%) as a colorless powder.

$^1$H-NMR (300 MHz, CDCl$_3$): δ 1.21 (t, J=7.6 Hz, 3H), 1.39 (d, J=6.7 Hz, 6H), 2.07 (s, 3H), 2.60 (q, J=7.6 Hz, 2H), 3.66 (s, 2H), 4.19-4.30 (m, 1H), 7.07 (d, J=8.0 Hz, 2H), 7.17 (d, J=8.0 Hz, 2H).

ESI m/z=257(M−H).

mp 164.0-169.0° C.

Reference Example 2

Preparation of 1-acetyl-4-[(3-fluoro-4-methoxyphenyl)methyl]-3-hydroxy-5-methyl-1H-pyrazole A mixture of 1,2-dihydro-4-[(3-fluoro-4-methoxyphenyl)methyl]-5-methyl-3H-pyrazol-3-one (synthesized as described in WO0236602; 4.11 g, 0.0174 mol), acetic anhydride (41 mL) and acetic acid (41 mL) was stirred at 135° C. for 8 hours and at room temperature for 12 hours. After being concentrated, the reaction mixture was diluted with toluene and then concentrated again. To the resulting residue, methanol (400 mL) and a 25 wt % methanol solution of sodium methoxide (0.37 mL) were added and stirred for 20 hours. The reaction mixture was concentrated and the resulting residue was purified by silica gel column chromatography (hexane:ethyl acetate=4:1 to 1:1) to give 1-acetyl-4-[(3-fluoro-4-methoxyphenyl)methyl]-3-hydroxy-5-methyl-1H-pyrazole (960 mg, 20%) as a colorless powder.

$^1$H-NMR (300 MHz, CDCl$_3$): δ 2.50 (s, 3H), 2.51 (s, 3H), 3.61 (s, 2H), 3.85 (s, 3H), 6.80-6.99 (m, 3H).

Reference Example 3

Preparation of 1-cyclobutyl-4-(4-ethylbenzyl)-3-hydroxy-5-trifluoromethyl-1H-pyrazole To a mixture of 4-(4-ethylbenzyl)-3-O-t-butyldimethylsilyl-5-trifluoromethyl-1H-pyrazole (synthesized as described in WO02088157; 110 mg, 0.286 mmol), cyclobutanol (45 μL, 0.572 mmol), triphenylphosphine (135 mg, 0.515 mmol) and tetrahydrofuran (0.8 mL), diisopropyl azodicarboxylate (40% in toluene, 0.305 mL, 0.572 mmol) was slowly added dropwise at 0° C. After stirring at room temperature for 20 hours, the reaction mixture was concentrated and the resulting residue was purified by silica gel column chromatography (hexane:ethyl acetate=95:5) to give 1-cyclobutyl-4-(4-ethylbenzyl)-3-O-t-butyldimethylsilyl-5-trifluoromethyl-1H-pyrazole (80 mg, 64%).

Next, to a solution of the thus obtained 1-cyclobutyl-4-(4-ethylbenzyl)-3-O-t-butyldimethylsilyl-5-trifluoromethyl-1H-pyrazole (80 mg, 0.182 mmol) in tetrahydrofuran (1.0 mL), a 1 mol/L tetrahydrofuran solution of tetrabutylammonium fluoride (0.2 mL) was added. After stirring at room temperature for 30 minutes, the reaction mixture was concentrated and the resulting residue was purified by silica gel column chromatography (hexane:ethyl acetate=95:5 to 4:1 to 1:1) to give the titled compound (29 mg, 31%) as a colorless crystal.

$^1$H-NMR (300 MHz, CDCl$_3$): δ 1.20 (t, J=7.6 Hz, 3H), 1.69-1.90 (m, 2H), 2.30-2.40 (m, 2H), 2.54-2.68 (m, 4H), 3.80 (s, 2H), 4.72 (quint, J=8.0 Hz, 1H), 7.08 (d, J=8.1 Hz, 2H), 7.18 (d, J=8.1 Hz, 2H), 10.97 (brs, 1H).

Reference Example 4

Preparation of 4-[(2-benzyloxyphenyl)methyl]-1,2-dihydro-5-isopropyl-3H-pyrazol-3-one To a solution of 2-benzyloxybenzaldehyde (2.0 g) in methanol (20 mL), NaBH$_4$ (356 mg, 9.42 mmol) was added under ice cooling and stirred for 1 hour. After addition of additional NaBH$_4$ (49 mg), the reaction mixture was stirred at room temperature for 1.5 hours. The reaction mixture was concentrated and water was added to the resulting residue, followed by extracting the mixture with ethyl acetate. The organic layer was washed with saturated aqueous sodium chloride and dried over anhydrous magnesium sulfate. The solvent was distilled off under reduced pressure to give 2-benzyloxybenzyl alcohol (2.1 g) as a colorless oil.

To a solution of 2-benzyloxybenzyl alcohol (2.1 g, 9.42 mmol) in tetrahydrofuran (10 mL), triethylamine (1.38 mL, 9.89 mmol) and methanesulfonyl chloride (0.766 mL, 9.89 mmol) were added under ice cooling and stirred at room temperature for 30 minutes. After filtration to remove the insoluble materials, the filtrate was concentrated to give (2-benzyloxyphenyl)methyl mesylate (3.24 g). To a suspension of methyl isobutyrylacetate (1.43 g, 9.89 mmol), sodium hydride (60% in oil; 396 mg, 9.89 mmol) and dimethoxyethane (10 mL), a solution of (2-benzyloxyphenyl)methyl mesylate (3.24 g) in dimethoxyethane (10 mL) was added and stirred at 70° C. overnight. After addition of 0.5 M HCl, the reaction mixture was extracted twice with ethyl acetate. The combined organic layers were washed with saturated aqueous sodium chloride and dried over anhydrous magnesium sulfate. The solvent was distilled off under reduced pressure to give an oil. To this oil, toluene (20 mL) and hydrazine monohydrate (317 mg, 9.89 mmol) were added and the resulting mixture was heated under reflux for 3 hours. After cooling to room temperature, the reaction mixture was diluted with ethyl acetate, washed with water and dried over anhydrous magnesium sulfate. The reaction mixture was concentrated and the resulting residue was purified by silica gel column chromatography (chloroform:methanol=50:1 to 8:1) to give the titled compound (750 mg, 25%) as a light-yellow amorphous substance.

$^1$H-NMR (200 MHz, CDCl$_3$): δ 1.08 (d, J=7.5 Hz, 6H), 2.93 (quint, J=7.5 Hz, 1H), 3.75 (s, 2H), 5.12 (s, 2H), 6.82-6.95 (m, 2H), 7.09-7.19 (m, 2H), 7.31-7.50 (m, 5H).

ESI m/z=345(M+Na).

Reference Example 5

Preparation of 1-(4-methylphenyl)-4-(4-ethylbenzyl)-3-hydroxy-5-methyl-1H-pyrazole To a solution of 4-(4-ethylbenzyl)-3-O-t-butyldimethylsilyl-5-methyl-1H-pyrazole (249 mg, 0.753 mmol) in chloroform (5 mL), 4-methylphenylboronic acid (205 mg, 1.51 mmol) and Cu(OAc)$_2$ (208 mg, 1.15 mmol) were added together with molecular sieves 4A (750 mg) and pyridine (0.122 mL, 1.51 mmol). The reaction mixture was stirred at room temperature for 15 hours and the insoluble materials were filtered off. The filtrate was concentrated and the resulting residue was purified by silica gel column chromatography (hexane:ethyl acetate=20:1 to 10:1) to give 4-(4-ethylbenzyl)-3-O-t-butyldimethylsilyl-5-methyl-1-(4-methylphenyl)-1H-pyrazole (50 mg, 16%). Next, to a solution of 4-(4-ethylbenzyl)-3-O-t-butyldimethylsilyl-5-methyl-1-(4-methylphenyl)-1H-pyrazole (50 mg, 0.158 mmol) in tetrahydrofuran (1.0 mL), a 1 mol/L tetrahydrofuran solution of tetrabutylammonium fluoride (0.2 mL) was added. After stirring at room temperature for 1 hour, the reaction mixture was concentrated and the resulting residue was purified by silica gel column chromatography (hexane:ethyl acetate=1:1) to give the titled compound (31 mg, 64%) as a colorless crystal.

$^1$H-NMR (300 MHz, CDCl$_3$): δ 1.21 (d, J=7.6 Hz, 3H), 2.13 (s, 3H), 2.38 (s, 3H), 2.61 (q, J=7.6 Hz, 1H), 3.29 (s, 2H), 7.09 (d, J=8.2 Hz, 2H), 7.18 (d, J=8.2 Hz, 2H), 7.22-7.25 (m, 4H).

ESI m/z=329(M+Na).

Reference Example 6

Preparation of 4-(4-ethylbenzyl)-3-hydroxypyridine

Sodium hydride (5.55 g, 139 mmol) was washed with hexane and then mixed with dimethoxyethane (200 ml). To the resulting mixture, 3-hydroxypyridine (12.0 g, 126 mmol) was added over 10 minutes under ice cooling. After stirring for 10 minutes, 2-(trimethylsilyl)ethoxymethyl chloride (25.2 g, 151 mmol) was added over 25 minutes under ice cooling. After stirring at room temperature for 14.5 hours, the reaction mixture was diluted with water under ice cooling and extracted with ether. The organic layer was dried over anhydrous magnesium sulfate and concentrated under reduced pressure. The resulting residue was purified by silica gel column chromatography (hexane:ethyl acetate=67:33) to give 3-[2-(trimethylsilyl)ethoxymethoxy]pyridine (23.9 g, 84%) as a brown oil.

CI m/z=226(M+).

Next, to a mixture of 3-[2-(trimethylsilyl)ethoxymethoxy]pyridine (23.0 g, 102 mmol) and tetrahydrofuran (400 ml), a 1.47 mol/L t-butyllithium n-pentane solution (80 ml, 118 mmol) was added dropwise at −70° C. over 25 minutes. After stirring at −70° C. for 1 hour, an ether solution of 4-ethylbenzaldehyde (17.7 g, 132 mmol) was added over 25 minutes. The reaction mixture was stirred at −70° C. for 2 hours and at room temperature for 2 hours. After warming to room temperature, the reaction mixture was poured into saturated aqueous ammonium chloride and extracted with ether. The organic layer was dried over anhydrous magnesium sulfate and concentrated under reduced pressure. The resulting residue was purified by silica gel column chromatography (hexane:ethyl acetate=50:50) to give (4-ethylphenyl)-[3-[2-(trimethylsilyl)ethoxymethoxy]pyridin-4-yl]-methanol (20.1 g, 55%) as a light-yellow powder.

ESI m/z=382(M+Na).

Next, to a mixture of (4-ethylphenyl)-[3-[2-(trimethylsilyl)ethoxymethoxy]pyridin-4-yl]-methanol (20 g, 55.6 mmol), tetrahydrofuran (500 ml) and water (20 ml), p-toluenesulfonic acid monohydrate (26.3 g, 138 mmol) was added. After stirring at 50° C. for 4 hours, at room temperature for 15.5 hours and at 50° C. for 3 hours, the reaction mixture was neutralized with saturated aqueous sodium bicarbonate and extracted three times with chloroform. The combined organic layers were dried over anhydrous magnesium sulfate and concentrated under reduced pressure. The resulting residue was purified by silica gel column chromatography (chloroform:methanol=10:1) to give (4-ethylphenyl)-(3-hydroxypyridin-4-yl)-methanol (10.9 g, 86%) as a light-yellow amorphous substance.

ESI m/z=230(M+H).

Next, to a mixture of (4-ethylphenyl)-(3-hydroxypyridin-4-yl)-methanol (10.54 g, 46.0 mmol) and acetic acid (100 ml), 5% palladium/carbon (5.0 g) was added and stirred under a hydrogen atmosphere at room temperature for 7 hours. After filtration to remove the insoluble materials, the filtrate was concentrated under reduced pressure and the resulting residue was recrystallized (ethyl acetate) to give the titled compound (3.91 g, 40%) as a colorless powder. Moreover, the mother liquor was purified by NH silica gel column chromatography (chloroform:methanol=20:1) to give 4-(4-ethylbenzyl)-3-hydroxypyridine (4.55 g, 46%) as a light-brown powder.

ESI m/z=214(M+Na).

Reference Example 7

Preparation of 4-(4-ethylbenzyl)-3-hydroxypyridinium borane

To a suspension of 4-(4-ethylbenzyl)-3-hydroxypyridine (300 mg, 1.41 mmol) and tetrahydrofuran (1.5 mL), 1M borane-tetrahydrofuran complex (7.2 mL, 7.2 mmol) was added at 0° C. under a nitrogen atmosphere and stirred at room temperature for 1 hour. Methanol (1 mL) was carefully added to the reaction mixture, followed by stirring at room temperature for 1 hour. After addition of ethyl acetate, the reaction mixture was washed with aqueous sodium chloride and dried over anhydrous magnesium sulfate. After concentration under reduced pressure, the resulting residue was purified by silica gel column chromatography (hexane:ethyl acetate=50:50) to give the titled compound (200 mg, 62%) as a colorless powder.

$^1$H-NMR (200 MHz, CDCl$_3$): δ 1.23 (t, J=7.6 Hz, 3H), 2.64 (q, J=7.6 Hz, 2H), 4.00 (s, 2H), 7.09-7.19 (m, 5H), 8.04 (d, J=5.7 Hz, 1H), 8.15 (s, 1H).

ESI m/z=250(M+Na), 226(M−H).

Reference Example 8

Preparation of 4-(4-cyclopropylbenzyl)-3-hydroxypyridine

To a solution of 3-[2-(trimethylsilyl)ethoxymethoxy]pyridine (39.3 g, 0.174 mol) in tetrahydrofuran (250 ml), a 1.47 mol/L t-butyllithium n-pentane solution (154 ml, 0.227 mol) was added dropwise at −70° C. over 40 minutes. After stirring at −70° C. for 1 hour, N,N-dimethylformamide (40 mL, 0.522 mol) was added over 30 minutes and stirred at −70° C. for 1.5 hours. After warming to −20° C., saturated aqueous ammonium chloride was added to the reaction mixture, which was then extracted twice with ethyl acetate. The organic layers were dried over anhydrous magnesium sulfate and concentrated under reduced pressure. The resulting residue was purified by silica gel column chromatography (hexane:ethyl acetate=80:20) to give 4-formyl-3-[2-(trimethylsilyl)ethoxymethoxy]pyridine (24.5 g, 58%) as a brown oil.

To a solution of 4-cyclopropylbromobenzene (synthesized as described in WO0268439; 2.5 g, 0.0127 mol) in tetrahydrofuran (20 ml), a 1.58 mol/L n-butyllithium/n-hexane solution (8.4 ml, 0.0133 mol) was added dropwise at −70° C. over 8 minutes. After stirring at −70° C. for 1 hour, a tetrahydrofuran solution of 4-formyl-3-[2-(trimethylsilyl)ethoxymethoxy]pyridine (4.2 g, 0.0165 mol) was added over 5 minutes and stirred at −70° C. for 2.5 hours. After addition of saturated aqueous ammonium chloride, the reaction mixture was warmed to room temperature and extracted twice with ethyl acetate. The organic layers were dried over anhydrous magnesium sulfate and concentrated under reduced pressure. The resulting residue was purified by silica gel column chromatography (hexane:ethyl acetate=50:50) to give (4-cyclopropylphenyl)-[3-[2-(trimethylsilyl)ethoxymethoxy]pyridin-4-yl]-methanol (2.5 g, 53%) as a brown solid.

Next, to a solution of (4-cyclopropylphenyl)-[3-[2-(trimethylsilyl)ethoxymethoxy]pyridin-4-yl]-methanol (2.4 g, 6.46 mmol) in chloroform (34 mL), Dess-Martin Periodine (3.0 g, 7.10 mmol.) was added and stirred at room temperature for 1.5 hours. After addition of additional Dess-Martin Periodine (0.3 g, 0.710 mmol.), the reaction mixture was stirred for 1.5 hours. After filtration to remove the insoluble materials, the filtrate was washed with saturated aqueous sodium bicarbonate and saturated aqueous sodium chloride and then dried over anhydrous magnesium sulfate. The solvent was distilled off under reduced pressure and the resulting residue was purified by NH silica gel column chromatography (hexane:ethyl acetate=50:50) to give 4-(4-cyclopropylbenzoyl)-3-[2-(trimethylsilyl)ethoxymethoxy]pyridine (2.25 g, 94%). Next, to a solution of 4-(4-cyclopropylbenzoyl)-3-[2-(trimethylsilyl)ethoxymethoxy]pyridine (2.25 g, 6.06 mmol) in tetrahydrofuran (56 mL), p-toluenesulfonic acid monohydrate (3.46 g, 18.2 mmol) was added and stirred at 65° C. for 1 hour. After cooling to room temperature, the reaction mixture was poured into saturated aqueous sodium bicarbonate and extracted twice with ethyl acetate. The organic layers were dried over anhydrous magnesium sulfate and concentrated under reduced pressure to give 4-(4-cyclopropylbenzoyl)-3-hydroxypyridine (1.97 g) as a yellow oil. Subsequently, to 4-(4-cyclopropylbenzoyl)-3-hydroxypyridine (1.97 g) in tetrahydrofuran (20 mL), triethylamine (1.69 mL, 12.1 mmol) and methyl chloroformate (859 mg, 9.09 mmol) were added and stirred at room temperature for 30 minutes. Saturated aqueous sodium bicarbonate was poured into the reaction mixture, which was then extracted twice with ethyl acetate. The organic layers were dried over anhydrous magnesium sulfate and concentrated under reduced pressure to give 4-(4-cyclopropylbenzoyl)-3-methoxycarbonyloxypyridine (2.22 g) as a brown oil. Next, to a solution of 4-(4-cyclopropylbenzoyl)-3-methoxycarbonyloxypyridine (2.22 g) in tetrahydrofuran (40 mL)-water (20 mL), NaBH$_4$ (1.38 g, 36.4 mmol) was added under ice cooling and stirred at room temperature for 36 hours. The reaction mixture was adjusted with 1M hydrochloric acid to pH 8.0 and then extracted twice with ethyl acetate. The organic layers were washed with saturated aqueous sodium chloride and dried over anhydrous magnesium sulfate. After the solvent was distilled off under reduced pressure, the resulting residue was purified by silica gel column chromatography (hexane:ethyl acetate=50:50) to give 4-(4-cyclopropylbenzyl)-3-hydroxypyridine (270 mg).

ESI m/z=248(M+Na).

Reference Example 9

Preparation of 4-(4-methoxycarbonylbenzyl)-3-hydroxypyridine

To a mixture of 3-hydroxypyridine (50.0 g, 0.525 mol), tetrahydrofuran (107 mL) and N,N-dimethylformamide (285 mL), potassium t-butoxide (65 g, 0.579 mol) was added at −15° C. After 25 minutes, chloromethyl methyl ether (44.4 g, 0.552 mol) was slowly added at −15° C. The reaction temperature was elevated over 2 hours and the reaction mixture was concentrated. The resulting oil was poured into saturated aqueous sodium chloride and extracted with ethyl acetate. The organic layer was dried over anhydrous magnesium sulfate and concentrated under reduced pressure. The resulting residue was purified by silica gel column chromatography (hexane:ethyl acetate=50:50) to give 3-(methoxymethoxy)pyridine (54.7 g, 75%).

Next, to a mixture of 3-(methoxymethoxy)pyridine (10.0 g, 71.9 mmol) and diethyl ether (1000 ml), a 1.47 mol/L t-butyllithium n-pentane solution (62 ml, 86.2 mmol) was added dropwise at −70° C. over 25 minutes. After stirring at −70° C. for 1 hour, a solution of 4-methoxycarbonylbenzaldehyde (14.0 g, 90.5 mmol) in diethyl ether (80 mL) was added over 30 minutes and stirred at −70° C. for 1.5 hours. After warming to room temperature, the reaction mixture was poured into saturated aqueous ammonium chloride and extracted with ethyl acetate. The organic layer was washed with saturated aqueous sodium chloride, dried over anhydrous magnesium sulfate, and concentrated under reduced pressure. The resulting residue was purified by silica gel column chromatography (hexane:ethyl acetate=20:80) to give (4-methoxycarbonylphenyl)-[3-(methoxymethoxy)pyridin-4-yl]-methanol (2.06 g, 9.4%) as a yellow powder.

Next, a mixture of (4-methoxycarbonylphenyl)-[3-(methoxymethoxy)pyridin-4-yl]-methanol (2.06 g, 6.79 mmol), methanol (35 mL) and concentrated hydrochloric acid (4.4 mL) was heated under reflux for 20 minutes. After cooling to room temperature, the reaction mixture was concentrated. Methanol and ethyl acetate were added to the residue and the resulting precipitate was filtered to give (4-methoxycarbonylphenyl)-(3-hydroxypyridin-4-yl)-methanol hydrochloride (1.87 g, 81%).

Next, a mixture of (4-methoxycarbonylphenyl)-(3-hydroxypyridin-4-yl)-methanol hydrochloride (1.87 g, 5.50 mmol), methanol (50 ml) and 10% palladium/carbon (0.94 g) was stirred under a hydrogen atmosphere at room temperature for 3 days. After filtration to remove the insoluble materials, the filtrate was concentrated under reduced pressure and the resulting residue was poured into saturated aqueous NaHCO$_3$ and extracted with ethyl acetate. The organic layer was washed with saturated aqueous sodium chloride, dried over anhydrous magnesium sulfate, and concentrated under reduced pressure. The resulting crystal was recrystallized from diethyl ether to give the titled compound (1.27 g, 95%).

ESI m/z=266(M+Na).

Reference Example 10

Preparation of 4-[4-(2-benzoyloxyethyl)benzyl]-3-hydroxypyridine

To a mixture of 4-bromophenylethyl alcohol (12 g, 59.7 mmol), ethyldiisopropylamine (11.5 g, 89.5 mmol) and chloroform (200 mL), chloromethyl methyl ether (7.2 g, 89.5 mmol) was slowly added at 0° C. The reaction mixture was stirred at 0° C. for 1 hour and at room temperature for 2.5 hours, and then poured into water. After the mixture was extracted twice with chloroform, the combined organic layers were washed with saturated aqueous sodium chloride, dried over anhydrous magnesium sulfate and concentrated under reduced pressure to give bromo-4-(2-methoxymethoxyethyl)benzene (15.1 g).

Next, to a mixture of bromo-4-(2-methoxymethoxyethyl)benzene (12.0 g, 49.0 mmol) and tetrahydrofuran (75 ml), a 1.58 mol/L n-butyllithium n-hexane solution (34 ml, 53.7 mmol) was added dropwise at −78° C. over 10 minutes. After stirring at −78° C. for 1 hour, a solution of N,N-dimethylformamide (11.4 mL, 147 mmol) in tetrahydrofuran (5 mL) was added and stirred at −78° C. for 1.5 hours. After warming to room temperature, the reaction mixture was poured into saturated aqueous ammonium chloride and extracted with ethyl acetate. The organic layer was washed with saturated aqueous sodium chloride and dried over anhydrous magnesium sulfate. After concentration, the resulting residue was purified by silica gel column chromatography (hexane:ethyl acetate=80:20) to give 4-(2-methoxymethoxyethyl)benzaldehyde (7.0 g, 74%).

Next, a mixture of 4-(2-methoxymethoxyethyl)benzaldehyde (8.2 g, 42.1 mmol), methanol (160 mL), water (6 mL) and concentrated hydrochloric acid (4 mL) was stirred at 60° C. for 17.5 hours. After cooling to room temperature, the reaction mixture was neutralized with aqueous sodium hydroxide and evaporated under reduced pressure to remove methanol. The residue was extracted twice with ethyl acetate. The combined organic layers were washed with saturated aqueous sodium chloride and dried over anhydrous magnesium sulfate. After concentration, the resulting residue was purified by silica gel column chromatography (hexane:ethyl acetate=90:10 to 50:50) to give 4-(2-hydroxyethyl)benzaldehyde (6.3 g).

Next, to a mixture of 4-(2-hydroxyethyl)benzaldehyde (6.3 g, 42.2 mmol) and chloroform (170 mL), triethylamine (5.1 g, 50.6 mmol), benzoyl chloride (7.1 g, 50.6 mmol) and 4-dimethylaminopyridine (515 mg, 4.2 mmol) were added at 0° C. The reaction mixture was stirred at room temperature for 2 hours, poured into a mixture of ethyl acetate and water, and then extracted with ethyl acetate. The organic layer was washed with saturated aqueous sodium chloride and dried over anhydrous magnesium sulfate. After concentration, the resulting residue was purified by neutral silica gel column chromatography (hexane:ethyl acetate=20:1 to 10:1) to give 4-(2-benzoyloxyethyl)benzaldehyde (5.4 g).

Next, to a mixture of 3-(methoxymethoxy)pyridine (2.4 g, 17.4 mmol) and diethyl ether (240 ml), a 1.47 mol/L t-butyllithium n-pentane solution (15 ml, 22.0 mmol) was added dropwise at −70° C. over 15 minutes. After stirring at −70° C. for 1 hour, a diethyl ether solution of 4-(2-benzoyloxyethyl)benzaldehyde (5.35 g, 21.0 mmol) was added over 10 minutes and stirred at −70° C. for 1.5 hours. After warming to room temperature, the reaction mixture was poured into saturated aqueous ammonium chloride and extracted with ethyl acetate. The organic layer was washed with saturated aqueous sodium chloride, dried over anhydrous magnesium sulfate and concentrated under reduced pressure. The resulting residue was purified by silica gel column chromatography (hexane:ethyl acetate=20:80) to give [4-(2-benzoyloxyethyl)phenyl]-[3-(methoxymethoxy)pyridin-4-yl]-methanol (2.2 g, 32%) as a yellow powder.

Next, to a suspension of [4-(2-benzoyloxyethyl)phenyl]-[3-(methoxymethoxy)pyridin-4-yl]-methanol (2.62 g, 6.67 mmol) and methanol (34 mL), concentrated hydrochloric acid (4.3 mL) was added and the reaction mixture was stirred at 100° C. for 10 minutes. After cooling to room temperature, the reaction mixture was concentrated. Ethyl acetate was added to the residue and the resulting precipitate was filtered to afford a yellow crystal (2.58 g). A mixture of this crystal (1.55 g), methanol (40 mL) and 10% palladium/carbon (0.80 g) was stirred under a hydrogen atmosphere at room temperature for 14 hours. After filtration to remove the insoluble materials, the filtrate was concentrated under reduced pressure and the resulting residue was poured into saturated aqueous NaHCO$_3$ and extracted with ethyl acetate. The organic layer was washed with saturated aqueous sodium chloride, dried over anhydrous magnesium sulfate, and concentrated under reduced pressure. The resulting residue was purified by NH silica gel column chromatography (hexane:ethyl acetate=50:50 to chloroform:methanol=10:1) to give the titled compound (0.37 g) as a colorless powder.

$^1$H-NMR (200 MHz, CDCl$_3$): δ 3.05 (t, J=7.0 Hz, 2H), 4.02 (s, 2H), 4.52 (t, J=7.0 Hz, 2H), 6.98 (d, J=5.0 Hz, 2H), 7.16-7.28 (m, 4H), 7.36-7.58 (m, 3H), 7.95-8.05 (m, 3H), 8.29 (s, 1H).

ESI m/z=356(M+Na).

Reference Example 11

Preparation of 2-(4-ethylbenzyl)-3-hydroxypyridine

To a solution of 2-bromo-3-hydroxypyridine (15 g, 0.0862 mol) in chloroform (260 mL), ethyldiisopropylamine (18 mL, 0.103 mol) and 2-(triethylsilyl)ethoxymethyl chloride (16.7 mL, 0.0948 mol) were added at 0° C. After the mixture was stirred at room temperature for 2 hours, water (50 mL) was added thereto and the precipitated insoluble materials were filtered off. The organic layer of the filtrate was separated, washed with water, and then dried over anhydrous magnesium sulfate. After the solvent was distilled off under reduced pressure, the resulting residue was purified by silica gel column chromatography (hexane:ethyl acetate=9:1) to give 2-bromo-3-[2-(triethylsilyl)ethoxymethoxy]pyridine (20.3 g, 77%) as a light-yellow oil.

Next, to a solution of 2-bromo-3-[2-(triethylsilyl)ethoxymethoxy]pyridine (2.0 g, 6.57 mmol) in THF (22 mL), a 1.47 M n-pentane solution of tert-butyllithium (9.6 mL, 14.1 mmol) was slowly added dropwise at −78° C. After 20 minutes, a solution of 4-ethylbenzaldehyde (1.0 g, 7.45 mmol) in THF (5 mL) was added dropwise to the reaction mixture. After stirring at −78° C. for 10 minutes, the reaction mixture was warmed to room temperature and saturated aqueous ammonium chloride was added thereto, followed by extraction with ethyl acetate. The organic layer was washed with saturated aqueous sodium chloride and dried over anhydrous magnesium sulfate. After the solvent was distilled off under reduced pressure, the resulting residue was purified by silica gel column chromatography (hexane:ethyl acetate=9:1) to give 4-ethylphenyl-[3-[2-(triethylsilyl)ethoxymethoxy]]pyridin-2-yl-methanol (0.89 g, 38%).

To a solution of 4-ethylphenyl-[3-[2-(triethylsilyl) ethoxymethoxy]]pyridin-2-yl-methanol (2.35 g, 6.54 mmol) in THF-water (25:1; 60 mL), p-toluenesulfonic acid monohydrate (2.8 g, 16.4 mmol) was added and stirred at room temperature for 20 hours and at 40° C. for 4 hours. After cooling the reaction mixture to room temperature, saturated sodium bicarbonate solution (100 mL) was added and the resulting mixture was then extracted with ethyl acetate. The organic layer was washed with saturated aqueous sodium chloride and dried over anhydrous magnesium sulfate. After the solvent was distilled off under reduced pressure, the resulting residue was purified by silica gel column chromatography (hexane:ethyl acetate=2:1) to give 4-ethylphenyl-3-hydroxypyridin-2-yl-methanol (0.62 g).

A mixture of 4-ethylphenyl-3-hydroxypyridin-2-yl-methanol (0.60 g, 2.62 mmol), 20% palladium hydroxide/carbon (300 mg) and acetic acid (8 mL) was stirred under a hydrogen atmosphere for 76 hours. After filtration to remove the insoluble materials, the filtrate was purified by silica gel column chromatography (hexane:ethyl acetate=1:1) to give 2-(4-ethylbenzyl)-3-hydroxypyridine (0.46 g, 82%) as a colorless powder.

$^1$H-NMR (300 MHz, CDCl$_3$): δ 1.19 (t, J=7.7 Hz, 3H), 2.59 (q, J=7.7 Hz, 2H), 4.19 (s, 2H), 7.04-7.26 (m, 6H), 8.09 (m, 1H).

ESI m/z=252(M+Na).

Reference Example 12

Preparation of 3-(4-ethylbenzyl)-4-hydroxypyridine

A 1.58 M n-hexane solution of n-butyllithium (30.1 mL, 0.0476 mol) and THF (125 mL) were mixed and a solution of diisopropylamine (6.67 mL, 0.0476 mol) in THF (25 mL) was added dropwise thereto at −20° C., followed by stirring for 25 minutes. After cooling the reaction mixture to −78° C., a solution of 4-chloropyridine (5.4 g, 0.0476 mol) in THF (25 mL) was added dropwise. After 15 minutes, a solution of 4-ethylbenzaldehyde (6.4 g, 0.0477 mol) in THF (25 mL) was added dropwise and stirred for 30 minutes. After warming the reaction mixture to room temperature, saturated aqueous ammonium chloride was added and the resulting mixture was then extracted twice with ethyl acetate. The combined organic layers were washed with saturated aqueous sodium chloride and dried over anhydrous magnesium sulfate. After the solvent was distilled off under reduced pressure, the resulting residue was purified by silica gel column chromatography (hexane:ethyl acetate=2:1) to give (4-chloropyridin-3-yl)-(4-ethylphenyl)methanol (8.4 g, 71%) as a light-yellow crystal.

Next, to a solution of (4-chloropyridin-3-yl)-(4-ethylphenyl)methanol (3.2 g, 0.0129 mol) in chloroform (45 mL), Dess-Martin periodine (6.5 g, 0.0154 mol) was added under ice cooling and the reaction mixture was stirred at room temperature for 5 hours. After filtration to remove the precipitated insoluble materials, the filtrate was washed with 1M NaOH (40 mL) and saturated aqueous sodium chloride, and then dried over anhydrous magnesium sulfate. The solvent was distilled off under reduced pressure and the resulting residue was purified by NH silica gel chromatography (ethyl acetate) to give 4-chloro-3-(4-ethylbenzoyl)pyridine (3.4 g) as a yellow oil. A mixture of 4-chloro-3-(4-ethylbenzoyl) pyridine (3.4 g), 3M HCl (35 mL) and 30% H$_2$O$_2$ (2 drops) was heated under reflux for 6.5 hours. After cooling to room temperature, the reaction mixture was neutralized with Na$_2$CO$_3$. The resulting precipitate was filtered and washed with ethyl acetate to give 3-(4-ethylbenzoyl)-4-hydroxypyridine (2.9 g, 92% for 2 steps) as a light-yellow crystal.

ESI m/z=250(M+Na).

Next, a mixture of 3-(4-ethylbenzoyl)-4-hydroxypyridine (2.69 g, 0.0118 mol), 20% palladium hydroxide/carbon (530 mg) and methanol (60 mL) was stirred under a hydrogen atmosphere for 18 hours. Additional 20% palladium hydroxide/carbon (300 mg) was added and stirred for 6 hours, followed by further addition of 20% palladium hydroxide/carbon (340 mg) and stirring for 15 hours. After filtration to remove the insoluble materials, the filtrate was purified by silica gel column chromatography (chloroform:methanol=10:1) to give 3-(4-ethylbenzyl)-4-hydroxypyridine (2.09 g, 83%) as a colorless amorphous substance.

$^1$H-NMR (300 MHz, CDCl$_3$): δ 1.19 (t, J=7.7 Hz, 3H), 2.59 (q, J=7.7 Hz, 2H), 3.77 (s, 2H), 6.38 (d, 1H), 7.05 (s, 4H), 7.29 (s, 1H), 7.39 (m, 1H).

Reference Example 13

Preparation of 3-(4-ethylbenzyl)-1H-pyrazin-2-one

A 1.58 M n-hexane solution of n-butyllithium (19.0 mL, 0.0300 mol) and THF (50 mL) were mixed, followed by addition of 2,2,6,6-tetramethylpiperidine (4.2 g, 0.0300 mol) at −78° C. The reaction mixture was warmed to 0° C. and stirred for 20 minutes. After the reaction mixture was cooled again to −78° C., a solution of 2-chloropyrazine (2.5 g, 0.0218 mol) in THF (5 mL) was added dropwise thereto and stirred at −78° C. for 1 hour. A solution of 4-ethylbenzaldehyde (3.3 g, 0.0240 mol) in THF (5 mL) was added dropwise to the reaction mixture, followed by stirring for 30 minutes. Concentrated hydrochloric acid (10 mL) and ethanol (5 mL) were added to the reaction mixture. After warming to room temperature, the reaction mixture was poured into saturated aqueous sodium bicarbonate and the resulting mixture was extracted twice with ethyl acetate. The combined organic layers were washed with saturated aqueous sodium chloride and dried over anhydrous magnesium sulfate. After the solvent was distilled off under reduced pressure, the resulting residue was purified by silica gel column chromatography (hexane:ethyl acetate=3:2) to give (2-chloropyrazin-3-yl)-(4-ethylphenyl)methanol (3.1 g, 57%) as a brown oil.

Next, to a solution of (2-chloropyrazin-3-yl)-(4-ethylphenyl)methanol (3.1 g, 0.0125 mol) in toluene (24 mL), KOH (2.8 g, 0.050 mol), K$_2$CO$_3$ (1.7 g, 0.0125 mol), benzyl alcohol (1.89 g, 0.0175 mol) and tris[2-(2-methoxyethoxy)ethyl] amine (0.40 g, 0.00125 mol) were added and stirred at 120° C. for 2 hours. After cooling the reaction mixture to room temperature, water was poured and the resulting mixture was extracted twice with ethyl acetate. The combined organic layers were washed with saturated aqueous sodium chloride and dried over anhydrous magnesium sulfate. After the solvent was distilled off under reduced pressure, the resulting residue was purified by silica gel column chromatography (hexane:ethyl acetate=87:13) to give 2-benzyloxy-3-(4-ethylbenzyl)pyrazine (420 mg, 11%) as a yellow oil.

Next, a mixture of 2-benzyloxy-3-(4-ethylbenzyl)pyrazine (420 mg, 1.38 mmol), 10% palladium carbon (40 mg) and ethanol (5 mL) was stirred under a hydrogen atmosphere for 18 hours. After filtration to remove the insoluble materials, the filtrate was purified by silica gel column chromatography (hexane:ethyl acetate=1:2) to give 3-(4-ethylbenzyl)-1H-pyrazin-2-one (120 mg, 40%) as a yellow crystal.

¹H-NMR (300 MHz, CDCl₃): δ 1.21 (t, J=7.7 Hz, 3H), 2.60 (q, J=7.7 Hz, 2H), 4.11 (s, 2H), 7.07 (m, 1H), 7.16 (m, 2H), 7.29 (m, 2H), 7.38 (m, 1H).

Reference Example 14

Preparation of 5-(ethylbenzyl)-2,6-dimethyl-3H-pyrimidin-4-one

To a solution of acetamidine hydrochloride (2.86 g, 0.030 mol) in methanol (86 mL), a 25 wt % methanol solution of sodium methoxide (6.48 mL, 0.030 mol) was added at 0° C. and stirred for 10 minutes. The precipitated crystal was filtered through celite and a solution of methyl 2-(4-ethylbenzyl)acetoacetate (5.0 g, 0.020 mol) in methanol (10 mL) was added to the resulting filtrate, followed by stirring at room temperature for 5 hours. After the reaction mixture was concentrated, water was added to the resulting residue and the mixture was extracted twice with ethyl acetate. The combined organic layers were washed with saturated aqueous sodium chloride and dried over anhydrous magnesium sulfate. The solvent was distilled off under reduced pressure and the resulting crystal was suspended in ethyl acetate, followed by filtration to give the titled compound (1.49 g, 31%) as a colorless powder.

¹H-NMR (300 MHz, DMSO): δ 1.15 (t, J=7.7 Hz, 3H), 2.14 (s, 3H), 2.21 (s, 3H), 2.52 (q, J=7.7 Hz, 2H), 3.70 (s, 2H), 7.06 (s, 4H).

Reference Example 15

4-(4-Ethylbenzyl)-2H-pyridazin-3-one

A 1.58 mol/L n-butyllithium n-hexane solution (67.4 ml, 107 mmol) was added to tetrahydrofuran (500 ml) at −50° C. To this solution, 2,2,6,6-tetramethylpiperidine was added at −50° C. and the resulting mixture was stirred at 0° C. for 1 hour. Next, to this mixture, a solution of 3-chloro-6-methoxypyridazine (7.0 g, 48.4 mmol) in tetrahydrofuran (180 ml) was added at −60° C. over 20 minutes. After stirring for 40 minutes, to this mixture, a solution of 4-ethylbenzaldehyde (7.8 g, 58.1 mmol) in tetrahydrofuran (140 ml) was added and the reaction mixture was stirred at −60° C. for 2 hours. After addition of hydrochloric acid:ethanol:tetrahydrofuran (1:4:5, 100 ml), the reaction mixture was warmed to room temperature and saturated aqueous ammonium chloride was added thereto, followed by extraction with ethyl acetate. The organic layer was dried over anhydrous magnesium sulfate and concentrated under reduced pressure. The resulting residue was purified by silica gel column chromatography (hexane:ethyl acetate=5:1 to 2:1) to give a 6:1 mixture of (4-ethylphenyl)-(3-chloro-6-methoxypyridazin-5-yl)-methanol and (4-ethylphenyl)-(3-chloro-6-methoxypyridazin-4-yl)-methanol (10.7 g, 79%) as a yellow oil.

The 6:1 mixture of (4-ethylphenyl)-(3-chloro-6-methoxypyridazin-5-yl)-methanol and (4-ethylphenyl)-(3-chloro-6-methoxypyridazin-4-yl)-methanol (10.7 g), 5% palladium/carbon (5.4 g) and acetic acid (80 ml) were suspended and stirred under a hydrogen atmosphere at room temperature for 22 hours. After filtration to remove the insoluble materials, the filtrate was concentrated under reduced pressure and the resulting residue was purified by silica gel column chromatography (hexane:ethyl acetate=1:2 to chloroform:methanol=10:1) to give 4-(4-ethylbenzyl)-3-methoxy-pyridazine (2.88 g) and 4-(4-ethylbenzyl)-3-methoxy-pyridazine acetate salt (3.32 g).

To a mixture of 4-(4-ethylbenzyl)-3-methoxy-pyridazine (2.11 g, 9.24 mmol) and chloroform (20 ml), trimethylsilyliodo (1.45 ml, 10.2 mmol) was added and this reaction mixture was stirred at 60° C. for 25 hours. After cooling to room temperature, the reaction mixture was diluted with methanol and concentrated. The resulting residue was purified by silica gel column chromatography (chloroform:methanol=20:1) to give the titled compound (1.36 g, 69%) as a yellow powder.

¹H-NMR (300 MHz, CDCl₃): δ 1.22 (t, J=7.6 Hz, 3H), 2.63 (q, J=7.6 Hz, 2H), 3.90 (s, 2H), 6.79 (d, 1H), 7.15-7.20 (m, 4H), 7.66 (d, 2H), 10.7 (brs, 1H).

ESI m/z=237(M+Na).

Reference Example 16

Preparation of 4-(4-ethylbenzoyl)-3-hydroxypyridine

To a solution of o-iodoxybenzoic acid (IBX) in dimethyl sulfoxide (15 mL), a solution of (4-ethylphenyl)-[3-[2-(trimethylsilyl)ethoxymethoxy]pyridin-4-yl]-methanol (synthesized in Reference Example 6; 3.0 g, 8.34 mmol) in tetrahydrofuran (20 mL) was added and the reaction mixture was stirred at room temperature for 17.5 hours. Water was added to the reaction mixture and the resulting precipitate was filtered and washed with ethyl acetate. The filtrate was washed with water and saturated aqueous sodium chloride, and then dried over anhydrous magnesium sulfate. The solvent was distilled off under reduced pressure to give 4-(4-ethylbenzoyl)-3-[2-(trimethylsilyl)ethoxymethoxy]pyridine (3.4 g).

Next, a mixture of 4-(4-ethylbenzoyl)-3-[2-(trimethylsilyl)ethoxymethoxy]pyridine (3.4 g), p-toluenesulfonic acid monohydrate (3.46 g, 18.2 mmol) and tetrahydrofuran (60 mL) was stirred at 80° C. for 2 hours. After cooling to room temperature, the reaction mixture was poured into saturated aqueous sodium bicarbonate and extracted twice with ethyl acetate. The organic layers were dried over anhydrous magnesium sulfate and concentrated under reduced pressure. The resulting residue was purified by silica gel column chromatography (hexane:ethyl acetate=50:50) to give the titled compound (1.57 g, 83%).

ESI m/z=228(M+H), 226(M-H)

Reference Example 17

Preparation of 2,3,4,6-tetra-O-acetyl-5-thio-D-glucopyranose

To a solution of 1,2,3,4,6-penta-O-acetyl-5-thio-D-glucopyranose (34.0 g, 0.0837 mol) in N,N-dimethylformamide (200 mL), a mixture of methylhydrazine (6.70 mL, 0.125 mmol), acetic acid (7.2 mL, 0.125 mol) and N,N-dimethylformamide (25 mL) was added under ice cooling. After stirring the raction mixture at room temperature for 2.5 hours, 0.5M HCl (300 mL) was added under ice cooling, and the resulting mixture was then extracted twice with ethyl acetate (250 mL). The combined organic phases were washed sequentially with water (200 mL), saturated aqueous NaHCO₃ (100 mL), water (100 mL) and saturated aqueous sodium chloride (100 mL), followed by addition of MgSO₄ and activated charcoal (1 g). After filtration to remove the insoluble materials, the filtrate was concentrated under reduced pressure. The resulting residue was crystallized from isopropyl ether (70 mL) to give 2,3,4,6-tetra-O-acetyl-5-thio-glucopyranose (26.9 g, 88%) as a colorless crystal.

EXAMPLES

The present invention will be further described in more detail in the following examples, which are not intended to limit the scope of the invention.

Example 1

Preparation of 4'-(4'-ethylbenzyl)-5'-methyl-1'H-pyrazol-3'-yl 2,3,4,6-tetra-O-acetyl-5-thio-β-D-glucopyranoside To a solution of 2,3,4,6-tetra-O-acetyl-5-thio-D-glucopyranose (937 mg, 2.6 mmol), 1,2-dihydro-4-(4-ethylbenzyl)-5-methyl-3H-pyrazol-3-one (2.78 g, 12.9 mmol) and triphenylphosphine (1.35 g, 5.1 mmol) in tetrahydrofuran (14 mL), diethyl azodicarboxylate (40% in toluene, 5.1 mmol) was added dropwise at room temperature. After stirring at room temperature for 4 hours, the reaction mixture was concentrated and the resulting residue was purified by silica gel column chromatography (hexane:ethyl acetate=50:50 to 35:65) to give the titled compound (292 mg, 20%) as a light-yellow amorphous substance.

$^1$H-NMR (300 MHz, CDCl$_3$): δ 1.19 (t, J=7.6 Hz, 3H), 1.85 (s, 3H), 2.00 (s, 3H), 2.03 (s, 3H), 2.07 (s, 3H), 2.13 (s, 3H), 2.58 (q, J=7.6 Hz, 2H), 3.28-3.37 (m, 1H), 4.08-4.16 (m, 1H), 4.34 (dd, J=5.0 and 12.0 Hz, 1H), 3.50-3.64 (m, 2H), 5.13 (dd, J=8.9 and 9.3 Hz, 1H), 5.38 (dd, J=9.3 and 10.1 Hz, 1H), 5.55 (dd, J=8.6 and 8.9 Hz, 1H), 5.81 (d, J=8.6 Hz, 1H), 7.00-7.10 (m, 4H).

ESI m/z=561(M–H).

Example 2

Preparation of 1'-acetyl-4'-[(3'-fluoro-4'-methoxyphenyl)methyl]-5'-methyl-1'H-pyrazol-3'-yl 2,3,4,6-tetra-O-acetyl-5-thio-β-D-glucopyranoside To a mixture of 2,3,4,6-tetra-O-acetyl-5-thio-D-glucopyranose (629 mg, 1.73 mmol), 1-acetyl-4-[(3-fluoro-4-methoxyphenyl)methyl]-3-hydroxy-5-methyl-1H-pyrazole (960 mg, 3.45 mmol), triphenylphosphine (601 mg, 2.29 mmol) and tetrahydrofuran (7.9 mL), diisopropyl azodicarboxylate (40% in toluene, 2.04 mL, 3.45 mmol) was slowly added dropwise at 0° C. After stirring at room temperature for 2 hours, the reaction mixture was concentrated and the resulting residue was purified by silica gel column chromatography (hexane:ethyl acetate=7:3) to give the titled compound (647 mg, 60%) as a colorless amorphous substance.

$^1$H-NMR (300 MHz, CDCl$_3$): δ 1.94 (s, 3H), 2.01 (s, 3H), 2.05 (s, 3H) 2.06 (s, 3H), 2.50 (s, 3H), 2.59 (s, 3H), 3.35 (m, 1H), 3.54 (m, 2H), 3.85 (s, 3H), 4.14 (dd, J=4.2 and 11.9 Hz, 1H), 4.27 (dd, J=5.4 and 11.9 Hz, 1H), 5.18 (dd, J=9.4, 7.9 Hz, 1H), 5.39 (t, J=9.4 Hz, 1H), 5.50 (t, J=7.9 Hz, 1H), 5.96 (d, J=7.9 Hz, 1H), 6.80-6.89 (m, 3H).

ESI m/z=647 (M+Na).

mp 118.0-122.0° C.

Example 3

Preparation of 4'-(4'-ethylbenzyl)-1'-isopropyl-5'-methyl-1'H-pyrazol-3'-yl 5-thio-β-D-glucopyranoside To a suspension of 2,3,4,6-tetra-O-acetyl-5-thio-D-glucopyranose (200 mg, 0.55 mmol), 4-(4-ethylbenzyl)-3-hydroxy-1-isopropyl-5-methyl-1H-pyrazole (425 mg, 1.36 mmol) and triphenylphosphine (288 mg, 1.10 mmol) in toluene (5 mL), diethyl azodicarboxylate (40% in toluene, 478 mg, 1.10 mmol) was added dropwise under ice cooling. After stirring at room temperature for 13 hours, the reaction mixture was concentrated and the resulting residue was purified by silica gel column chromatography (hexane:ethyl acetate=2:1) to give a crude product of 4'-(4'-ethylbenzyl)-1'-isopropyl-5'-methyl-1'H-pyrazol-3'-yl 2,3,4,6-tetra-O-acetyl-5-thio-β-D-glucopyranoside (58 mg). The crude product of 4'-(4'-ethylbenzyl)-1'-isopropyl-5'-methyl-1'H-pyrazol-3'-yl 2,3,4,6-tetra-O-acetyl-5-thio-β-D-glucopyranoside (50 mg) was dissolved in methanol (2 mL), followed by addition of sodium methoxide (18 mg, 0.3 mmol) at room temperature. After stirring at room temperature for 14 hours, the solvent was distilled off under reduced pressure and the resulting residue was purified by silica gel column chromatography (chloroform:methanol=50:1 to 25:1 to 20:1) to give the titled compound (11 mg, 5%) as a colorless powder.

$^1$H-NMR (300 MHz, MeOH-d$_4$): δ 1.18 (t, J=7.6 Hz, 3H), 1.37 (d, J=6.7 Hz, 6H), 2.08 (s, 3H), 2.57 (q, 7.6 Hz, 2H), 2.71-2.80 (m, 1H), 3.18-3.26 (m, 1H), 3.50-3.58 (m, 1H), 3.65 (d, J=3.6 Hz, 2H), 3.70-3.78 (m, 2H), 3.84-3.92 (m, 1H), 4.35-4.45 (m, 1H), 5.40 (d, J=8.7 Hz, 1H), 7.00-7.10 (m, 4H).

ESI m/z=435(M–H).

mp 54.0-58.5° C.

Example 4

Preparation of 4'-(4'-ethylbenzyl)-1'-isopropyl-5'-trifluoromethyl-1'H-pyrazol-3'-yl 2,3,4,6-tetra-O-acetyl-5-thio-β-D-glucopyranoside To a suspension of 2,3,4,6-tetra-O-acetyl-5-thio-D-glucopyranose (237 mg, 0.650 mmol), 4-(4-ethylbenzyl)-3-hydroxy-1-isopropyl-5-trifluoromethyl-1H-pyrazole (synthesized as described in WO0236602; 84 mg, 0.269 mmol) and triphenylphosphine (170 mg, 0.650 mmol) in toluene (2.3 mL), diisopropyl azodicarboxylate (40% in toluene, 33 mg, 0.650 mmol) was added dropwise under ice cooling. After stirring at room temperature for 15 hours, the reaction mixture was concentrated and the resulting residue was purified by silica gel column chromatography (hexane:ethyl acetate=70:30) to give 4'-(4'-ethylbenzyl)-1'-isopropyl-5'-trifluoromethyl-1'H-pyrazol-3'-yl 2,3,4,6-tetra-O-acetyl-5-thio-β-D-glucopyranoside (67 mg, 38%).

$^1$H-NMR (300 MHz, CDCl$_3$): δ 1.19 (t, J=7.7 Hz, 3H), 1.42 (d, J=6.5 Hz, 6H), 1.91 (s, 3H), 2.00 (s, 3H), 2.04 (s, 3H), 2.05 (s, 3H), 2.59 (q, J=7.7 Hz, 2H), 3.31 (m, 1H), 3.71 (brd, J=0.93 Hz, 2H), 4.15 (dd, J=4.0, 11.8 Hz, 1H), 4.28 (dd, J=5.3, 11.8 Hz, 1H), 4.49 (m, 1H), 5.16. (dd, J=8.3, 9.3 Hz, 1H), 5.39 (dd, J=9.3, 9.9 Hz, 1H), 5.54 (t, J=8.3 Hz, 1H), 5.85 (d, J=8.3 Hz, 1H), 7.08 (s, 4H).

ESI m/z=681(M+Na).

Example 5

Preparation of 1'-cyclobutyl-4'-(4'-ethylbenzyl)-5'-trifluoromethyl-1'H-pyrazol-3'-yl 2,3,4,6-tetra-O-acetyl-5-thio-β-D-glucopyranoside To a solution of 2,3,4,6-tetra-O-acetyl-5-thio-D-glucopyranose (49 mg, 0.134 mmol), 1-cyclobutyl-4-(4-ethylbenzyl)-3-hydroxy-5-trifluoromethyl-1H-pyrazole (29 mg, 0.0894 mmol) and triphenylphosphine (35 mg, 0.134 mmol) in tetrahydrofuran (0.5 mL), diisopropyl azodicarboxylate (40% in toluene, 0.079 mL, 0.134 mmol) was added dropwise under ice cooling. After stirring at room temperature for 15 hours, the reaction mixture was concentrated and the resulting residue was purified by silica gel column chromatography (hexane:ethyl acetate=2:1) to give the titled compound (27 mg, 45%).

$^1$H-NMR (300 MHz, CDCl$_3$): δ 1.19 (t, J=7.6 Hz, 3H), 1.70-1.85 (m, 2H), 1.92 (s; 3H), 2.00 (s, 3H), 2.05 (s, 3H), 2.06 (s, 3H), 2.26-2.39 (m, 2H), 2.58 (q, J=7.6 Hz, 2H), 2.58-2.75 (m, 2H), 3.33 (m, 1H), 3.70 (brs, 2H), 4.15 (dd, J=4.2, 11.9 Hz, 1H), 4.28 (dd, J=5.4, 11.9 Hz, 1H), 4.73 (m, 1H), 5.19 (dd, J=8.1, 9.1 Hz, 1H), 5.40 (dd, J=9.1, 9.8 Hz, 1H), 5.55 (t, J=8.1 Hz, 1H), 5.92 (d, J=8.1 Hz, 1H), 7.08 (s, 4H).

ESI m/z=693(M+Na).

Example 6

Preparation of 4'-(4'-ethylbenzyl)pyridin-3'-yl 2,3,4, 6-tetra-O-acetyl-5-thio-β-D-glucopyranoside To a mixture of 2,3,4,6-tetra-O-acetyl-5-thio-D-glucopyranose (1.5 g, 4.12 mmol), 4-(4-ethylbenzyl)-3-hydroxypyridine (2.63 g, 12.3 mmol), triphenylphosphine (2.16 g, 8.24 mmol) and toluene (15 mL), diisopropyl azodicarboxylate (40% in toluene, 4.16 g) was slowly added dropwise under ice cooling. After stirring at room temperature for 21 hours, the reaction mixture was concentrated and the resulting residue was purified by NH silica gel column chromatography (hexane:ethyl acetate=10:90) and silica gel column chromatography (hexane:ethyl acetate=50:50 to 40:60 to 30:70) to give the titled compound (477 mg, 21%) as a light-yellow amorphous substance.

$^1$H-NMR (300 MHz, CDCl$_3$): δ 1.22 (t, J=7.6 Hz, 3H), 1.95 (s, 3H), 2.02 (s, 3H), 2.05 (s, 3H), 2.06 (s, 3H), 2.62 (q, J=7.6 Hz, 2H), 3.25-3.35 (m, 1H), 3.88 (s, 2H), 4.15 (dd, J=3.6 and 12.0 Hz, 1H), 4.21 (dd, J=5.5 and 12.0 Hz, 1H), 5.18 (dd, J=8.9 and 9.4 Hz, 1H), 5.39 (d, J=8.7 Hz, 1H), 5.40 (dd, J=9.4 Hz, 10.4 Hz, 1H), 5.64 (dd, J=8.7 and 8.9 Hz, 1H), 6.97 (d, J=4.8 Hz, 1H), 7.06 (d, J=8.2 Hz, 2H), 7.13 (d, J=8.2 Hz, 2H), 8.22 (d, J=4.8 Hz, 1H), 8.46 (s, 1H).

ESI m/z=582(M+Na).

Example 7

Preparation of 4'-(4'-methoxycarbonylbenzyl)pyridin-3'-yl 2,3,4,6-tetra-O-acetyl-5-thio-β-D-glucopyranoside To a solution of 2,3,4,6-tetra-O-acetyl-5-thio-D-glucopyranose (1.57 g, 4.32 mmol), 4-(4-methoxycarbonylbenzyl)-3-hydroxypyridine (0.70 g, 2.88 mmol) and triphenylphosphine (1.13 g, 4.32 mmol) in tetrahydrofuran (7.0 mL), diisopropyl azodicarboxylate (40% in toluene, 2.17 g, 4.32 mmol) was added dropwise at 0° C. After stirring at room temperature for 15 hours, the reaction mixture was concentrated and the resulting residue was purified by neutral silica gel column chromatography (hexane:ethyl acetate=2:3) and further purified twice by NH silica gel column chromatography (hexane:ethyl acetate=2:3) to give the titled compound (323 mg, 19%).

$^1$H-NMR (300 MHz, CDCl$_3$): δ 1.95 (s, 3H), 2.02 (s, 3H), 2.05 (s, 3H), 2.06 (s, 3H), 3.25-3.35 (m, 1H), 3.90 (s, 3H), 3.97 (s, 2H), 4.12 (dd, J=3.6 and 11.8 Hz, 1H), 4.30 (dd, J=5.4 and 11.8 Hz, 1H), 5.19 (dd, J=8.7 and 9.3 Hz, 1H), 5.39 (dd, J=9.3 Hz, 10.4 Hz, 1H), 5.41 (d, J=8.7 Hz, 1H), 5.60 (t, J=8.7 Hz, 1H), 6.98 (d, J=5.0 Hz, 1H), 7.23 (d, J=8.5 Hz, 2H), 7.98 (d, J=8.5 Hz, 2H), 8.24 (d, J=5.0 Hz, 1H), 8.49 (s, 1H).

ESI m/z=612(M+Na).

Example 8

Preparation of 4'-[4'-(2'-benzoyloxyethyl)benzyl]pyridin-3'-yl 2, 3, 4, 6-tetra-O-acetyl-5-thio-β-D-glucopyranoside To a solution of 2, 3, 4, 6-tetra-O-acetyl-5-thio-D-glucopyranose (2.13 g, 5.85 mmol), 4-[4-(2-benzoyloxyethyl)benzyl]-3-hydroxypyridine (1.30 g, 3.90 mmol) and triphenylphosphine (1.53 g, 5.85 mmol) in tetrahydrofuran (7.0 mL), duisopropyl azodicarboxylate (40% in toluene, 2.96 g, 5.85 mmol) was added dropwise at 0° C. After stirring at room temperature for 3 hours, the reaction mixture was concentrated and the resulting residue was purified by neutral silica gel column chromatography (hexane:ethyl acetate=1:3) and further purified by NH silica gel column chromatography (hexane:ethyl acetate=3:2) to give a mixture of the titled compound and triphenylphosphine oxide (1.66 g). This product was used for Example 16 without further purification.

$^1$H-NMR (300 MHz, CDCl$_3$): δ 1.95 (s, 3H), 2.02 (s, 3H), 2.05 (s, 3H), 2.06 (s, 3H), 3.01 (t, J=7.0 Hz, 2H), 3.25-3.35 (m, 1H), 3.89 (s, 2H), 4.15 (dd, J=3.9 and 12.0 Hz, 1H), 4.21 (dd, J=5.6 and 12.0 Hz, 1H), 4.51 (t, J=7.0 Hz, 2H), 5.18 (dd, J=9.0 and 9.5 Hz, 1H), 5.38 (d, J=8.6 Hz, 1H), 5.39 (dd, J=9.5 Hz, 10.2 Hz, 1H), 5.63 (dd, J=8.6 and 9.0 Hz, 1H), 6.96 (d, J=4.8 Hz, 1H), 7.11 (d, J=8.2 Hz, 2H), 7.23 (d, J=8.2 Hz, 2H), 7.99-8.02 (m, 2H), 8.23 (d, J=4.2 Hz, 1H), 8.45 (s, 1H).

ESI m/z=702 (M+Na).

Example 9

Preparation of 3'-(4'-ethylbenzyl)-1'H-pyrazin-2'-yl 2, 3, 4, 6-tetra-O-acetyl-5-thio-β-D-glucopyranoside To a solution of 2, 3, 4, 6-tetra-O-acetyl-5-thio-D-glucopyranose (408 mg, 1.12 mmol), 3-(4-ethylbenzyl)-1H-pyrazin-2-one (120 mg, 0.560 mmol) and triphenylphosphine (195 mg, 0.743 mmol) in toluene (2.0 mL), diisopropyl azodicarboxylate (40% in toluene, 0.662 mL, 1.12 mmol) was added dropwise at 0° C. After stirring at room temperature for 2 hours, the reaction mixture was concentrated and the resulting residue was purified by silica gel column chromatography (hexane:ethyl acetate=70:30) to give the titled compound (200 mg, 64%) as a colorless oil.

$^1$H-NMR (300 MHz, CDCl$_3$): δ 1.19 (t, J=7.5 Hz, 3H), 1.88 (s, 3H), 2.03 (s, 3H), 2.05 (s, 3H), 2.06 (s, 3H), 2.60 (q, J=7.5 Hz, 2H), 3.38 (m, 1H), 4.02-4.38 (m, 3H), 4.30 (dd, J=5.3, 12.0 Hz, 1H), 5.20 (dd, J=8.5, 9.3 Hz, 1H), 5.45 (dd, J=9.3, 10.1 Hz, 1H), 5.64 (t, J=8.5 Hz, 1H), 6.30 (d, J=8.5 Hz, 1H), 7.09-7.12 (m, 2H), 7.19-7.21 (m, 2H), 8.00 (d, J=2.7 Hz, 2H), 8.18 (d, J=2.7 Hz, 1H).

ESI m/z=583(M+Na).

Example 10

Preparation of 5'-(ethylbenzyl)-2',6'-dimethyl-3'H-pyrimidin-4'-yl 2, 3, 4, 6-tetra-O-acetyl-5-thio-β-D-glucopyranoside To a solution of 2, 3, 4, 6-tetra-O-acetyl-5-thio-D-glucopyranose (677 mg, 1.86 mmol), 5-(ethylbenzyl)-2,6-dimethyl-3H-pyrimidin-4-one (300 mg, 1.23 mmol) and triphenylphosphine (324 mg, 1.24 mmol) in tetrahydrofuran (4.0 mL), diisopropyl azodicarboxylate (40% in toluene, 1.1 mL, 1.86 mmol) was added dropwise at 0° C. After stirring at room temperature for 14 hours, the reaction mixture was concentrated and the resulting residue was purified by silica gel column chromatography (hexane:ethyl acetate=60:40) to give the titled compound (180 mg, 25%) as a light-yellow oil.

$^1$H-NMR (300 MHz, CDCl$_3$): δ 1.19 (t, J=7.6 Hz, 3H), 1.83 (s, 3H), 1.94 (s, 3H), 2.05 (s, 3H), 2.06 (s, 3H), 2.40 (s, 3H), 2.58 (q, J=7.6 Hz, 2H), 2.60 (s, 3H), 3.40 (m, 1H), 3.82 (d, J=15.5 Hz, 1H), 3.92 (d, J=15.5 Hz, 1H), 4.14 (m, 1H), 4.27 (dd, J=5.4, 11.8 Hz, 1H), 5.19 (dd, J=8.4, 9.2 Hz, 1H), 5.38 (dd, J=9.2, 9.9 Hz, 1H), 5.51 (t, J=8.4 Hz, 1H), 6.47 (d, J=8.4 Hz, 1H), 6.96-6.98 (m, 2H), 7.06-7.08 (m, 2H).

ESI m/z=611(M+Na).

Example 11

Preparation of 4'-[(3'-fluoro-4'-methoxyphenyl)methyl]-5'-methyl-1'H-pyrazol-3'-yl 5-thio-β-D-glucopyranoside To a mixture of 1'-acetyl-4'-[(3'-fluoro-4'-methoxyphenyl)methyl]-5'-methyl-1'H-pyrazol-3'-yl 2, 3, 4, 66-tetra-O-acetyl-5-thio-β-D-glucopyranoside (556 mg, 0.890 mmol) and methanol (6 mL), a 25 wt % methanol solution of sodium methoxide (0.096 mL) was added and stirred at room temperature for 24 hours. After addition of dry ice to neutralize the reaction mixture, the reaction mixture was concentrated and the resulting residue was purified by silica gel column chromatography (chloroform:methanol=5:1) to give the titled compound (261 mg, 70%) as a colorless powder.

$^1$H-NMR (300 MHz, MeOH-d$_4$) δ: 2.06 (s, 3H), 2.83 (m, 1H), 3.25 (t, J=8.8 Hz, 1H), 3.56 (t, J=8.8 Hz, 1H), 3.61 (m, 2H), 3.68-3.79 (m, 2H), 3.80 (s, 3H), 3.89 (dd, J=3.9 and 11.5 Hz, 1H), 5.41 (d, J=8.8 Hz, 1H), 6.87-6.97 (m, 3H).

ESI m/z=437 (M+Na).

mp 145.0-147.0° C.

Example 12

Preparation of 1'-acetyl-4'-[(3'-fluoro-4'-methylphenyl)methyl]-5'-methyl-pyrazol-3'-yl 5-thio-β-D-glucopyranoside To a suspension of 4'-[(3'-fluoro-4'-methylphenyl)methyl]-5'-methyl-1'H-pyrazol-3'-yl 5-thio-β-D-glucopyranoside (150 mg, 0.376 mmol) in tetrahydrofuran (5.0 mL), acetic anhydride (0.05 mL) and acetic acid (0.05 mL) were added and stirred for 72 hours. The reaction mixture was concentrated and the resulting residue was purified by silica gel column chromatography (chloroform:methanol=10:1) to give the titled compound (89 mg, 54%) as a colorless powder.

ESI m/z=463 (M+Na).

mp 184.0-194.0° C. (decomp.).

Example 13

Preparation of 1'-ethoxycarbonyl-4'-[(4'-methoxyphenyl)methyl]-5'-methyl-pyrazol-3'-yl 6-O-ethoxycarbonyl-5-thio-β-D-glucopyranoside To a mixture of 4'-[(4'-methoxyphenyl)methyl]-5'-methyl-1'H-pyrazol-3'-yl 5-thio-β-D-glucopyranoside (59 mg, 0.149 mmol) and collidine (1.0 mL), ethyl chlorocarbonate (49 mg, 0.449 mmol) was added and stirred at room temperature for 16 hours. After being neutralized with 10% citric acid, the reaction mixture was diluted with ethyl acetate, washed with saturated aqueous sodium chloride, and then dried over anhydrous magnesium sulfate. The solvent was concentrated and the resulting residue was purified by silica gel column chromatography (hexane:ethyl acetate=10:1) to give the titled compound (32 mg, 40%) as a colorless powder.

$^1$H-NMR (500 MHz, MeOH-d$_4$) δ: 1.26 (t, J=7.3 Hz, 3H), 1.41 (t, J=6.7 Hz, 3H), 2.40 (s, 3H), 3.11 (ddd, J=3.7, 6.7 and 9.8 Hz, 1H), 3.32 (dd, J=8.6 and 9.2 Hz, 1H), 3.56 (dd, J=9.2 and 9.8 Hz, 1H), 3.74 (s, 3H), 3.75 (t, J=8.6 Hz, 1H), 4.15 (q, J=6.7 Hz, 2H), 4.32 (dd, J=6.7 and 11.6 Hz, 1H), 4.40-4.48 (m, 3H), 5.78 (d, J=8.6 Hz, 1H), 6.79 (m, 2H), 7.09 (m, 2H).

ESI m/z=563(M+Na).

mp 106.0-110.0° C.

Example 14

Preparation of 4'-(4'-ethylbenzyl)pyridin-3'-yl 5-thio-β-D-glucopyranoside

To a mixture of 4'-(4'-ethylbenzyl)pyridin-3'-yl 2, 3, 4, 6-tetra-O-acetyl-5-thio-β-D-glucopyranoside (438 mg, 0.78 mmol) and methanol (5 mL), sodium methoxide (8 mg, 0.15 mmol) was added at room temperature and stirred for 23 hours. After addition of a small amount of dry ice to neutralize the reaction mixture, the reaction mixture was concentrated and the resulting residue was purified by silica gel column chromatography (chloroform:methanol=9:1) to give the titled compound (230 mg, 82%) as a colorless powder.

$^1$H-NMR (300 MHz, CD$_3$OD): δ 1.20 (t, J=7.6 Hz, 3H), 2.60 (q, J=7.6 Hz, 2H), 2.93-3.03 (m, 1H), 3.60 (dd, J=9.2 and 10.0 Hz, 1H), 3.76-4.10 (m, 5H), 5.32 (d, J=8.7 Hz, 1H), 7.07 (d, J=4.8 Hz, 1H), 7.08-7.16 (m, 4H), 8.08 (d, J=4.8 Hz, 1H), 8.53 (s, 1H).

ESI m/z=414(M+Na).

mp 184.0-187.0° C.

Example 15

Preparation of 4'-(4'-ethylbenzyl)pyridin-3'-yl 5-thio-β-D-glucopyranoside (No. 2)

To a solution of 2, 3, 4, 6-tetra-O-acetyl-5-thio-D-glucopyranose (481 mg, 1.32 mmol), 4-(4-ethylbenzyl)-3-hydroxypyridinium borane (200 mg, 0.881 mmol) and triphenylphosphine (230 mg, 1.32 mmol) in tetrahydrofuran (2.5 mL), diisopropyl azodicarboxylate (40% in toluene, 0.781 mL, 1.32 mmol) was added dropwise at 0° C. After stirring at room temperature for 2.5 hours, the reaction mixture was concentrated and the resulting residue was purified by silica gel column chromatography (hexane:ethyl acetate=2:1) to give a crude product of 4-(4-ethylbenzyl)-3-(2, 3, 4, 6-tetra-O-acetyl-5-thio-β-D-glucopyranosyloxy)pyridinium borane (440 mg) as a colorless oil. To this crude product, triethylamine:methanol:water (2:1:1, 3 mL) was added and the resulting mixture was stirred at room temperature for 24 hours. The reaction mixture was concentrated and the resulting residue was mixed, without purification, with methanol (1.8 mL) and 2M HCl (1.8 mL), followed by stirring at room temperature for 30 minutes. After addition of saturated sodium bicarbonate solution under ice cooling, the reaction mixture was extracted with chloroform (5 mL×4). The organic layers were concentrated and the resulting residue was purified by silica gel column chromatography (chloroform:methanol 7:1) to give the titled compound (30 mg, 9%).

Example 16

Preparation of 4'-[4'-(2'-hydroxyethyl)benzyl]pyridin-3'-yl 5-thio-β-D-glucopyranoside The crude product of 4'-[4'-(2'-benzoyloxyethyl)benzyl]pyridin-3'-yl 2, 3, 4, 6-tetra-O-acetyl-5-thio-β-D-glucopyranoside (1.66 g) obtained in Example 8 and methanol (10 mL) were mixed, followed by addition of 1M NaOMe (0.25 mL). The reaction mixture was stirred at room temperature for 23 hours. After addition of a small amount of dry ice to neutralize the reaction mixture, the reaction mixture was concentrated and the resulting residue was purified by silica gel column chromatography (chloroform:methanol=5:1) to give a 5:1 mixture of the titled compound and its α-isomer (193 mg, 12%). To this mixture, pyridine (4 mL) and acetic anhydride (0.44 mL) were added. The reaction mixture was stirred for 2 hours and concentrated. The residue was diluted with toluene and concentrated again. The resulting residue was purified by NH silica gel column chromatography (hexane:ethyl acetate=1:3) to give 4'-[4'-(2'-acetyloxyethyl)benzyl]pyridin-3'-yl 2, 3, 4, 6-tetra-O-acetyl-5-thio-β-D-glucopyranoside (185 mg, 63%). A mixture of 4'-[4'-(2'-acetyloxyethyl)benzyl]pyridin-3'-yl 2, 3, 4, 6-tetra-O-acetyl-5-thio-β-D-glucopyranoside (185 mg, 0.300 mmol) and triethylamine:methanol:water (5:1:1, 7 mL) was stirred at room temperature for 17 hours. The reaction mixture was concentrated and the resulting residue was purified by neutral silica gel column chromatography (chloroform:methanol=5:1) to give the titled compound (62 mg, 51%).

$^1$H-NMR (300 MHz, CD$_3$OD): δ 2.78 (t, J=7.2 Hz, 2H), 2.95-3.02 (m, 1H), 3.58 (dd, J=9.0 and 10.3 Hz, 1H), 3.72 (t, J=7.2 Hz, 2H), 3.78 (dd, J=6.0, 11.8 Hz, 1H), 3.83 (t, J=8.9 Hz, 1H), 3.93 (dd, J=3.7, 11.8 Hz, 1H), 3.93-4.09 (m, 2H), 5.31 (d, J=8.9 Hz, 1H), 7.09 (d, J=4.8 Hz, 1H), 7.13-7.18 (m, 4H), 8.13 (d, J=4.8 Hz, 1H), 8.52 (s, 1H).

ESI m/z=430(M+Na).

mp 194.5-195.0° C.

Example 17

Preparation of 4'-[4'-(1'-hydroxy-1'-methyl-ethyl) benzyl]pyridin-3'-yl 5-thio-β-D-glucopyranoside To a mixture of 4'-(4'-methoxycarbonylbenzyl)pyridin-3'-yl 2, 3, 4, 6-tetra-O-acetyl-5-thio-β-D-glucopyranoside (241 mg, 0.409 mmol) and tetrahydrofuran (3 mL), a 1 mmol/mL tetrahydrofuran solution of MeMgBr (4.1 mL, 4.1 mmol) was added at −20° C. After warming to room temperature over 1.5 hours, a 1 mmol/mL tetrahydrofuran solution of MeMgBr (1.5 mL, 1.5 mmol) was added at −20° C. After the reaction mixture was stirred at room temperature for 1.5 hours, a 1 mmol/mL tetrahydrofuran solution of MeMgBr (2.5 mL, 2.5 mmol) was added again at −20° C. After 30 minutes, the reaction mixture was neutralized with acetic acid and concentrated. The resulting residue was purified by neutral silica gel column chromatography (chloroform:methanol=10:1 to 5:1) to give the titled compound (116 mg, 67%) as a colorless oil.

$^1$H-NMR (300 MHz, CD$_3$OD): δ 1.50 (s, 6H), 2.93-3.03 (m, 1H), 3.59 (t, J=8.8 Hz, 1H), 3.78 (dd, J=6.4, 11.3 Hz, 1H), 3.84 (t, J=8.8 Hz, 1H), 3.93 (dd, J=3.6, 11.3 Hz, 1H), 3.98-4.11 (m, 2H), 5.32 (d, J=8.8 Hz, 1H), 7.10 (d, J=4.9 Hz, 1H), 7.21 (d, J=8.5 Hz, 2H), 7.41 (d, J=8.5 Hz, 2H), 8.03 (d, J=4.9 Hz, 1H), 8.53 (s, 1H).

ESI m/z=444(M+Na), 420(M-H).

Example 18

Preparation of 3'-(4'-ethylbenzyl)-1'H-pyrazin-2'-yl 5-thio-β-D-glucopyranoside

To a mixture of 3'-(4'-ethylbenzyl)-1'H-pyrazin-2'-yl 2, 3, 4, 6-tetra-O-acetyl-5-thio-β-D-glucopyranoside (180 mg, 0.321 mmol) and methanol (3 mL), a 1M methanol solution of sodium methoxide (0.032 mL) was added and stirred at room temperature for 2 hours. The reaction mixture was neutralized by addition of dry ice and the resulting precipitate was collected by filtration, thereby obtaining the titled compound (44 mg) as a colorless powder. The filtrate was also concentrated and the resulting residue was purified by silica gel column chromatography (chloroform:methanol=10:1) to give the titled compound (50 mg, total 75%) as a colorless powder.

$^1$H-NMR (300 MHz, CD$_3$OD): δ 1.18 (t, J=7.6 Hz, 3H), 2.58 (q, J=7.6 Hz, 2H), 2.94 (m, 1H), 3.60 (dd, J=8.9, 9.9 Hz, 1H), 3.74 (dd, J=6.2 and 11.3 Hz, 1H), 3.87 (t, J=8.9 Hz, 1H), 3.91 (dd, J=3.7 and 11.3 Hz, 1H), 4.02 (d, J=14.0 Hz, 1H), 4.22 (d, J=14.0 Hz, 1H), 6.15 (d, J=8.9 Hz, 1H), 7.08 (m, J$_{AB}$=7.9 Hz, 2H), 7.19 (m, J$_{AB}$=7.9 Hz, 2H), 8.05-8.08 (m, 2H).

ESI m/z=415 (M+Na)

mp 181.0-183.5° C.

Example 19

Preparation of 5'-(ethylbenzyl)-2',6'-dimethyl-3'H-pyrimidin-4'-yl 5-thio-β-D-glucopyranoside To a mixture of 5'-(ethylbenzyl)-2',6'-dimethyl-3'H-pyrimidin-4'-yl 2, 3, 4, 6-tetra-O-acetyl-5-thio-β-D-glucopyranoside (160 mg, 0.271 mmol) and methanol (3 mL), a 1M methanol solution of sodium methoxide (0.027 mL) was added and stirred at room temperature for 2 hours. After addition of dry ice to neutralize the reaction mixture, the reaction mixture was concentrated and the resulting residue was purified by silica gel column chromatography (chloroform:methanol=10:1) to give the titled compound (62 mg, 54%) as a colorless powder.

$^1$H-NMR (300 MHz, CD$_3$OD): δ 1.18 (t, J=7.6 Hz, 3H), 2.35 (s, 3H), 2.53 (s, 3H), 2.57 (q, J=7.6 Hz, 2H), 2.99 (m, 1H), 3.57 (dd, J=8.9, 9.9 Hz, 1H), 3.74 (dd, J=6.4 and 11.5 Hz, 1H), 3.80 (t, J=8.9 Hz, 1H), 3.85 (d, J=15.2 Hz, 1H), 3.93 (dd, J=3.9 and 11.5 Hz, 1H), 4.05 (d, J=15.2 Hz, 1H), 6.33 (d, J=8.9 Hz, 1H), 7.04-7.10 (m, 4H).

ESI m/z=443 (M+Na)

mp 143.0-147.5° C.

Example 20

Preparation of 6'-(N-acetylamino)-3'-(4'-ethylbenzyl) pyridin-2'-yl 5-thio-β-D-glucopyranoside To a solution of 2, 3, 4, 6-tetra-O-acetyl-5-thio-D-glucopyranose (1.01 g, 2.77 mmol), 6-(N-acetylamino)-3-(4-ethylbenzyl)-1H-pyridin-2-one (synthesized as described in WO03000712; 500 mg, 1.85 mmol) and triphenylphosphine (720 mg, 2.77 mmol) in tetrahydrofuran (4.5 mL), diisopropyl azodicarboxylate (40% in toluene, 1.40 g, 2.77 mmol) was added dropwise at 0° C. After stirring at room temperature for 15 hours, the reaction mixture was concentrated and the resulting residue was purified by silica gel column chromatography (hexane:ethyl acetate=1:1 to 1:2) to give 6'-(N-acetylamino)-3'-(4'-ethylbenzyl)pyridin-2'-yl 2, 3, 4, 6-tetra-O-acetyl-5-thio-β-D-glucopyranoside (520 mg, 46%). ESI m/z=639 (M+Na), 615 (M-H).

A mixture of 6'-(N-acetylamino)-3'-(4'-ethylbenzyl)pyridin-2'-yl 2, 3, 4, 6-tetra-O-acetyl-5-thio-β-D-glucopyranoside (520 mg, 0.843 mmol) and triethylamine:methanol:water (5:1:1, 14 mL) was stirred at room temperature for 43 hours. The reaction mixture was concentrated and the resulting residue was purified by silica gel column chromatography (chloroform:methanol=5:1) to give the titled compound (223 mg, 58%).

$^1$H-NMR (300 MHz, CD$_3$OD): δ 1.20 (t, J=7.6 Hz, 3H), 2.15 (s, 3H), 2.59 (q, J=7.6 Hz, 2H), 2.91 (ddd, J=3.6. 6.5 and 10.3 Hz, 1H), 3.58 (t, J=9.9 Hz, 1H), 3.70-3.98 (m, 5H), 6.16 (d, J=8.7 Hz, 1H), 7.08-7.13 (m, 4H), 7.38 (d, J=7.9 Hz, 1H), 7.62 (brd, J=7.9 Hz, 1H).

ESI m/z=471 (M+Na), 447 (M-H).

Example 21

Preparation of 4'-(4'-ethylbenzyl)-pyridazin-3'-yl 5-thio-β-D-glucopyranoside

To a solution of 2, 3, 4, 6-tetra-O-acetyl-5-thio-D-glucopyranose (3.13 g, 8.58 mmol), 4-(4-ethylbenzyl)-2H-pyridazin-3-one (1.22 g, 5.72 mmol) and triphenylphosphine (2.25 g, 8.58 mmol) in tetrahydrofuran (14 mL), diisopropyl azodicarboxylate (40% in toluene, 4.33 g, 8.58 mmol) was added dropwise at 0° C. After stirring at room temperature for 15 hours, the reaction mixture was concentrated and the resulting residue was purified by silica gel column chromatography (hexane:ethyl acetate=1:1) to give 4'-(4'-ethylbenzyl)-pyridazin-3'-yl 2, 3, 4, 6-tetra-O-acetyl-5-thio-β-D-glucopyranoside (1.47 g) as a crude product.

$^1$H-NMR (300 MHz, CDCl$_3$): δ 1.23 (t, J=7.6 Hz, 3H), 1.94 (s, 3H), 2.02 (s, 3H), 2.06 (s, 3H), 2.06 (s, 3H), 2.63 (q, J=7.6 Hz, 2H), 3.40 (m, 1H), 3.82 (m, 2H), 4.15 (dd, J=3.9, 11.7 Hz, 1H), 4.30 (dd, J=5.5, 11.7 Hz, 1H), 5.22 (dd, J=8.3, 9.2 Hz, 1H), 5.44 (dd, J=9.2, 9.9 Hz, 1H), 5.66 (t, J=8.3 Hz, 1H), 6.65 (d, J=8.2 Hz, 1H), 7.06-7.08 (m, 3H), 7.16-7.18 (m, 2H), 8.76 (d, J=4.7 Hz, 2H).

ESI m/z=561(M+H), 583(M+Na).

A mixture of 4'-(4'-ethylbenzyl)-pyridazin-3'-yl 2, 3, 4, 6-tetra-O-acetyl-5-thio-β-D-glucopyranoside (1.24 g) and triethylamine:methanol:water (5:1:1, 35 mL) was stirred at room temperature for 18 hours. The reaction mixture was concentrated and the resulting residue was purified by silica gel column chromatography (chloroform:methanol=5:1) and further purified by NH silica gel column chromatography (chloroform:methanol=5:1) to give the titled compound (247 mg, 11%).

$^1$H-NMR (300 MHz, CD$_3$OD): δ 1.21 (t, J=7.6 Hz, 3H), 2.62 (q, J=7.6 Hz, 2H), 3.00 (m, 1H), 3.35 (t, J=9.9 Hz, 1H), 3.63 (dd, J=9.0, 9.9 Hz, 1H), 3.80 (dd, 1H), 3.87-3.93 (m, 2H), 3.96 (s, 2H), 6.37 (d, J=8.7 Hz, 1H), 7.17 (s, 4H), 7.24 (d, J=4.7 Hz, 1H), 8.68 (d, J=4.7 Hz, 1H).

ESI m/z=415 (M+Na).

Example 22

Preparation of 4'-(4'-ethylbenzoyl)pyridin-3'-yl 2, 3, 4, 66-tetra-O-acetyl-5-thio-β-D-glucopyranoside To a mixture of 2, 3, 4, 6-tetra-O-acetyl-5-thio-D-glucopyranose (0.53 g, 1.47 mmol), 4-(4-ethylbenzoyl)-3-hydroxypyridine (1.0 g, 4.40 mmol), triphenylphosphine (0.77 g, 2.94 mmol) and toluene (5 mL), diisopropyl azodicarboxylate (40% in toluene, 1.74 mL, 2.94 mmol) was slowly added dropwise under ice cooling. After stirring at room temperature for 4 hours, the reaction mixture was concentrated and the resulting residue was purified by silica gel column chromatography (hexane:ethyl acetate=2:3) to give the titled compound (570 mg, 68%) as a light-yellow amorphous substance.

$^1$H-NMR (300 MHz, CDCl$_3$): δ 1.27 (t, J=7.6 Hz, 3H), 1.87 (s, 3H), 1.94 (s, 3H), 2.02 (s, 3H), 2.06 (s, 3H), 2.73 (q, J=7.6 Hz, 2H), 3.26 (m, 1H), 4.12 (dd, J=3.7, 12.0 Hz, 1H), 4.28 (dd, J=5.6, 12.0 Hz, 1H), 5.24 (dd, J=9.3, 10.0 Hz, 1H), 5.30-5.32 (m, 2H), 7.21 (d, J=4.8 Hz, 1H), 7.62-7.71 (m, 4H), 8.47 (d, J=4.8 Hz, 1H), 8.72 (s, 1H).

ESI m/z=596(M+Na).

Example 23

Preparation of 1'-phenyl-1'H-1',2',4'-triazol-3'-yl 2, 3, 4, 6-tetra-O-acetyl-5-thio-β-D-glucopyranoside To a solution of 2, 3, 4, 6-tetra-O-acetyl-5-thio-D-glucopyranose (677 mg, 1.86 mmol), 3-hydroxy-1-phenyl-1H-1,2,4-triazole (200 mg, 1.24 mmol; purchased from BioNet) and triphenylphosphine (324 mg, 1.24 mmol) in tetrahydrofuran (4.0 mL), diisopropyl azodicarboxylate (40% in toluene, 1.1 mL, 1.86 mmol) was added dropwise at 0° C. After stirring at room temperature for 2 hours, the reaction mixture was concentrated and the resulting residue was purified by silica gel column chromatography (hexane:ethyl acetate=60:40 to 50:50) to give the titled compound (240 mg, 38%) as a colorless oil.

$^1$H-NMR (300 MHz, CDCl$_3$): δ 2.03 (s, 3H), 2.04 (s, 3H), 2.05 (s, 3H), 2.07 (s, 3H), 3.37 (ddd, J=4.4, 5.3, 9.4 Hz, 1H), 4.20 (dd, J=4.4, 11.8 Hz, 1H), 4.35 (dd, J=5.3, 11.8 Hz, 1H), 5.21 (dd, J=8.4, 9.4 Hz, 1H), 5.43 (t, J=9.4 Hz, 1H), 5.59 (dd, J=7.9, 8.4 Hz, 1H), 6.00 (d, J=7.9 Hz, 1H), 7.38 (m, 1H), 7.45-7.52 (m, 2H), 7.61-7.64 (m, 2H), 8.28 (s, 1H).

ESI m/z=530(M+Na).

Using the corresponding starting materials and reactants, the same procedures as shown in the above examples were repeated to give the following compounds according to the present invention. Preferred compounds falling within the scope of the present invention are summarized in Table 1 below, along with the compounds obtained in the above examples.

| Compound No. | Structural formula | $^1$NMR, MS, mp |
|---|---|---|
| Compound 1 | | $^1$H-NMR (300 MHz, CD$_3$OD): δ 1.18(t, J=7.6 Hz, 3H), 1.37(d, J=6.7 Hz, 6H), 2.08 (s, 3H), 2.57(q, 7.6 Hz, 2H), 2.71-2.80(m, 1H), 3.18-3.26(m, 1H), 3.50-3.58(m, 1H), 3.65(d, J=3.6 Hz, 2H), 3.70-3.78(m, 2H), 3.84-3.92(m, 1H), 4.35-4.45(m, 1H), 5.40(d, J=8.7 Hz, 1H), 7.00-7.10(m, 4H). ESI m/z=435 (M−H) mp 54.0-58.5° C. |
| Compound 2 | | $^1$H-NMR (300 MHz, CD$_3$OD): δ 1.18(t, J=7.8 Hz, 3H), 2.05(s, 3H), 2.57(q, J= 7.8 Hz, 2H), 2.75-2.85(m, 1H), 3.20-3.28(m, 1H), 3.50-3.60(m, 1H), 3.65(d, J= 8.0 Hz, 2H), 3.70-3.80(m, 2H), 3.89(dd, J=4.0, 11.5 Hz, 1H), 5.39(d, J= 8.9 Hz, 1H), 7.03-7.10(m, 4H). ESI m/z=393 (M−H) mp 158.0-160.0° C. |

-continued

| Compound No. | Structural formula | $^1$NMR, MS, mp |
|---|---|---|
| Compound 3 | 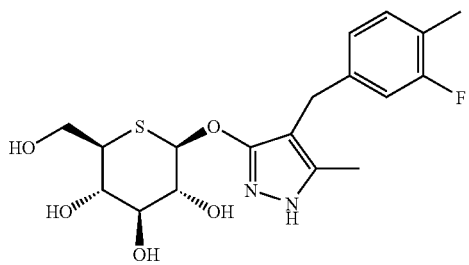 | $^1$H-NMR (300 MHz, CD$_3$OD): δ 2.06(s, 3H), 2.18(m, 3H), 2.83(m, 1H), 3.25(t, J=8.9 Hz, 1H), 3.56(t, J=8.9 Hz, 1H), 3.65(m, 2H), 3.74(t, J=8.9 Hz, 1H), 3.76(dd, J=5.9, 11.5 Hz, 1H), 3.89(dd, J=3.7, 11.5 Hz, 1H), 5.41 (d, J=8.9 Hz, 1H), 6.90(m, 2H), 7.07(t, J=7.93 Hz, 1H), ESI m/z=421(M+Na) mp 159.0-162.0° C. |
| Compound 4 | 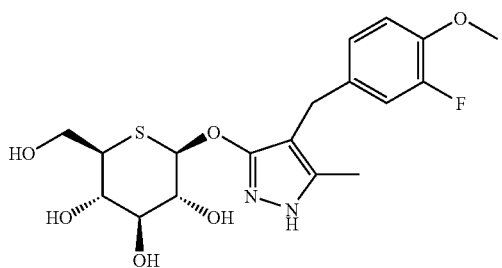 | $^1$H-NMR (300 MHz, CD$_3$OD): δ 2.06(s, 3H), 2.83(m, 1H), 3.25(t, J=8.8 Hz, 1H), 3.56(t, J=8.8 Hz, 1H), 3.61(m, 2H), 3.68-3.79(m, 2H), 3.80(s, 3H), 3.89 (dd, J=3.9, 11.5 Hz, 1H), 5.41(d, J=8.8 Hz, 1H), 6.87-6.97(m, 3H). ESI m/z=437(M + Na) mp 145.0-147.0° C. |
| Compound 5 | 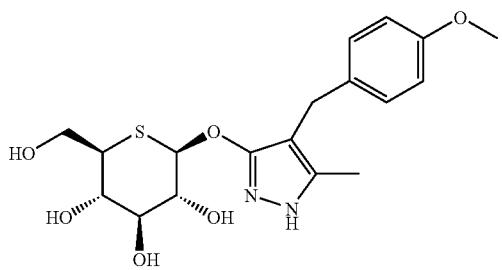 | $^1$H-NMR (300 MHz, CD$_3$OD): δ 2.05(s, 3H), 2.82(m, 1H), 3.24(t, J=8.9 Hz, 1H), 3.55(t, J=8.9 Hz, 1H), 3.62(m, 2H), 3.68-3.79(m, 2H), 3.80(s, 3H), 3.89 (dd, J=3.7, 11.5 Hz, 1H), 5.39(d, J=8.9 Hz, 1H), 6.79(m, J$_{AB}$=8.8 Hz, 2H), 7.09(m, J$_{AB}$=8.8 Hz, 2H). ESI m/z=419(M+Na) mp 145.0-147.0° C. |
| Compound 6 | 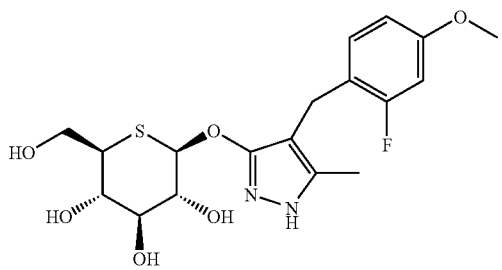 | $^1$H-NMR (300 MHz, CD$_3$OD): δ 2.07(s, 3H), 2.84(m, 1H), 3.24(t, J=8.9 Hz, 1H), 3.56(t, J=8.9 Hz, 1H), 3.61(s, 2H), 3.71-3.79(m, 2H), 3.80(s, 3H), 3.88 (dd, J=3.8, 11.5 Hz, 1H), 5.41(d, J=8.9 Hz, 1H), 6.58-6.64(m, 2H), 7.04 (dd, J=8.4, 9.2 Hz, 1H). ESI m/z=437(M+Na) mp 129.0-132.0° C. |
| Compound 7 | 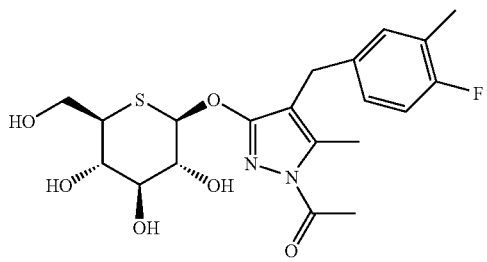 | ESI m/z=463 (M+Na) mp 184.0-194.0° C. |

-continued

| Compound No. | Structural formula | ¹NMR, MS, mp |
|---|---|---|
| Compound 8 | | ESI m/z=563 (M+Na)<br>mp 106.0-110.0° C. |
| Compound 9 | | ESI m/z=435 (M+Na)<br>mp 135.0-137.5° C. |
| Compound 10 | | ESI m/z=(M+Na)<br>mp 149.0-150.0° C. |
| Compound 11 | | ¹H-NMR (300 MHz, CD3OD): δ 1.18(t, J=7.6 Hz, 3H), 1.26(t, J=7.2 Hz, 3H), 1.41 (t, J=7.2 Hz, 3H), 2.40(s, 3H), 2.57(q, J=7.6 Hz, 2H), 3.11(m, 1H), 3.51-3.88(m, 4H), 4.15(q, J=7.2 Hz, 2H), 4.28-4.52(m, 4H), 5.78(d, J=8.4 Hz, 1H), 7.08(s, 4H).<br>ESI m/z=561 (M+Na)<br>mp 79.0-80.0° C. |
| Compound 12 | | ¹H-NMR (300 MHz, CD$_3$OD): δ 0.60(m, 2H), 0.88(m, 2H), 1.83(m, 1H), 2.04(s, 3H), 2.82(m, 1H), 3.25(t, J=8.9 Hz, 1H), 3.56(dd, J=9.0, 10.1 Hz, 1H), 3.60-3.81 (m, 4H), 3.88(dd, J=3.9, 11.5 Hz, 1H), 5.39(d, J=8.9 Hz, 1H); 6.93(m, 2H), 7.04(m, 2H).<br>ESI m/z=429 (M−H)<br>mp 157.0-158.0° C. |

-continued

| Compound No. | Structural formula | ¹NMR, MS, mp |
|---|---|---|
| Compound 13 | | ESI m/z=513 (M+Na)<br>mp 44.0-45.0° C. |
| Compound 14 | | ¹H-NMR (300 MHz, CD3OD): δ 1.18(t, J=7.6 Hz,, 3H), 1.83(m, 2H), 2.36(m, 2H), 2.56 (q, J=7.6 Hz, 2H), 2.69(m, 2H), 2.90(m, 1H), 3.58(t, J=9.3 Hz, 1H), 3.68-3.81(m, 4H), 3.92(dd, J=3.7, 11.3 Hz, 1H), 4.80(m, 1H), 5.71(d, J=8.7 Hz, 1H), 7.05(m, 4H).<br>ESI m/z=525 (M+Na) |
| Compound 15 | | ¹H-NMR (3000 MHz, CD3OD): δ 1.19(t, J=7.6 Hz, 3H), 2.57(q, J=7.6 Hz, 2H), 2.89 (m, 1H), 3.57(dd, J=9.2, 9.8 Hz, 1H), 3.71-3.82(m, 4H), 3.91(dd, J=3.7, 11.3 Hz, 1H), 4.60-4.94(m, 5H), 5.65(d, J=8.5 Hz, 1H), 7.05(m, 4H).<br>ESI m/z=549 (M+Na) |
| Compound 16 | | ESI m/z=561 (M+Na)<br>mp 145.0-147.0° C. |
| Compound 17 | | ESI m/z=445 (M+Na)<br>mp 117.0-132.0° C. |

-continued

| Compound No. | Structural formula | ¹NMR, MS, mp |
|---|---|---|
| Compound 18 | | ESI m/z=523 (M+Na)<br>mp 102.0-112.0° C. |
| Compound 19 | | ¹H-NMR (300 MHz, CD3OD): δ 1.19(t, J=7.6 Hz, 3H), 2.09(s, 1H), 2.39(s, 1H), 2.58(q, J=7.6 Hz, 2H), 2.85(m, 1H), 3.76(t, J=9.0 Hz, 1H), 3.70-3.80(m, 4H), 3.90(dd, J=3.9, 11.5 Hz, 1H), 5.54(d, J=8.9 Hz, 1H), 7.08(d, J=8.1 Hz, 2H), 7.14(d, J=8.1 Hz, 2H), 7.28(s, 4H).<br>ESI m/z=507 (M+Na) |
| Compound 20 | | ¹H-NMR (300 MHz, CD$_3$ODS): δ 1.20(t, J=7.6 Hz, 3H), 2.60(q, J=7.6 Hz, 2H), 2.93-3.03(m, 2H), 3.60(dd, J=9.2 and 10.0 Hz, 1H),<br>3.76-4.10(m, 5H), 5.32(d, J=8.7 Hz, 1H), 7.07(d, J=4.8 Hz, 1H), 7.08-7.16(m, 4H), 8.08(d, J=4.8 Hz, 1H), 8.53(s, 1H).<br>ESI m/z=414 (M+Na)<br>mp 184.0-187.0° C. |
| Compound 21 | | ESI m/z=414 (M+Na)<br>mp 147.0-149.0° C. |

-continued

| Compound No. | Structural formula | $^1$NMR, MS, mp |
|---|---|---|
| Compound 22 | | $^1$H-NMR (300 MHz, CD$_3$OD): δ 1.17(t, J=7.6 Hz, 3H), 2.56(q, J=7.6 Hz, 2H), 2.95 (ddd, J=3.6, 6.2 and 10.1 Hz, 1H), 3.58(dd, J=9.1 and 10.1 Hz, 1H), 3.76(dd, J= 6.2 and 11.3 Hz, 1H), 3.84(t, J=8.7 Hz, 1H), 3.92(dd, J=3.6 and 11.3 Hz, 1H), 4.05(d, J=14.0 Hz, 1H), 4.25(d, J=14.0 Hz, 1H), 5.23(d, J=8.7 Hz, 1H), 7.05(d, J=8.2 Hz, 2H), 7.17(d, J=8.2 Hz, 2H), 7.27(m, 2H), 7.75(d, J= 8.5 Hz, 1H), 8.08(dd, J=1.2 and 5.0 Hz, 1H). ESI m/z=414 (M+Na) mp 219.0-222.0° C. |
| Compound 23 | | $^1$H-NMR (300 MHz, CD$_3$OD): δ 1.18(t, J=7.6 Hz, 3H), 2.58(q, J=7.6 Hz, 2H), 2.94 (m, 1H), 3.60(dd, J=8.9, 9.9 Hz, 1H), 3.74(dd, J=6.2 and 11.3 Hz, 1H), 3.87 (t, J=8.9 Hz, 1H), 3.91(dd, J=3.7 and 11.3 Hz, 1H), 4.02(d, J=14.0 Hz, 1H), 4.22(d, J=14.0 Hz, 1H), 6.15(d, J=8.9 Hz, 1H), 7.08(m, J$_{AB}$=7.9 Hz, 2H), 7.19(m, J$_{AB}$=7.9 Hz, 2H), 8.05-8.08(m, 2H). ESI m/z=415 (M+Na) mp 181.0-183.5° C. |
| Compound 24 | | $^1$H-NMR (300 MHz, CD3OD): δ 1.18(t, J=7.6 Hz, 3H), 2.35(s, 3H), 2.53(s, 3H), 2.57(q, J=7.6 Hz, 2H), 2.99(m, 1H), 3.57(dd, J=8.9, 9.9 Hz, 1H), 3.74(dd, J= 6.4 and 11.5 Hz, 1H), 3.80(t, J=8.9 Hz, 1H), 3.85(d, J=15.2 Hz, 1H), 3.93 (dd, J=3.9 and 11.5 Hz, 1H), 4.05(d, J=15.2 Hz, 1H), 6.33(d, J=8.9 Hz, 1H), 7.04-7.10(m, 4H). ESI m/z=443 (M+Na) mp143.0-147.5° C. |
| Compound 25 | | $^1$H-NMR (300 MHz, CD3OD): δ 1.17(t, J=7.6 Hz, 3H), 2.15(s, 3H), 2.38(s, 3H), 2.56(q, J=7.6 Hz, 2H), 2.95(m, 1H), 3.56(dd, J=9.0, 10.1 Hz, 1H), 3.74(dd, J=6.5 and 11.6 Hz, 1H), 3.74-3.88(m, 2H), 3.92(dd, J=3.9 and 11.6 Hz, 1H), 4.60(d, J=15.2 Hz, 1H), 6.23(d, J=8.9 Hz, 1H), 6.70(s, 1H), 7.05(s, 4H). ESI m/z=442 (M+Na) mp 155.0-157.0° C. |
| Compound 26 | | $^1$H-NMR (300 MHz, CD3OD): δ 1.20(t, J=7.6 Hz, 3H), 2.60(q, J=7.6 Hz, 2H), 3.09 (m, 1H), 3.24(t, J=9.0 Hz, 1H), 3.54(dd, J=9.0 and 10.3 Hz, 1H), 3.70-3.84 (m, 4H), 3.92(m, 1H), 5.00(d, J=9.9 Hz, 1H), 6.42(d, J=7.6 Hz, 1H), 7.11-7.16(m, 4H), 7.57(d, J=2.5 Hz, 1H), 7.82(dd, J=2.5 and 7.6 Hz, 1H). ESI m/z=414 (M+Na) |

-continued

| Compound No. | Structural formula | ¹NMR, MS, mp |
|---|---|---|
| Compound 27 | (4-cyclopropylbenzyl pyridine thioglucoside structure) | ¹H-NMR (300 MHz, CD₃OD): δ 0.63(m, 2H), 0.92(m, 2H), 1.86(m, 1H), 2.98(m, 1H), 3.59(dd, J=9.0, 10.1 Hz, 1H), 3.77-3.94(m, 3H), 3.97(d, J=15.0 Hz, 1H), 4.03 (d, J=15.0 Hz, 1H), 5.31(d, J=8.7 Hz, 1H), 6.99(m, J$_{AB}$=8.2 Hz, 2H), 7.05(d, J=4.8 Hz, 1H), 7.11(m, J$_{AB}$=8.2 Hz, 2H), 8.07(m, 1H), 8.52(s, 1H). ESI m/z=426 (M+Na) mp155.0-159.0° C. |
| Compound 28 | (4-isopropylbenzyl pyridine thioglucoside structure) | ESI m/z=428 (M+Na) mp 78.0-81.5° C. |
| Compound 29 | (4-methoxybenzyl pyridine thioglucoside structure) | ESI m/z=416 (M+Na) mp 145.0-160.0° C. |
| Compound 30 | (4-(2-hydroxypropan-2-yl)benzyl pyridine thioglucoside structure) | ¹H-NMR (300 MHz, CD3OD): δ 1.50(s, 6H), 2.93-3.03(m, 1H), 3.59(t, J=8.8 Hz, 1H), 3.78(dd, J=6.4, 11.3 Hz, 1H), 3.84(t, J=8.8 Hz, 1H), 3.93(dd, J=3.6, 11.3 Hz, 1H), 3.98-4.11(m, 2H), 5.32(d, J=8.8 Hz, 1H), 7.10(d, J=4.9 Hz, 1H), 7.21(d, J=8.5 Hz, 2H), 7.41(d, J=8.5 Hz, 2H), 8.03(d, J=4.9 Hz, 1H), 8.53(s, 1H). ESI m/z=444 (M+Na) |

-continued

| Compound No. | Structural formula | ¹NMR, MS, mp |
|---|---|---|
| Compound 31 | | ESI m/z=444 (M+Na)<br>mp 174.0-175.0° C. |
| Compound 32 | | ¹H-NMR (300 MHz, CD3OD): δ 2.78(t, J=7.2 Hz, 2H), 2.95-3.02(m, 1H), 3.58(dd, J=9.0 and 10.3 Hz, 1H), 3.72(t, J=7.2 Hz, 2H), 3.78(dd, J=6.0, 11.8 Hz, 1H), 3.83(t, J=8.9 Hz, 1H), 3.93(dd, J=3.7, 11.8 Hz, 1H), 3.93-4.09(m, 2H), 5.31 (d, J=8.9 Hz, 1H), 7.09(d, J=4.8 Hz, 1H), 7.13-7.18(m, 4H), 8.13(d, J= 4.8 Hz, 1H), 8.52(s, 1H).<br>ESIm/z=430 (M+Na)<br>mp 194.5-195.0° C. |
| Compound 33 | | ESI m/z=434 (M+Na)<br>mp 179.0-180.5° C. |
| Compound 34 | | ESI m/z=416 (M+Na)<br>mp 153.5-155.0° C. |
| Compound 35 | | ESI m/z=434 (M+Na)<br>mp 155.0-157.5° C. |

-continued

| Compound No. | Structural formula | ¹NMR, MS, mp |
|---|---|---|
| Compound 36 | | ¹H-NMR (300 MHz, CD₃OD): δ 1.20(t, J=7.6 Hz, 3H), 2.15(s, 3H), 2.59(q, J= 7.6 Hz, 2H), 2.91(ddd, J=3.6, 6.5 and 10.3 Hz, 1H), 3.58(t, J=9.9 Hz, 1H), 3.70-3.98(m, 5H), 6.16(d, J=8.7 Hz, 1H), 7.08-7.13(m, 4H), 7.38(d, J= 7.9 Hz, 1H), 7.62(brd, J=7.9 Hz, 1H). ESI m/z=471 (M+Na), 447 (M−H). |
| Compound 37 | | ¹H-NMR (300 MHz, CD3OD): δ 2.92-2.99(m, 1H), 3.58(dd, J=9.0, 10.3 Hz, 1H), 3.73-3.94(m, 3H), 4.14(d, J=14.0 Hz, 1H), 4.34(d, J=14.0 Hz, 1H), 5.27(d, J=8.7 Hz, 1H), 6.48(dd, J=1.9, 2.5 Hz, 1H), 7.30(dd, J=4.8, 8.4 Hz, 1H), 7.41(d, J=8.7 Hz, 2H), 7.59(d, J=8.7 Hz, 2H), 7.67(d, J=1.9 Hz, 1H), 7.76-7.79(m, 1H), 8.10-8.14(m, 2H). ESIm/z=452 (M+Na) |
| Compound 38 | | ¹H-NMR (300 MHz, CD3OD): δ 1.21(t, J=7.6 Hz, 3H), 2.62(q, J=7.6 Hz, 2H), 3.00 (m, 1H), 3.35(t, J=9.9 Hz, 1H), 3.63(dd, J=9.0, 9.9 Hz, 1H), 3.80(dd, 1H), 3.87-3.93(m, 2H), 3.96(s, 2H), 6.37(d, J=8.7 Hz, 1H), 7.17(s, 4H), 7.24 (d, J=4.7 Hz, 1H), 8.68(d, J=4.7 Hz, 1H). ESI m/z=415 (M+Na). |

Test Example

According to the reported procedure (Aanal. Biochem., vol. 201, p. 301, 1984), a suspension of rat renal brush border membrane vehicles (BBMVs) was prepared (protein concentration: 4 mg/mL). This suspension (50 μL) was pre-incubated at 37° C. for 2 minutes, followed by addition of 150 μL reaction solution containing a test compound dissolved in DMSO (final DMSO content: 1%) as well as 100 mM mannitol, 100 mM NaSCN or KSCN, 10 mM HEPES/Tris (pH 7.4), D-glucose (final concentration: 0.1 mM) and 1 μCi D-[6-³H]glucose (Amersham). After reaction at 37° C. for 5 seconds, 1 mL ice-cold reaction stop solution (150 mM NaCl, 10 mM HEPES/Tris (pH 7.4), 0.3 mM phloridzin) was added to the reaction mixture to stop the reaction. The reaction mixture was immediately filtered by rapid filtration using a membrane filter (pore size: 0.45 μm, HAWP02500, Millipore) to separate BBMVs. This membrane filter was washed three times with 4.5 mL ice-cold reaction stop solution, dried sufficiently and then assayed for radioactivity using a liquid scintillation counter (Beckman) to determine the amount of glucose trapped inside the BBMVs on the membrane filter.

Assuming that the amount of trapped glucose in the absence of a test compound was set to 100%, the concentration required for the test compound to cause 50% inhibition of the amount of trapped glucose was calculated ($IC_{50}$ value).

The results obtained were shown in Table 2 below.

TABLE 2

| Compound | $IC_{50}$ (μM) |
|---|---|
| Compound 1 | 0.49 |
| Compound 2 | 0.31 |
| Compound 3 | 0.18 |
| Compound 4 | 0.26 |
| Compound 5 | 0.56 |
| Compound 6 | 0.52 |
| Compound 13 | 0.63 |
| Compound 20 | 0.14 |
| Compound 27 | 0.43 |

INDUSTRIAL APPLICABILITY

The present invention enables the provision of heteroaryl 5-thio-β-D-glucopyranoside compounds or pharmaceutically acceptable salts thereof which have an excellent inhibitory effect on SGLT2 activity. The compounds of the present invention are effective as prophylactic or therapeutic agents for diabetes, diabetes-related diseases or diabetic complications.

What is claimed is:

1. A 5-thio-β-D-glucopyranoside compound of the following formula or a pharmaceutically acceptable salt thereof or a hydrate thereof:

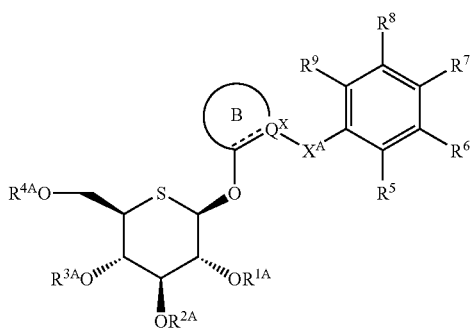

wherein

B represents a heteroaryl group which may be substituted with any substituent, $R^{1A}$, $R^{2A}$, $R^{3A}$ and $R^{4A}$, which may be the same or different, each represent a hydrogen atom, a $C_{2-10}$ acyl group, a $C_{7-10}$ aralkyl group, a $C_{2-6}$ alkoxycarbonyl group, a $C_{1-6}$ alkoxy-$C_{2-10}$ acyl group or a $C_{1-6}$ alkoxy-$C_{2-6}$ alkoxycarbonyl group, $Q^X$ represents N or C, $X^A$ represents —(CH$_2$)n-, —CO(CH$_2$)n-, —C(OH)(CH$_2$)n-, —O—(CH$_2$)n-, —CONH(CH$_2$)n-, —NHCO(CH$_2$)n- (wherein n is an integer of 0 to 3), —COCH═CH—, —S— or —NH—, provided that when $Q^X$ is N, $X^A$ represents —(CH$_2$)n-, —CO(CH$_2$)n-, —C(OH)(CH$_2$)n-, —CONH(CH$_2$)n- wherein n is an integer of 0 to 3 or —COCH═CH—, and $R^5$, $R^6$, $R^7$, $R^8$ and $R^9$, which may be the same or different, each represent:

a hydrogen atom;

a halogen atom;

a hydroxyl group;

a $C_{1-6}$ alkyl group which may be substituted with one or more substituents selected from the group consisting of a halogen atom and a hydroxyl group;

a group represented by the formula:

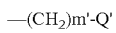

—(CH$_2$)m'-Q' wherein m' represents an integer of 0 to 4, and Q' represents a formyl group, an amino group, a nitro group, a cyano group, a carboxyl group, a sulfonic acid group, an optionally halogen-substituted $C_{1-6}$ alkoxy group, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(═O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N—($C_{1-6}$ alkyl)aminocarbonyl group, or an N,N-di($C_{1-6}$ alkyl)aminocarbonyl group; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

2. The compound according to claim 1, wherein $X^A$ is —(CH$_2$)n- or —CO(CH$_2$)n- wherein n is an integer of 0 to 3, or a pharmaceutically acceptable salt thereof or a hydrate thereof.

3. The compound according to claim 1, wherein $X^A$ is —CH$_2$— or —CO—, or a pharmaceutically acceptable salt thereof or a hydrate thereof.

4. The compound according to claim 1, wherein $X^A$ is —CH$_2$—, or a pharmaceutically acceptable salt thereof or a hydrate thereof.

5. The compound according to any one of claims 1 to 4, wherein the moiety represented by the formula:

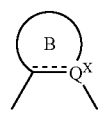

is a group represented by the formula:

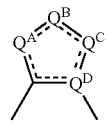

wherein at least one of $Q^A$ to $Q^D$ represents a nitrogen atom, and the other each independently represent —C-$Z^Y$, provided that when $Q^D$ is C, any one of the ring nitrogen atoms may be substituted with $Z^X$ wherein $Z^X$ represents an optionally halogen-substituted $C_{1-6}$ alkyl group; an optionally halogen-substituted $C_{3-7}$ cycloalkyl group; a $C_{2-10}$ acyl group; a $C_{2-6}$ alkoxycarbonyl group; a phenyl or $C_{7-10}$ aralkyl group which may be substituted with one or more substituents selected from the group consisting of a halogen atom, a $C_{1-6}$ alkyl group, a $C_{1-6}$ alkoxy group, an amino group, a nitro group, a cyano group, a carboxyl group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylamino group, an N,N-di($C_{1-6}$ alkyl)amino group, an N—($C_{1-6}$ alkyl)aminocarbonyl group and an N,N-di($C_{1-6}$ alkyl)aminocarbonyl group; a pyridyl group; a thienyl group; a furanyl group; or pyrimidinyl group, and $Z^Y$ independently represents a hydrogen atom; a halogen atom; a $C_{1-6}$ alkyl group which may be substituted with one or more substituents selected from the group consisting of a halogen atom, a hydroxyl group and a $C_{1-6}$ alkoxy group; an optionally halogen-substituted $C_{3-7}$ cycloalkyl group; a carboxyl group; or a $C_{2-6}$ alkoxycarbonyl group, or a pharmaceutically acceptable salt thereof or a hydrate thereof.

6. The compound according to any one of claims 1 to 4, wherein the moiety represented by the formula:

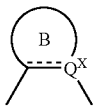

is a pyrazole group represented by the formula:

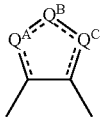

wherein when $Q^A$ is N and $Q^B$ is —N-$Z^1$ or when $Q^A$ is —N-$Z^2$ and $Q^B$ is N, $Q^C$ represents —C-$Z^3$, or alternatively, when $Q^B$ is N and $Q^C$ is —N-$Z^4$ or when $Q^B$ is —N-$Z^5$ and $Q^C$ is N, $Q^A$ represents —C-$Z^6$ wherein $Z^1$, $Z^2$, $Z^4$ and $Z^5$ each independently represent a hydrogen atom; an optionally halogen-substituted $C_{1-6}$ alkyl group; an optionally halogen-substituted $C_{3-7}$ cycloalkyl group; a $C_{2-10}$ acyl group; a $C_{2-6}$ alkoxycarbonyl group; a phenyl or $C_{7-10}$ aralkyl group which may be substituted with one or more substituents selected from the group consisting of a halogen atom, a $C_{1-6}$ alkyl group, a $C_{1-6}$ alkoxy group, an amino group, a nitro group, a cyano group, a carboxyl group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylamino group, an N,N-di($C_{1-6}$ alkyl)amino group, an N—($C_{1-6}$ alkyl)aminocarbonyl group and an N,N-di($C_{1-6}$ alkyl)aminocarbonyl group; a pyridyl group; a thienyl group; a furanyl group; or a pyrimidinyl group, and $Z^3$ and $Z^6$ each independently represent a hydrogen atom; a halogen atom; a $C_{1-6}$ alkyl group which may be substituted with one or more substituents selected from the group consisting of a halogen atom, a hydroxyl group and a $C_{1-6}$ alkoxy group; an optionally halogen-substituted $C_{3-7}$ cycloalkyl group; a carboxyl group; or a $C_{2-6}$ alkoxycarbonyl group, or a pharmaceutically acceptable salt thereof or a hydrate thereof.

7. The compound according to any one of claims 1 to 4, wherein the moiety represented by the formula:

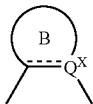

is a pyridyl group represented by the formula:

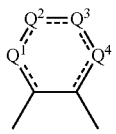

wherein any one of $Q^1$ to $Q^4$ represents N and the other each independently represent —C-$Z^7$ wherein $Z^7$ represents a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group, or a pharmaceutically acceptable salt thereof or a hydrate thereof.

8. The compound according to any one of claims 1 to 4, wherein the moiety represented by the formula:

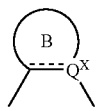

is a pyrimidyl group represented by the formula:

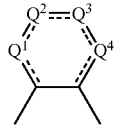

wherein when $Q^1$ and $Q^3$ are each N, $Q^2$ and $Q^4$ each independently represent —C-$Z^8$, or alternatively, when $Q^2$ and $Q^4$ are each N, $Q^1$ and $Q^3$ each independently represent —C-$Z^9$ wherein $Z^8$ and $Z^9$ each independently represent a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group, or a pharmaceutically acceptable salt thereof or a hydrate thereof.

9. The compound according to any one of claims 1 to 4, wherein the moiety represented by the formula:

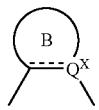

is a pyridazinyl group represented by the formula:

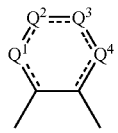

wherein $Q^1$ and $Q^2$, $Q^2$ and $Q^3$, or $Q^3$ and $Q^4$ each represent N, and the other each represent —C-$Z^{10}$ wherein $Z^{10}$ independently represents a hydrogen atom, a halogen atom, an optionally halogen-substituted $C_{1-6}$ alkyl group, a $C_{1-6}$ alkoxy group, an amino group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group, or a pharmaceutically acceptable salt thereof or a hydrate thereof.

10. The compound according to any one of claims 1 to 4, wherein the moiety represented by the formula:

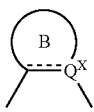

is a pyrazinyl group represented by the formula:

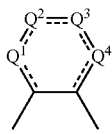

wherein $Q^1$ and $Q^4$ each represent N and the other each represent —C-$Z^{11}$ wherein $Z^{11}$ independently represents a hydrogen atom, a halogen atom, an optionally halogen-substituted $C_{1-6}$ alkyl group, an amino group, a $C_{1-6}$ alkoxy group, a $C_{1-6}$ alkylamino group, an N,N-di($C_{1-6}$ alkyl)amino group, a $C_{2-10}$ acylamino group, a $C_{2-10}$ acyl group or an optionally halogen-substituted $C_{3-7}$ cycloalkyl group, or a pharmaceutically acceptable salt thereof or a hydrate thereof.

11. A 5-thio-β-D-glucopyranoside compound of the following formula or a pharmaceutically acceptable salt thereof:

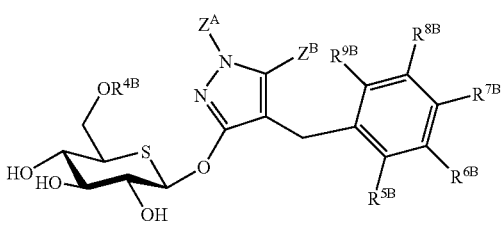

wherein $Z^A$ represents a hydrogen atom, a $C_{1-6}$ alkyl group, a halogen-substituted $C_{1-6}$ alkyl group, a $C_{3-6}$ cycloalkyl group, a benzyl group, a $C_{2-10}$ acyl group or a $C_{2-6}$ alkoxycarbonyl group, $Z^B$ represents a $C_{1-6}$ alkyl group or a halogen-substituted $C_{1-6}$ alkyl group, $R^{5B}$ to $R^{9B}$, which may be the same or different, each represent a hydrogen atom, a halogen atom, a $C_{1-6}$ alkyl group, a halogen-substituted $C_{1-6}$ alkyl group, a $C_{3-6}$ cycloalkyl group, a $C_{1-6}$ alkoxy group, a halogen-substituted $C_{1-6}$ alkoxy group or a $C_{1-6}$ alkylthio group, and $R^{4B}$ represents a hydrogen atom, a $C_{2-10}$ acyl group or a $C_{2-6}$ alkoxycarbonyl group.

12. A pharmaceutical preparation, which comprises the 5-thio-β-D-glucopyranoside compound according to claim 1 or a pharmaceutically acceptable salt thereof or a hydrate thereof as an active ingredient.

13. The pharmaceutical preparation according to claim 12, which is an inhibitor of sodium-dependent glucose transporter 2 activity.

14. The pharmaceutical preparation according to claim 13, which is a prophylactic or therapeutic agent for diabetes, diabetes-related diseases or diabetic complications.

15. A pharmaceutical preparation, which comprises the 5-thio-β-D-glucopyranoside compound according to claim 1 or a pharmaceutically acceptable salt thereof or a hydrate thereof, in combination with at least one drug selected from the group consisting of an insulin sensitizer selected from the group consisting of a PPARγ agonist; a PPARα/γ agonist; a PPAR δ agonist; and a PPARα/γ/δ agonist, a glycosidase inhibitor, a biguanide, an insulin secretagogue, an insulin formulation and a dipeptidyl peptidase IV inhibitor.

16. A pharmaceutical preparation, which comprises the 5-thio-β-D-glucopyranoside compound according to claim 1 or a pharmaceutically acceptable salt thereof or a hydrate thereof, in combination with at least one drug selected from the group consisting of a hydroxymethylglutaryl coenzyme A reductase inhibitor, a fibrate, a squalene synthase inhibitor, an acyl-coenzyme A:cholesterol acyltransferase inhibitor, a low-density lipoprotein receptor promoter, a microsomal triglyceride transfer protein inhibitor and an anorectic.

* * * * *